US009428811B2

(12) United States Patent
Evans et al.

(10) Patent No.: US 9,428,811 B2
(45) Date of Patent: Aug. 30, 2016

(54) EPIGENOMIC INDUCED PLURIPOTENT STEM CELL SIGNATURES

(71) Applicant: Salk Institute for Biological Studies, La Jolla, CA (US)

(72) Inventors: Ronald M. Evans, La Jolla, CA (US); Joseph R. Ecker, Carlsbad, CA (US); Ryan Lister, San Diego, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 303 days.

(21) Appl. No.: 13/872,983

(22) Filed: Apr. 29, 2013

(65) Prior Publication Data

US 2013/0295569 A1 Nov. 7, 2013

Related U.S. Application Data

(63) Continuation of application No. PCT/US2011/058454, filed on Oct. 28, 2011.

(60) Provisional application No. 61/407,873, filed on Oct. 28, 2010.

(51) Int. Cl.
 *C12Q 1/68* (2006.01)
(52) U.S. Cl.
 CPC ....... *C12Q 1/6881* (2013.01); *C12N 2799/027* (2013.01); *C12Q 2600/154* (2013.01)
(58) Field of Classification Search
 None
 See application file for complete search history.

(56) References Cited

U.S. PATENT DOCUMENTS

| | | |
|---|---|---|
| 7,981,603 B2 | 7/2011 | Feinberg |
| 2005/0227230 A1 | 10/2005 | Carroll et al. |
| 2005/0227231 A1 | 10/2005 | Tcherkassov |
| 2006/0188986 A1 | 8/2006 | Millar et al. |
| 2010/0172880 A1 | 7/2010 | Laird et al. |
| 2012/0164110 A1 | 6/2012 | Feinberg et al. |

FOREIGN PATENT DOCUMENTS

WO    WO 2006/046076 A2    5/2006

OTHER PUBLICATIONS

Deng et al; Nature Biotechnology, vol. 27, pp. 353-360; Apr. 2009.*
Ramsahoye et al; PNAS vol. 97, 2000, pp. 5237-5242.*
Harris et al., "Comparison of sequencing-based methods to profile DNA methylation and identification of monoallelic epigenetic modifications," *Nat. Biotechnol.* 28(10): 1097-1105 (Oct. 2010).
International Search Report from parent PCT Application No. PCT/US2011/058454, 5 pages (mailed May 8, 2012).
Lister et al., "Hotspots of aberrant epigenomic reprogramming in human induced pluripotent stem cells," *Nature* 471(7336): 68-73 (Mar. 3, 2011).

Lister et al., "Human DNA methylomes at base resolution show widespread epigenomic differences," *Nature* 462(7271): 315-322 (Nov. 19, 2009).
Aoi et al., "Generation of pluripotent stem cells from adult mouse liver and stomach cells," *Science* 321:699-702 (Aug. 1, 2008).
Bar-Nur et al., "Epigenetic memory and preferential lineage-specific differentiation in induced pluripotent stem cells derived from human pancreatic islet beta cells," *Cell Stem Cell* 9:17-23 (Jul. 8, 2011).
Bock et al., "Reference maps of human ES and iPS cell variation enable high-throughput characterization of pluripotent cell lines," *Cell* 144:439-452 (Feb. 4, 2011).
Cahan et al., "CellNet: network biology applied to stem cell engineering," *Cell* 158:903-915 (Aug. 14, 2014).
Doi et al., "Differential methylation of tissue- and cancer-specific CpG island shores distinguishes human induced pluripotent stem cells, embryonic stem cells and Fibroblasts," *Nature Genetics* 41(12):1350-1354 (Dec. 2009).
Hu et al., "Memory in induced pluripotent stem cells: reprogrammed human retinal-pigmented epithelial cells show tendency for spontaneous redifferentiation," *Stem Cells* 28:1981-1991 (2010).
Kim et al., "Direct reprogramming of human neural stem cells by OCT4," *Nature* 461:649-654 (Oct. 1, 2009).
Kim et al., "Donor cell type can influence the epigenome and differentiation potential of human induced pluripotent stem cells," *Nature Biotechnology* 29(12):1117-1119 (Dec. 2011).
Kim et al., "Epigenetic memory in induced pluripotent stem cells," *Nature* 467(7313): 285-290 (Sep. 16, 2010).
Ma et al., "Abnormalities in human pluripotent cells due to reprogramming mechanisms," *Nature* 511:177-183 (Jul. 10, 2014).
Nazor et al., "Recurrent variations in DNA methylation in human pluripotent stem cells and their differentiated derivatives," *Cell Stem Cell* 10:620-634 (May 4, 2012).
Ohi et al., "Incomplete DNA methylation underlies a transcriptional memory of somatic cells in human iPS cells," *Nature Cell Biology* 13(5):541-549 (May 2011).
Park et al., "Reprogramming of human somatic cells to pluripotency with defined factors," *Nature* 451:141-147 (Jan. 10, 2008) (released on-line 2007).
Polo et al., "Cell type of origin influences the molecular and functional properties of mouse induced pluripotent stem cells," *Nature Biotechnology* 28(8):848-855 (Aug. 2010).
Quattrocelli et al., "Intrinsic cell memory reinforces myogenic commitment of pericyte-derived iPSCs," *Journal of Pathology* 223:593-603 (Feb. 21, 2011).
Ruiz et al., "Identification of a specific reprogramming-associated epigenetic signature in human induced pluripotent stem cells," *PNAS* 109(40):16196-16201 (Oct. 2, 2012).
Wernig et al., "In vitro reprogramming of fibroblasts into a pluripotent ES-cell-like state," *Nature* 448:318-325 (Jul. 19, 2007).
Xu et al., "Highly efficient derivation of ventricular cardiomyocytes from induced pluripotent stem cells with a distinct epigenetic signature," *Cell Research* 22:142-154 (2012).

* cited by examiner

*Primary Examiner* — Jehanne Sitton
(74) *Attorney, Agent, or Firm* — Klarquist Sparkman, LLP

(57) ABSTRACT

Provided herein are methods of characterizing the epigenetic signature of human induced pluripotent stem cells. The methods are useful in identifying human induced pluripotent stem cells (hiPSCs), diagnostic markers for incomplete hiPSCs reprogramming, and characterization of the efficacy of different reprogramming techniques.

12 Claims, 31 Drawing Sheets

EPIGENOMIC INDUCED PLURIPOTENT STEM CELL SIGNATURES

CROSS-REFERENCES TO RELATED APPLICATIONS

This application is a continuation of PCT Application No. PCT/US2011/058454, filed Oct. 28, 2011 which claims the benefit of U.S. Provisional Application No. 61/407,873, filed Oct. 28, 2010, the contents of which are incorporated herein by reference in their entirety for all purposes.

STATEMENT AS TO RIGHTS TO INVENTIONS MADE UNDER FEDERALLY SPONSORED RESEARCH OR DEVELOPMENT

This invention was made with government support under U01ES017166, NSF 0726408, and DK062434 awarded by the National Institutes of Health. The Government has certain rights in the invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 92150-824012_ST25.TXT, created on Apr. 29, 2013, 28,376 bytes, machine format IBM-PC, MS-Windows operating system, is hereby incorporated by reference.

BACKGROUND OF THE INVENTION

Generation of iPSCs from somatic cells offers tremendous potential for therapeutics, the study of disease states, and elucidation of developmental processes (Soldner, F. et al. *Cell* 136:964-977 (2009); Yamanaka, S. *Cell* 137:13-17 (2009)). iPSC production techniques introduce active genes that are necessary for pluripotency, or their derivative RNA or protein products, into a somatic cell to induce pluripotent cellular properties that closely resemble those of embryonic stem cells (ESCs) (Takahashi, K. et al., *Cell* 126:663-676 (2006); Takahashi, K. et al. *Cell* 131:861-872 (2007); Yu, J. et al. *Science* 318:1917-1920 (2007); Park, I. et al. *Nature* 451:141-146 (2008); Yu, J. et al. *Science* 324:797-801 (2009); Zhao, X. Y. et al. *Nature* 461:86-90 (2009)). Indeed, iPSCs have been used to produce viable and fertile adult mice, demonstrating their pluripotent potential to form all adult somatic and germline cell types (Zhao, X. Y. et al. *Nature* 461:86-90 (2009); Boland, M. J. et al. *Nature* 461:91-94 (2009)).

Fundamentally, the reprogramming process by which a somatic cell acquires pluripotent potential is not a genetic transformation, but an epigenetic one, where the term epigenetic is used to refer to molecular modifications and interactions that impact upon the cellular readout of the genome, such as covalent modifications of DNA and histones, and protein DNA-interactions.

Optimal reprogramming of somatic cells to a pluripotent state requires complete reversion of the somatic epigenome into an ESC-like state, but to date a comprehensive survey of the changes in such epigenetic marks in a variety of independent iPSC lines has not been reported. Therefore, there is a need in the art to understand the epigenomic and methylation characteristics of induced pluripotent stem cells.

Accordingly, Applicants have performed the first whole-genome profiling of the DNA methylomes of multiple ESC, iPSC, and somatic progenitor lines, encompassing reprogramming performed in different laboratories, using different iPSC-inducing technologies, and cells derived from distinct germ layers. This comprehensive base-resolution epigenomic profiling shows that while on a global scale ESC and iPSC methylomes are very similar, iPSC lines display significant reprogramming variability compared to ESCs, including both somatic "memory" and aberrant reprogramming of DNA methylation. Furthermore, all iPSC lines share numerous aberrantly methylated, non-randomly distributed, megabase-scale genic and non-genic regions that Applicants have termed non-CG mega-DMRs. In iPSCs these regions display incomplete or inappropriate reprogramming of the pluripotency-specific non-CG methylation, and are associated with localized differences in CG methylation and transcriptional abnormalities at genes associated with neural development and function.

BRIEF SUMMARY OF THE INVENTION

The methods provided herein are based, inter alia, on the discovery that human induced pluripotent stem cells possess epigenomic signatures relative to human embryonic stem cell. The methods and DMRs provided herein are useful in identifying hiPSCs, diagnostic markers for incomplete hiPSC reprogramming, characterization of the efficacy of different reprogramming techniques, and potential propagation of altered methylation states in derivative differentiated cells.

In one aspect, provided herein is a method of identifying a human induced pluripotent stem cell (hiPSC). The method includes identifying a non-CpG hypomethylated DMR within the human induced pluripotent stem cell. The human induced pluripotent stem cell may be an incompletely reprogrammed hiPSC.

In another aspect, provided herein is a method of identifying a human induced pluripotent stem cell (hiPSC). The method includes identifying a hypomethylated CG-DMR or a hypermethylated CG-DMR within the human induced pluripotent stem cell.

In another aspect, a method of identifying a human induced pluripotent stem cell (hiPSC) is provided. The method includes identifying one or more of a hypomethylated CG-DMR, one or more a hypermethylated CG-DMR or one or more of a non CpG hypomethylated DMR within the human induced pluripotent stem cell.

In another aspect, a method of identifying a human induced pluripotent stem cell is provided. The method includes determining a methylation pattern of at least a portion of a subject cell and comparing the methylation pattern to a human embryonic stem cell methylation pattern. A difference in methylation pattern is indicative of the subject cell being a human induced pluripotent stem cell. The human induced pluripotent stem cell may be an incompletely reprogrammed induced pluripotent stem cell.

BRIEF DESCRIPTION OF THE DRAWINGS

FIG. 2. Partially methylated domains (PMDs) become highly methylated upon induction of pluripotency.

FIG. 3. CG-DMRs identified between pluripotent cells.

FIG. 4. Characterization of CG-DMRs in iPSCs.

FIG. 5. Failure to restore megabase-scale regions of non-CG methylation is a hallmark of iPSC reprogramming.

FIG. 6. Global similarity in transcriptional and DNA methylation patterns between ESCs and iPSCs.

FIG. 19. Validation of the CG-DMRs in two additional ESC lines.

FIG. 20. non-CG mega-DMRs.

DETAILED DESCRIPTION OF THE INVENTION

I. Definitions

Figure 1A:
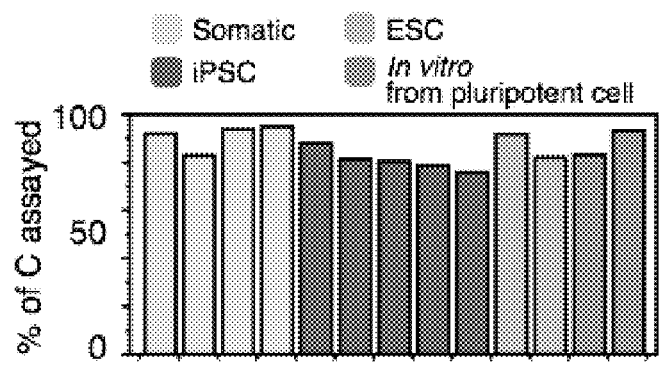
(FIG. 1a) Percent of all cytosines on each strand of the human genome assayed for each sample. The percent of all sequencing base calls that were methylated (C, resistant to bisulfite conversion) at covered C bases in the (FIG. 1b) CG and (FIG. 1c) CH contexts (where H=A, C, or T) throughout the genome, minus the bisulfite non-conversion frequency. For each group of the histogram in FIG. 1A-1C the entries depicted from left to right are somatic, iPSC, ESC and in vitro from pluripotent cell, respectively.

The following definitions are provided to facilitate understanding of certain terms used frequently herein and are not meant to limit the scope of the present disclosure.

"Nucleic acid" refers to deoxyribonucleotides or ribonucleotides and polymers thereof in either single- or double-stranded form, and complements thereof.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The terms "identical" or percent "identity," in the context of two or more nucleic acids, refer to two or more sequences or subsequences that are the same or have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., the NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

The phrase "stringent hybridization conditions" refers to conditions under which a probe will hybridize to its target sequence, typically in a complex mixture of nucleic acids, but to not other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

A variety of methods of specific DNA and RNA measurement that use nucleic acid hybridization techniques are known to those of skill in the art (see, Sambrook, supra). Some methods involve electrophoretic separation (e.g., Southern blot for detecting DNA, and Northern blot for detecting RNA), but measurement of DNA and RNA can also be carried out in the absence of electrophoretic separation (e.g., by dot blot).

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation. It is understood that various detection probes, including Taqman® and molecular beacon probes can be used to monitor amplification reaction products, e.g., in real time.

The word "polynucleotide" refers to a linear sequence of nucleotides. The nucleotides can be ribonucleotides, deoxyribonucleotides, or a mixture of both. Examples of polynucleotides contemplated herein include single and double stranded DNA, single and double stranded RNA (including miRNA), and hybrid molecules having mixtures of single and double stranded DNA and RNA.

The words "protein", "peptide", and "polypeptide" are used interchangeably to denote an amino acid polymer or a set of two or more interacting or bound amino acid polymers.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

A "viral vector" is a viral-derived nucleic acid that is capable of transporting another nucleic acid into a cell. A viral vector is capable of directing expression of a protein or proteins encoded by one or more genes carried by the vector when it is present in the appropriate environment. Examples for viral vectors include, but are not limited to retroviral, adenoviral, lentiviral and adeno-associated viral vectors.

The term "transfection" or "transfecting" is defined as a process of introducing nucleic acid molecules to a cell by non-viral or viral-based methods. Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. For viral-based methods of transfection any useful viral vector may be used in the methods described herein. Examples for viral vectors include, but are not limited to retroviral, adenoviral, lentiviral and adeno-associated viral vectors.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell (Sambrook et al., 1989 *Molecular Cloning: A Laboratory Manual*, 18.1-18.88).

The term "plasmid" refers to a nucleic acid molecule that encodes for genes and/or regulatory elements necessary for the expression of genes. Expression of a gene from a plasmid can occur in cis or in trans. If a gene is expressed in cis, the gene and the regulatory elements are encoded by the same plasmid. Expression in trans refers to the instance where the gene and the regulatory elements are encoded by separate plasmids.

The term "episomal" refers to the extra-chromosomal state of a plasmid in a cell. Episomal plasmids are nucleic acid molecules that are not part of the chromosomal DNA and replicate independently thereof.

A "cell culture" is a population of cells residing outside of an organism. These cells are optionally primary cells isolated from a cell bank, animal, or blood bank, or secondary cells that are derived from one of these sources and have been immortalized for long-lived in vitro cultures.

A "stem cell" is a cell characterized by the ability of self-renewal through mitotic cell division and the potential to differentiate into a tissue or an organ. Among mammalian stem cells, embryonic and adult stem cells can be distinguished. Embryonic stem cells reside in the blastocyst and give rise to embryonic tissues, whereas adult stem cells reside in adult tissues for the purpose of tissue regeneration and repair.

The term "pluripotent" or "pluripotency" refers to cells with the ability to give rise to progeny that can undergo differentiation, under appropriate conditions, into cell types that collectively exhibit characteristics associated with cell lineages from the three germ layers (endoderm, mesoderm, and ectoderm). Pluripotent stem cells can contribute to tissues of a prenatal, postnatal or adult organism. A standard art-accepted test, such as the ability to form a teratoma in 8-12 week old SCID mice, can be used to establish the pluripotency of a cell population. However, identification of various pluripotent stem cell characteristics can also be used to identify pluripotent cells.

"Pluripotent stem cell characteristics" refer to characteristics of a cell that distinguish pluripotent stem cells from other cells. Expression or non-expression of certain combinations of molecular markers are examples of characteristics of pluripotent stem cells. More specifically, human pluripotent stem cells may express at least some, and optionally all, of the markers from the following non-limiting list: SSEA-3, SSEA-4, TRA-1-60, TRA-1-81, TRA-2-49/6E, ALP, Sox2, E-cadherin, UTF-1, Oct4, Lin28, Rex1, and Nanog. Cell morphologies associated with pluripotent stem cells are also pluripotent stem cell characteristics.

An "induced pluripotent stem cell" refers to a pluripotent stem cell artificially derived from a non-pluripotent cell. A non-pluripotent cell can be a cell of lesser potency to self-renew and differentiate than a pluripotent stem cell. Cells of lesser potency can be, but are not limited to, somatic stem cells, tissue specific progenitor cells, primary or secondary cells. Without limitation, a somatic stem cell can be a hematopoietic stem cell, a mesenchymal stem cell, an epithelial stem cell, a skin stem cell or a neural stem cell. A tissue specific progenitor refers to a cell devoid of self-renewal potential that is committed to differentiate into a specific organ or tissue. A primary cell includes any cell of an adult or fetal organism apart from egg cells, sperm cells and stem cells. Examples of useful primary cells include, but are not limited to, skin cells, bone cells, blood cells, cells of internal organs and cells of connective tissue. A secondary cell is derived from a primary cell and has been immortalized for long-lived in vitro cell culture.

The term "reprogramming" refers to the process of dedifferentiating a non-pluripotent cell (e.g. an origin cell) into a cell exhibiting pluripotent stem cell characteristics (e.g. a human induced pluripotent stem cell).

The terms "CG" or "CpG" can be used interchangeably and refer to regions of a DNA molecule where a cytosine nucleotide occurs next to a guanine nucleotide in the linear sequence of bases (linear strand) within the DNA molecule. Nucleotides forming a linear strand in a DNA molecule are linked through a phosphate. Therefore, a CG site is also referred to as a "CpG" site, a shorthand for cytosine-phosphate-guanine. The "CpG" notation is further used to distinguish the linear sequence of cytosine and guanine from the CG base-pairing of cytosine and guanine, where cytosine and guanine are located on opposite strands of a DNA molecule. Cytosines in CpG dinucleotides can be methylated to form 5-methylcytosine. In mammals, methylating the cytosine within a gene may turn the gene off. Enzymes that add a methyl group to a cytosine within a DNA molecule are referred to as DNA methyltransferases.

A "non-CpG hypomethylated DMR," as used herein, refers to a differentially methylated region (DMR) of an iPSC genome having a greater number of non-methylated non-CpG sites relative to the corresponding region of a human embryonic stem cell. The non-CpG hypomethylated DMR is typically about 100 kb to 4000 kb in length (e.g. 100 to 3000 kb or 100 to 2000 kb).

A non-CpG site is a nucleotide methylation site in which the nucleotide does not form part of a CG sequence.

A "hypomethylated CG-DMR," as used herein, refers to a differentially methylated region (DMR) of an iPSC genome having a greater number of non-methylated CpG sites relative to the corresponding region of a human embryonic stem cell. The hypomethylated CG DMR is typically about 100 to 4000 kb in length (e.g. 100 to 3000 kb or 100 to 2000 kb). A CpG cite is a nucleotide methylation cite in which the nucleotide forms part of a CG sequence.

A "hypermethylated CG-DMR," as used herein, refers to a differentially methylated region (DMR) of an iPSC genome having a greater number of methylated CpG sites relative to the corresponding region of a human embryonic stem cell. The hypermethylated CG DMR is typically about 100 to 4000 kb in length (e.g. 100 to 3000 kb or 100 to 2000 kb).

The term "hypermethylated promoter," as used herein, refers to a promoter region of an iPSC genome within or coextensive with a non-CpG hypomethylated DMR having a greater number of methylated sites relative to the corresponding region of a human embryonic stem cell.

The origin cell is typically a partially differentiated or fully differentiated human cell. Methods of reprogramming partially differentiated or fully differentiated human cells are well known in the art (e.g. using one or more of the Yamanaka reprogramming factors).

II. METHODS

In one aspect, provided herein is a method of identifying a human induced pluripotent stem cell (hiPSC). The method includes identifying a non-CpG hypomethylated DMR within the human induced pluripotent stem cell. The human induced pluripotent stem cell may be an incompletely reprogrammed hiPSC.

In some embodiments, the non-CpG hypomethylated DMR is characterized by decreased methylation relative to a corresponding non-CpG DMR of a human embryonic stem cell. The comparison may be performed using the criteria outlined below in the Example section entitled "Non-CG mega-DMRs" (Example 6; and see also FIG. 5). In some embodiments, the non-CpG hypomethylated DMR is one or more regions identified in Table 3A and/or Table 3B. Non limiting examples of chromosomal regions that are a non-CpG hypomethylated DMR include the nucleotide sequence of chromosome 7 from position 156,535,825 to position 158,080,000, the nucleotide sequence of chromosome 8 from position 2,161,971 to position 4,761,970, the nucleotide sequence of chromosome 10 from position 131,888,467 to position 133,321,763, or the nucleotide sequence of chromosome 22 from position 46,357,370 to position 48,540,808.

In some embodiments, the non-CpG hypomethylated DMR includes from about 100 kb to about 5000 kb. In other embodiments, the non-CpG hypomethylated DMR includes from about 200 kb to about 5000 kb, 300 kb to about 5000 kb, from about 400 kb to about 5000 kb, 500 kb to about 5000 kb, from about 600 kb to about 5000 kb, 700 kb to about 5000 kb, from about 800 kb to about 5000 kb, 900 kb to about 5000 kb, from about 1000 kb to about 5000 kb, 1100 kb to about 5000 kb, from about 1200 kb to about 5000 kb, 1300 kb to about 5000 kb, from about 1400 kb to about 5000 kb, 1500 kb to about 5000 kb, from about 1600 kb to about 5000 kb, 1700 kb to about 5000 kb, from about 1800 kb to about 5000 kb, 1900 kb to about 5000 kb, from about 2000 kb to about 5000 kb, 2100 kb to about 5000 kb, from about 2200 kb to about 5000 kb, 2300 kb to about 5000 kb, from about 2400 kb to about 5000 kb, 2500 kb to about 5000 kb, from about 2600 kb to about 5000 kb, 2700 kb to about 5000 kb, from about 2800 kb to about 5000 kb, 2900 kb to about 5000 kb, from about 3000 kb to about 5000 kb, 3100 kb to about 5000 kb, from about 3200 kb to about 5000 kb, 3300 kb to about 5000 kb, from about 3400 kb to about 5000 kb, 3500 kb to about 5000 kb, from about 3600 kb to about 5000 kb, 3700 kb to about 5000 kb, from about 3800 kb to about 5000 kb, 3900 kb to about 5000 kb, from about 4000 kb to about 5000 kb, 4100 kb to about 5000 kb, from about 4200 kb to about 5000 kb, 4300 kb to about 5000 kb, from about 4400 kb to about 5000 kb, 4500 kb to about 5000 kb, from about 4600 kb to about 5000 kb, 4700 kb to about 5000 kb, from about 4800 kb to about 5000 kb, or 4900 kb to about 5000 kb. In some embodiments, the non-CpG hypomethylated DMR includes 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 4100, 4200, 4300, 4400, 4500, 4600, 4700, 4800, 4900, or 5000 kb.

In some embodiments, the non-CpG hypomethylated DMR is proximal to a telomere or centromere. The term "proximal to a telomere or centromere," as used herein in reference to a non-CpG hypomethylated DMR, means within about 10%, preferably about 5%, of chromosomal length from a telomere or centromere. In some embodiments, the term refers to the non-CpG hypomethylated DMR being within less than 1%, 2%, 3%, 4%, 5%, 6%, 7%, 8% or 9%. In some embodiments, the non-CpG hypomethylated DMR is within about 10% of chromosomal length from a telomere or centromere. In other embodiments, the non-CpG hypomethylated DMR is within about 9%, 8%, 7%, 6%, 5%, 4%, 3%, 2,%, 1%, or 0.5% of chromosomal length from a telomere or centromere.

The non-CpG hypomethylated DMR may alternatively or additionally include one or more hypermethylated promoters (e.g. transcriptional start sites). The hypermethylated promoters are promoters within the hiPSC genome that are methylated at a level less (e.g. on average) than the level of methylation of the corresponding promoter of an embryonic stem cell. The hypermethylated promoter may be one or more of the regions identified in Table 4. In Table 4 the regions included in a hypermethylated promoter are identified by a sequence reference number (i.e. RefSeq; e.g. NM_020828). A person of skill in the art would immediately recognize that each sequence reference number is a reference to a nucleotide sequence listed in the publicly available data base of the National Center for Biotechnology Information (NCBI). Therefore, the sequence reference number is a sequence identifier for a nucleotide sequences included in the hypermethylated promoters provided herein. In some embodiments, the hypermethylated promoters include the nucleotide sequence of SEQ ID NO:1, SEQ ID NO:2, SEQ ID NO:3, SEQ ID NO:4, SEQ ID NO:5 or SEQ ID NO:6.

In certain embodiments, the non-CpG hypomethylated DMR includes one or more transcriptionally repressed genes. The transcriptionally repressed genes are genes within the hiPSC genome that are transcribed at a level less (e.g. on average) than the level of transcription of the corresponding genes of an embryonic stem cell.

The non-CpG hypomethylated DMR may alternatively or additionally substantially overlap with a partially methylated domain of an origin cell of the human induced pluripotent stem cell. Where the non-CpG hypomethylated DMR substantially overlaps with a partially methylated domain of an origin cell of the human induced pluripotent stem cell, the non-CpG hypomethylated DMR of the iPSC overlaps with a domain that was partially methylated in the origin cell prior to reprogramming the origin cell to a iPSC. In some embodiments, the partially methylated domain of an origin cell is hypomethylated. In other embodiments, the partially methylated domain of an origin cell is hypermethylated. In other embodiments, the non-CpG hypomethylated DMR is the partially methylated domain of an origin cell of the human induced pluripotent stem cell. Where the non-CpG hypomethylated DMR substantially overlaps with a partially methylated domain of an origin cell of the human induced pluripotent stem cell, the non-CpG hypomethylated DMR includes at least 10% of the partially methylated domain of an origin cell. In some embodiments, the non-CpG hypomethylated DMR includes between 10% to 100% of the partially methylated domain of an origin cell. In other embodiments, the non-CpG hypomethylated DMR includes between 20% to 100%, 25% to 100%, 30% to 100%, 35% to 100%, 40% to 100%, 45% to 100%, 50% to 100%, 55% to 100%, 60% to 100%, 65% to 100%, 70% to 100%, 75% to 100%, 80% to 100%, 85% to 100%, 90% to 100%, or 95% to 100% of the partially methylated domain of an origin cell. An "origin cell" refers to the cell from which the hiPSC is derived (e.g. reprogrammed). Thus, origin cells are non-pluripotent cells, which are either partially or completely differentiated.

In some embodiments, the non-CpG hypomethylated DMR is proximal to a telomere or centromere, includes one or more hypermethylated promoters, includes one or more transcriptionally repressed genes or substantially overlaps with a partially methylated domain of an origin cell of the human induced pluripotent stem cell. In other embodiments, the non-CpG hypomethylated DMR is proximal to a telomere or centromere, include one or more hypermethylated promoters, includes one or more transcriptionally repressed genes and substantially overlaps with a partially methylated domain of an origin cell of the human induced pluripotent stem cell.

In some embodiments, the non-CpG hypomethylated DMR is spatially concordant with a H3K9me3 heterochromatin modification. The term "H3K9me3" refers to a histone 3 having three methyl groups covalently attached to the lysine at postion 9. H3K9me3 is a histone modification characteristic of heterochromatin (i.e. transcriptionally repressed chromatin). The term "spatially concordant" means the H3K9me3 heterochromatin modification is sufficiently proximal to the non-CpG hypomethylated DMR to result in a functional change within the non-CpG hypomethylated DMR. FIG. 5 depicts examples of H3K9me3 heterochromatin modifications included in non-CpG hypomethylated DMRs.

The method may further include identifying one or more CG-DMRs within the hiPSC. A CG DMR is typically about 100 to 4000 kb in length. In some embodiments, the CG-DMR includes from about 100 kb to about 5000 kb. In other embodiments, the CG-DMR includes from about 200 kb to about 5000 kb, 300 kb to about 5000 kb, from about 400 kb to about 5000 kb, 500 kb to about 5000 kb, from about 600 kb to about 5000 kb, 700 kb to about 5000 kb, from about 800 kb to about 5000 kb, 900 kb to about 5000 kb, from about 1000 kb to about 5000 kb, 1100 kb to about 5000 kb, from about 1200 kb to about 5000 kb, 1300 kb to about 5000 kb, from about 1400 kb to about 5000 kb, 1500 kb to about 5000 kb, from about 1600 kb to about 5000 kb, 1700 kb to about 5000 kb, from about 1800 kb to about 5000 kb, 1900 kb to about 5000 kb, from about 2000 kb to about 5000 kb, 2100 kb to about 5000 kb, from about 2200 kb to about 5000 kb, 2300 kb to about 5000 kb, from about 2400 kb to about 5000 kb, 2500 kb to about 5000 kb, from about 2600 kb to about 5000 kb, 2700 kb to about 5000 kb, from about 2800 kb to about 5000 kb, 2900 kb to about 5000 kb, from about 3000 kb to about 5000 kb, 3100 kb to about 5000 kb, from about 3200 kb to about 5000 kb, 3300 kb to about 5000 kb, from about 3400 kb to about 5000 kb, 3500 kb to about 5000 kb, from about 3600 kb to about 5000 kb, 3700 kb to about 5000 kb, from about 3800 kb to about 5000 kb, 3900 kb to about 5000 kb, from about 4000 kb to about 5000 kb, 4100 kb to about 5000 kb, from about 4200 kb to about 5000 kb, 4300 kb to about 5000 kb, from about 4400 kb to about 5000 kb, 4500 kb to about 5000 kb, from about 4600 kb to about 5000 kb, 4700 kb to about 5000 kb, from about 4800 kb to about 5000 kb, or 4900 kb to about 5000 kb. In some embodiments, the CG-DMR includes 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 4100, 4200, 4300, 4400, 4500, 4600, 4700, 4800, 4900, or 5000 kb. The CG-DMR may be a hypomethylated CG-DMR or a hypermethylated CG-DMR. In some embodiments, the CG-DMR is hypomethylated. The hypomethylated CG-DMR is characterized by decreased methylation relative to the methylation of a corresponding CG-DMR in a human embryonic stem cell. In some embodiments, the CG-DMR is hypermethylated. The hypermethylated CG-DMR is characterized by increased methylation relative to the methylation of a corresponding CG-DMR in a human embryonic stem cell. The comparison may be performed using the criteria outlined in the Examples section entitled "CG-DMRs" (Example 6; and see also FIG. 3). In some embodiments, the hypomethylated CG-DMR is not the nucleotide sequence of chromosome 2 starting at nucleotide position 87,905,315 ending at nucleotide position 87,906,414 and having a length of 1099 bp. Non-limiting examples of hypomethylated CG-DMRs and hypermethylated CG-DMRs are provided in Tables 1 and 2, respectively. For example, the hypermethylated CG-DMR is the nucleotide sequence of chromosome 12 starting at nucleotide position 125,033,730 ending at nucleotide position 125,034,829 and having a length of 1099 bp. The chromosomes as referred to herein are human chromosomes listed under human genome annotation 18 (i.e. hg18 annotation). Therefore, the sequence for each chromosome disclosed herein can be identified by accessing the public UCSC Human Browser Gateway database under hg18 annotation or NCBI36/hg18. A person of ordinary skill in the art will immediately be able to identify the individual nucleotide sequences provided herein by accessing the UCSC Human Browser Gateway database.

In some embodiments of the aspects above, the identifying is indicative of an aberrantly reprogrammed human induced pluripotent stem cell. An aberrantly reprogrammed human induced pluripotent stem cell is a cell that after the process of dedifferentiation still exhibits characteristics of a non-pluripotent cell (e.g. an origin cell) and lacks certain characteristics of a pluripotent cell. The aberrantly reprogrammed human induced pluripotent stem cell may be an incompletely reprogrammed human hiPSC.

The reprogrammed hiPSC may be formed by sexual or asexual propagation of one or more parent reprogrammed human induced pluripotent stem cell.

In another aspect, provided herein is a method of identifying a human induced pluripotent stem cell (hiPSC). The method includes identifying a hypomethylated CG-DMR or a hypermethylated CG-DMR within the human induced pluripotent stem cell. The human induced pluripotent stem cell may be an incompletely reprogrammed hiPSC. In some embodiments, the hypomethylated CG-DMR is characterized by decreased methylation relative to the methylation of a corresponding CG-DMR of a human embryonic stem cell. The hypermethylated CG-DMR is characterized by increased methylation relative to the methylation of a corresponding CG-DMR of a human embryonic stem cell. The comparison may be performed using the criteria outlined in the Examples section entitled "CG-DMRs" (Example 5; and see also FIG. 3). In some embodiments, the hypomethylated CG-DMR is not the nucleotide sequence of chromosome 2 starting at nucleotide position 87,905,315 ending at nucleotide position 87,906,414 and having a length of 1099 bp. Non-limiting examples of hypomethylated CG-DMRs and hypermethylated CG-DMRs are provided in Tables 1 and 2, respectively. For example, the hypermethylated CG-DMR is the nucleotide sequence of chromosome 12 starting at nucleotide position 125,033,730 ending at nucleotide position 125,034,829 and having a length of 1099 bp. The chromosomes as referred to herein are human chromosomes listed under human genome annotation 18 (i.e. hg18 annotation). Therefore, the sequence for each chromosome disclosed herein can be identified by accessing the public UCSC Human Browser Gateway database under hg18 annotation or NCBI36/hg18. A person of ordinary skill in the art will immediately be able to identify the individual nucleotide sequences provided herein by accessing the UCSC Human Browser Gateway database.

In some embodiments, the method further includes identifying one or more non-CpG hypomethylated DMR(s). In some embodiments, the non-CpG hypomethylated DMR is one or more regions identified in Table 3A and/or Table 3B. Non limiting examples of chromosomal regions that are a non-CpG hypomethylated DMR include the nucleotide sequence of chromosome 7 from position 156,535,825 to position 158,080,000, the nucleotide sequence of chromosome 8 from position 2,161,971 to position 4,761,970, the nucleotide sequence of chromosome 10 from position 131,888,467 to position 133,321,763, or the nucleotide sequence of chromosome 22 from position 46,357,370 to position 48,540,808. The chromosomes as referred to herein are human chromosomes listed under human genome annotation 18 (i.e. hg18 annotation). Therefore, the sequence for each chromosome disclosed herein can be identified by accessing the public UCSC Human Browser Gateway database under hg18 annotation or NCBI36/hg18. A person of ordinary skill in the art will immediately be able to identify the individual nucleotide sequences provided herein by accessing the UCSC Human Browser Gateway database. In some embodiments, the non-CpG hypomethylated DMR is proximal to a telomere or centromere. The non-CpG hypomethylated DMR may alternatively or additionally include one or more hypermethylated promoters (e.g. transcriptional start sites). The hypermethylated promoter may be one or more of the regions identified in Table 4. In Table 4 the regions included in a hypermethylated promoter are identified by a sequence reference number (i.e. RefSeq; e.g. NM_020828). A person of skill in the art would immediately recognize that each sequence reference number is a reference to a nucleotide sequence listed in the publicly available data base of the National Center for Biotechnology Information (NCBI). Therefore, the sequence reference number is a sequence identifier for a nucleotide sequences included in the hypermethylated promoters provided herein. In some embodiments, the hypermethylated promoters include the nucleotide sequence of SEQ ID NO:1, SEQ ID NO:2, SEQ ID NO:3, SEQ ID NO:4, SEQ ID NO:5 or SEQ ID NO:6.

In certain embodiments, the non-CpG hypomethylated DMR includes one or more transcriptionally repressed genes. The transcriptionally repressed genes are genes within the hiPSC genome that are transcribed at a level less (e.g. on average) than the level of transcription of the corresponding genes of an embryonic stem cell. The non-CpG hypomethylated DMR may alternatively or additionally substantially overlap with a partially methylated domain of an origin cell of the human induced pluripotent stem cell. An "origin cell" refers to the cell from which the hiPSC is derived (e.g. reprogrammed). In some embodiments, the non-CpG hypomethylated DMR is spatially concordant with a H3K9me3 heterochromatin modification.

In some embodiments of the aspects above, the identifying is indicative of an aberrantly reprogrammed hiPSC.

The reprogrammed hiPSC may be formed by sexual or asexual propagation of one or more parent reprogrammed human induced pluripotent stem cell.

In another aspect, provided herein is a method of identifying a human induced pluripotent stem cell (hiPSC). The method includes identifying one or more of a hypomethylated CG-DMR, one or more of a hypermethylated CG-DMR or one more of a non-CpG hypomethylated DMR within the human induced pluripotent stem cell. In some embodiments, the method includes identifying one or more of a hypomethylated CG-DMR, one or more of a hypermethylated CG-DMR and one more of a non-CpG hypomethylated DMR within the human induced pluripotent stem cell. In some embodiments, the method includes identifying one or more of a hypomethylated CG-DMR and one or more of a hypermethylated CG-DMR within the human induced pluripotent stem cell. In other embodiments, the method includes identifying one or more of a hypomethylated CG-DMR and one or more of a non-CpG hypomethylated DMR within the human induced pluripotent stem cell. In other embodiments, the method includes identifying one or more of a hypermethylated CG-DMR and one or more of a non-CpG hypomethylated DMR within the human induced pluripotent stem cell. The hypomethylated CG-DMR, a hypermethylated CG-DMR or a non-CpG hypomethylated DMR may be one or more of the regions set forth in Table 1, Table 2, Table 3A, Table 3B and Table 4. The characteristics of the hypomethylated CG-DMR, the hypermethylated CG-DMR and the non-CpG hypomethylated DMR set forth in the aspects above are equally applicable to this aspect.

In another aspect, a method of identifying a human induced pluripotent stem cell is provided. The method includes determining a methylation pattern of at least a portion of a subject cell and comparing the methylation pattern to a human embryonic stem cell methylation pattern. A difference in methylation pattern is indicative of the subject cell being a human induced pluripotent stem cell. The human induced pluripotent stem cell may be an incompletely reprogrammed induced pluripotent stem cell.

In some embodiments, the methylation pattern of the portion of the subject cell includes a non-CpG hypomethylated DMR. In some embodiments, the non-CpG hypomethylated DMR is proximal to a telomere or centromer. In other embodiments, the non-CpG hypomethylated DMR includes one or more hypermethylated promoters. In other embodiments, the non-CpG hypomethylated DMR substantially overlaps with a partially methylated domain of a non-pluripotent cell. In other embodiments, the non-CpG hypomethylated DMR includes one or more transcriptionally repressed genes. In other embodiments, the non-CpG hypomethylated DMR is spatially concordant with a H3K9me3 heterochromatin modification. The characteristics of the non-CpG hypomethylated DMR set forth in the aspects above are equally applicable to this aspect.

In other embodiments, the methylation pattern of the portion of the subject cell includes a CG-DMR within said subject cell. In some embodiments, the CG-DMR is a hypomethylated CG-DMR. In other embodiments, the CG-DMR is a hypermethylated CG-DMR. The characteristics of the CG-DMR set forth in the aspects above are equally applicable to this aspect.

In some embodiments, the methylation pattern of the portion of the subject cell includes a non-CpG hypomethylated DMR and a CG-DMR within the subject cell. In some embodiments, the non-CpG hypomethylated DMR is proximal to a telomere or centromer. In other embodiments, the non-CpG hypomethylated DMR includes one or more hypermethylated promoters. In other embodiments, the non-CpG hypomethylated DMR substantially overlaps with a partially methylated domain of a non-pluripotent cell. In other embodiments, the non-CpG hypomethylated DMR comprises one or more transcriptionally repressed genes. In other embodiments, the non-CpG hypomethylated DMR is spatially concordant with a H3K9me3 heterochromatin modification. In some embodiments, the CG-DMR is a hypomethylated CG-DMR. In other embodiments, the CG-DMR is a hypermethylated CG-DMR.

In other embodiments, the methylation pattern of the portion of the subject cell includes a plurality of non-CpG hypomethylated DMRs and a plurality of CG-DMRs within the subject cell. In some embodiments, the plurality of non-CpG hypomethylated DMRs is proximal to a telomere or centromer. In other embodiments, the plurality of non-CpG hypomethylated DMRs includes one or more hypermethylated promoters. In other embodiments, the plurality of non-CpG hypomethylated DMRs substantially overlaps with a plurality of partially methylated domains of a non-pluripotent cell. In other embodiments, the plurality of non-CpG hypomethylated DMRs comprises one or more transcriptionally repressed genes. In other embodiments, the plurality of non-CpG hypomethylated DMRs is spatially concordant with H3K9me3 heterochromatin modifications. In some embodiments, the plurality of CG-DMR is a plurality of hypomethylated CG-DMRs. In other embodiments, the plurality of CG-DMRs is a plurality of hypermethylated CG-DMRs.

In some embodiments, the difference in methylation pattern is indicative of the subject cell being an aberrantly reprogrammed human induced pluripotent stem cell.

In some embodiments, the subject cell is formed by sexual or asexual propagation of one or more parent reprogrammed human induced pluripotent stem cells.

III. TABLES

TABLE 1

CG-DMRs hypermethylated in every iPSC line with respect to all ESC lines.

| chromosome | start coordinate | end coordinate | length (base pairs) |
|---|---|---|---|
| chr12 | 125033730 | 125034829 | 1099 |
| chr12 | 128952730 | 128955529 | 2799 |
| chr12 | 129064330 | 129065329 | 999 |
| chr12 | 129092430 | 129093429 | 999 |
| chr12 | 129209230 | 129215029 | 5799 |
| chr2 | 87905315 | 87906414 | 1099 |
| chr10 | 132998500 | 133001399 | 2899 |
| chr7 | 157173784 | 157180183 | 6399 |
| chr22 | 47143596 | 47145195 | 1599 |
| chr22 | 47263296 | 47266095 | 2799 |
| chr22 | 47349296 | 47351495 | 2199 |

TABLE 2

CG-DMRs hypomethylated in every iPSC line with respect to all ESC lines.

| chromosome | start coordinate | end coordinate | length (base pairs) |
|---|---|---|---|
| chr5 | 43431922 | 43433621 | 1699 |
| chr5 | 139991422 | 139993021 | 1599 |
| chr5 | 157030122 | 157031721 | 1599 |
| chr5 | 178419622 | 178420621 | 999 |
| chr5 | 180033122 | 180034121 | 999 |
| chr5 | 180474422 | 180475421 | 999 |
| chr12 | 12831030 | 12832029 | 999 |
| chr12 | 30213930 | 30215029 | 1099 |
| chr12 | 42438130 | 42439729 | 1599 |
| chr12 | 63070030 | 63071029 | 999 |
| chr12 | 67426130 | 67427229 | 1099 |
| chr2 | 9531315 | 9533514 | 2199 |
| chr2 | 45088415 | 45089414 | 999 |
| chr2 | 85664715 | 85665714 | 999 |
| chr2 | 102233315 | 102234314 | 999 |
| chr2 | 106047815 | 106049414 | 1599 |
| chr2 | 112906715 | 112907814 | 1099 |
| chr2 | 130901715 | 130902714 | 999 |
| chr2 | 175302615 | 175303614 | 999 |
| chr2 | 201688815 | 201690414 | 1599 |
| chr2 | 201691215 | 201692214 | 999 |
| chr2 | 242391015 | 242393214 | 2199 |
| chr20 | 3589078 | 3590077 | 999 |
| chr20 | 28224978 | 28225977 | 999 |
| chr20 | 32320178 | 32321177 | 999 |
| chr20 | 61109578 | 61110577 | 999 |
| chr3 | 8784755 | 8785754 | 999 |
| chr3 | 55491955 | 55493654 | 1699 |
| chr3 | 127159355 | 127160354 | 999 |
| chr3 | 148579955 | 148581754 | 1799 |
| chr3 | 170964955 | 170966054 | 1099 |
| chr3 | 182903755 | 182905954 | 2199 |
| chr3 | 195598255 | 195600454 | 2199 |
| chr3 | 198177955 | 198179554 | 1599 |
| chr6 | 24465653 | 24466752 | 1099 |
| chr6 | 27636953 | 27637952 | 999 |
| chr6 | 27744753 | 27745752 | 999 |
| chr6 | 30001653 | 30003252 | 1599 |
| chr6 | 31383553 | 31384552 | 999 |
| chr6 | 38790453 | 38791552 | 1099 |
| chr6 | 74075453 | 74077052 | 1599 |
| chr6 | 74217453 | 74219152 | 1699 |
| chr6 | 142451253 | 142452352 | 1099 |
| chr6 | 159210253 | 159211252 | 999 |
| chr6 | 161019853 | 161020852 | 999 |
| chr6 | 168178353 | 168180052 | 1699 |
| chr1 | 20542468 | 20543467 | 999 |
| chr1 | 28781168 | 28782167 | 999 |
| chr1 | 35814868 | 35815867 | 999 |
| chr1 | 41122168 | 41123167 | 999 |
| chr1 | 146247368 | 146248967 | 1599 |
| chr1 | 149370768 | 149372967 | 2199 |
| chr1 | 153531268 | 153532267 | 999 |
| chr1 | 205884868 | 205885867 | 999 |
| chr18 | 50776889 | 50777888 | 999 |
| chr19 | 7640922 | 7642021 | 1099 |
| chr19 | 12166322 | 12167321 | 999 |
| chr19 | 13789122 | 13790121 | 999 |
| chr19 | 19512322 | 19513321 | 999 |
| chr19 | 40087422 | 40088421 | 999 |
| chr19 | 40938222 | 40940421 | 2199 |
| chr19 | 41603722 | 41604721 | 999 |
| chr19 | 43568322 | 43569921 | 1599 |
| chr19 | 54405522 | 54406521 | 999 |
| chr19 | 58252922 | 58254021 | 1099 |
| chr13 | 35768729 | 35770328 | 1599 |
| chr13 | 42046129 | 42047828 | 1699 |
| chr13 | 42495129 | 42496128 | 999 |
| chr10 | 26541100 | 26542099 | 999 |
| chr10 | 88285200 | 88286799 | 1599 |
| chr10 | 103523500 | 103524599 | 1099 |
| chr10 | 118358100 | 118359699 | 1599 |
| chr8 | 41543706 | 41544705 | 999 |
| chr8 | 104452206 | 104453805 | 1599 |
| chr8 | 105547606 | 105548605 | 999 |
| chr16 | 23673234 | 23674233 | 999 |
| chr16 | 53919734 | 53923833 | 4099 |
| chr16 | 73291534 | 73292633 | 1099 |
| chr9 | 25667166 | 25668765 | 1599 |
| chr9 | 44057866 | 44059465 | 1599 |
| chr9 | 124018866 | 124019965 | 1099 |
| chr21 | 33320749 | 33324748 | 3999 |
| chr21 | 33327349 | 33328348 | 999 |
| chr21 | 41719549 | 41721148 | 1599 |
| chr7 | 1065684 | 1066683 | 999 |
| chr7 | 12117384 | 12118383 | 999 |
| chr7 | 24289984 | 24291583 | 1599 |
| chr7 | 63660384 | 63661383 | 999 |
| chr7 | 63985984 | 63987583 | 1599 |
| chr7 | 94863384 | 94864383 | 999 |
| chr7 | 121729084 | 121730083 | 999 |
| chr7 | 154976384 | 154977383 | 999 |
| chr11 | 14882973 | 14884572 | 1599 |
| chr11 | 15051373 | 15052972 | 1599 |
| chr11 | 20574673 | 20576872 | 2199 |
| chr11 | 87880973 | 87882572 | 1599 |
| chr11 | 92341873 | 92342872 | 999 |
| chr14 | 69107954 | 69108953 | 999 |
| chr14 | 73105454 | 73107053 | 1599 |
| chr14 | 73128054 | 73129053 | 999 |
| chr14 | 96128254 | 96129853 | 1599 |
| chr14 | 101623754 | 101624753 | 999 |
| chr15 | 29520144 | 29521143 | 999 |
| chr15 | 46270644 | 46271743 | 1099 |
| chr15 | 76343644 | 76344643 | 999 |
| chr15 | 87722544 | 87723543 | 999 |
| chr4 | 6297864 | 6298863 | 999 |
| chr4 | 15313564 | 15314663 | 1099 |
| chr4 | 39124964 | 39126063 | 1099 |
| chr4 | 75082564 | 75083563 | 999 |
| chr4 | 104859864 | 104861463 | 1599 |
| chr17 | 23735290 | 23736289 | 999 |
| chr17 | 34128990 | 34130589 | 1599 |
| chr17 | 42756490 | 42757589 | 1099 |
| chr17 | 43973690 | 43974689 | 999 |
| chr17 | 69864190 | 69865789 | 1599 |

TABLE 2-continued

CG-DMRs hypomethylated in every iPSC line with respect to all ESC lines.

| chromosome | start coordinate | end coordinate | length (base pairs) |
|---|---|---|---|
| chr17 | 77224990 | 77225989 | 999 |
| chr22 | 30928396 | 30930595 | 2199 |
| chr22 | 49047896 | 49048895 | 999 |

TABLE 3A

Non-CG DMRs.

| H1 mCH > ADS-iPSC mCH Chromosome | Start | End | Length (bp) | Number of iPSC lines in which the mega-DMR is hypo-methylated (iPSC-mCH level/ ESC-mCH level < 0.7) vs H1 | vs H1 and H9 average |
|---|---|---|---|---|---|
| 1 | 4,099,596 | 5,616,921 | 1,517,325 | 4 | 4 |
| 2 | 4,563,747 | 4,863,746 | 299,999 | 3 | 1 |
| 5 | 2,241,348 | 4,916,347 | 2,674,999 | 3 | 3 |
| 7 | 152,535,825 | 154,331,422 | 1,795,597 | 5 | 4 |
| 7 | 156,920,000 | 158,080,000 | 1,160,000 | 5 | 5 |
| 8 | 2,161,971 | 4,761,970 | 2,599,999 | 5 | 4 |
| 8 | 138,614,971 | 139,764,970 | 1,149,999 | 4 | 4 |
| 10 | 131,888,467 | 133,321,763 | 1,433,296 | 5 | 4 |
| 11 | 49,075,540 | 49,509,006 | 433,466 | 4 | 2 |
| 12 | 124,710,587 | 129,485,586 | 4,774,999 | 4 | 3 |
| 15 | 18,702,374 | 19,470,373 | 767,999 | 4 | 3 |
| 16 | 5,572,321 | 7,447,320 | 1,874,999 | 4 | 3 |
| 16 | 7,950,000 | 8,550,000 | 600,000 | 4 | 3 |
| 17 | 10,700,552 | 11,750,000 | 1,049,448 | 3 | 3 |
| 17 | 21,459,552 | 21,762,057 | 302,505 | 1 | 1 |
| 19 | 21,499,279 | 21,701,289 | 202,010 | 3 | 1 |
| 19 | 61,638,290 | 61,788,289 | 149,999 | 2 | 2 |
| 20 | 39,879,269 | 41,504,268 | 1,624,999 | 4 | 4 |
| 20 | 52,720,000 | 53,804,268 | 1,084,268 | 5 | 3 |
| 21 | 40,220,292 | 41,420,291 | 1,199,999 | 4 | 4 |
| 22 | 15,615,370 | 15,790,369 | 174,999 | 3 | 2 |
| 22 | 46,357,370 | 48,540,808 | 2,183,438 | 5 | 5 |

TABLE 3B

Non-CG DMRs.

| ADS-iPSC mCH > H1 mCH Chromosome | Start | End | Length (bp) | Number of iPSC lines in which the mega-DMR is hypermethylated (ESC-mCH level/ iPSC-mCH level < 0.7) vs H1 | vs H1 and H9 average |
|---|---|---|---|---|---|
| 1 | 49,378,922 | 50,178,921 | 799,999 | 3 | 3 |
| 1 | 150,437,596 | 151,071,921 | 634,325 | 2 | 3 |
| 8 | 48,040,201 | 48,260,970 | 220,769 | 4 | 4 |
| 10 | 37,302,467 | 37,715,763 | 413,296 | 5 | 5 |
| 18 | 14,177,036 | 14,939,475 | 762,439 | 4 | 4 |
| 19 | 48,008,279 | 48,397,289 | 389,010 | 2 | 3 |
| 21 | 14,120,292 | 14,279,213 | 158,921 | 5 | 5 |

TABLE 4

Hypermethylated Promoter Regions.

| RefSeq | Gene symbol | H1 RPKM | ADS-iPS RPKM | Hypermethylated TSS in ADS-iPSC | Hypermethylated TSS in all iPSC lines |
|---|---|---|---|---|---|
| NM_018836 | AJAP1 | 0.449 | 0.15 | + | − |
| NM_001134222 | IRX2 | 22.1 | 2.44 | + | − |
| NM_033267 | IRX2 | 18.8 | 2.43 | + | − |
| NM_178569 | C5orf38 | 1.6 | 0.134 | + | − |
| NM_024337 | IRX1 | 2.58 | 0.57 | + | − |
| NM_001039350 | DPP6 | 0.362 | 0.001 | − | − |
| NM_130797 | DPP6 | 0.00279 | 0.001 | + | − |
| NM_001936 | DPP6 | 0.457 | 0.001 | + | − |
| NM_130843 | PTPRN2 | 0.871 | 0.147 | − | − |
| NM_002847 | PTPRN2 | 0.416 | 0.0667 | − | − |
| NM_015912 | FAM135B | 0.0524 | 0.00187 | + | − |
| NM_174937 | TCERG1L | 1.28 | 0.0481 | + | + |
| NM_001136103 | TMEM132C | 0.14 | 0.001 | − | − |
| NM_145648 | SLC15A4 | 5.18 | 2.31 | + | − |
| NM_144669 | GLT1D1 | 2.08 | 0.0544 | + | − |
| NM_133448 | TMEM132D | 1.94 | 0.0253 | + | + |
| NM_007197 | FZD10 | 0.138 | 0.0113 | + | + |
| NM_004764 | PIWIL1 | 0.00903 | 0.001 | − | − |
| NM_018723 | A2BP1 | 0.0184 | 0.00119 | + | − |
| NM_001142333 | A2BP1 | 0.0204 | 0.00119 | + | − |
| NM_145891 | A2BP1 | 0.0704 | 0.0016 | − | − |

TABLE 4-continued

Hypermethylated Promoter Regions.

| RefSeq | Gene symbol | H1 RPKM | ADS-iPS RPKM | Hypermethylated TSS in ADS-iPSC | Hypermethylated TSS in all iPSC lines |
|---|---|---|---|---|---|
| NM_001001415 | ZNF429 | 5.58 | 0.967 | − | − |
| NM_173531 | ZNF100 | 2.45 | 0.654 | − | − |
| NM_022103 | ZNF667 | 4.7 | 0.843 | − | − |
| NM_020813 | ZNF471 | 0.745 | 0.107 | − | − |
| NM_020828 | ZFP28 | 2.92 | 0.48 | + | + |
| NM_001001668 | ZNF470 | 2.62 | 0.999 | + | − |
| NM_133170 | PTPRT | 0.0526 | 0.00158 | + | − |
| NM_007050 | PTPRT | 0.0806 | 0.00168 | + | − |
| NM_006198 | PCP4 | 0.603 | 0.0177 | − | − |
| NM_175878 | XKR3 | 0.0863 | 0.001 | − | − |
| NM_001082967 | FAM19A5 | 3.05 | 0.001 | + | + |
| NM_015381 | FAM19A5 | 0.669 | 0.001 | + | + |
| NM_004476 | FOLH1 | 0.00192 | 0.0216 | − | − |
| NM_001014986 | FOLH1 | 0.00218 | 0.0249 | − | − |
| NM_015347 | RIMBP2 | 0.0226 | 0.106 | − | − |
| NM_004662 | DNAH9 | 0.001 | 0.0112 | − | − |
| NM_001389 | DSCAM | 0.0145 | 0.0392 | + | − |

RefSeq genes displaying ≥2-fold difference in transcript abundance between H1 and ADS-iPSC, located within non-CG mega-DMRs that are hypomethylated in iPSC lines relative to ESCs.
Abbreviations:
TSS, transcriptional start site;
RPKM, reads per kilobase of transcript per million reads.

IV. EXAMPLES

Example 1

Similar Global DNA Methylome Characteristics of ESCs and iPSCs

In order to assess the degree to which a somatic cell DNA methylome is reprogrammed into an ESC-like state by induction of a pluripotent state, Applicants generated comprehensive, single base resolution DNA methylomes of a range of cell types using the shotgun bisulfite-sequencing method, MethylC-Seq (Lister, R. et al. *Nature* 462:315-322 (2009). Our central focus was a high-efficiency, feeder-free reprogramming system (Sugii, S. et al. *Proceedings of the National Academy of Sciences* (2010)), in which female adipose-derived mesenchymal stem cells (ADS) were reprogrammed into a pluripotent state by retroviral transformation with the OCT4, SOX2, KLF4 and c-MYC genes (ADS-iPSC). The ADS-iPSCs expressed pluripotency-related marker genes, differentiated into all three embryonic germ layers in vitro, and were able to form multilineage teratomas (Sugii, S. et al. *Proceedings of the National Academy of Sciences* (2010)), thereby satisfying the criteria for pluripotency in human cells (Daley, G. et al. *Cell Stem Cell* 4:200-1; author reply 202 (2009)). Additionally, Applicants analyzed the DNA methylome of adipocytes derived from the ADS cells (ADS-adipose) through adipogenic differentiation conditions. For these cell lines Applicants generated high coverage whole-genome methylomes, using between 549-633 million uniquely mapped, non-clonal, paired-end sequencing reads (71.1-80.6 Gb) to provide an average coverage of 11.5-13.1 X per strand of the human genome, assaying 87.6-94.5% of the cytosines in the genome (FIG. 1a, Supplementary Table 1). This is equivalent to the methylomes Applicants previously reported (Lister, R. et al. *Nature* 462:315-322 (2009)) for two human cell lines, H1 human embryonic stem cells (Thomson, J. A. et al. *Science* 282: 1145-1147 (1998)) and IMR90 fetal lung fibroblasts (Nichols, W. W. et al. *Science* 196:60-63 (1977)) that Applicants have included as ESC and somatic reference methylomes in this study. Furthermore, to explore the variation between independent iPSC lines potentially due to stochastic reprogramming events, parental somatic cell type, reprogramming technique, and laboratory-specific effects, Applicants generated full DNA methylomes for four additional iPSC lines that were isolated in an independent laboratory: an iPSC line generated by lentiviral integration of the OCT4, SOX2, NANOG and LIN28 genes into IMR90 lung fibroblasts (IMR90-iPSC) (Yu, J. et al. *Science* 318:1917-1920 (2007)), and three independent iPSC lines generated by reprogramming of foreskin fibroblasts by non-integrating episomal vectors (FF-iPSC 6.9, FF-iPSC 19.7, FF-iPSC 19.11), as described previously (Yu, J. et al. *Science* 324: 797-801 (2009)). For each additional iPSC line Applicants generated between 303-358 million uniquely mapped, non-clonal, single-end sequencing reads (25.1-29.5 Gb) to provide an average coverage of 4.1-4.8 X per strand of the human genome, assaying 75.5-81.6% of genomic cytosines (FIG. 1a, Supplementary Table 1). Browsing the methylomes at single base-resolution can be performed at http://neomorph.salk.edu/ips_methylomes using the AnnoJ browser (www.annoj.org). Together, this constitutes the first unbiased, whole-genome survey of any iPSC methylome at single-base resolution and, accordingly, enables the first analysis of variability in DNA methylation between ESC and iPSC throughout the entire genome.

Figure 1B:
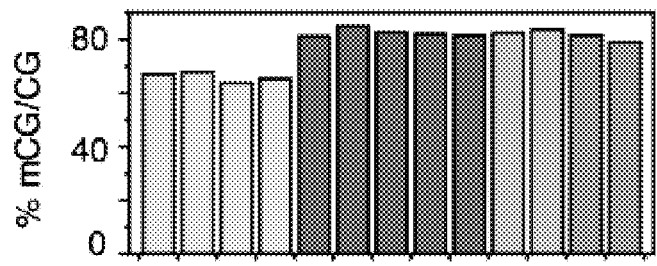
FIG. 1. Global trends of human iPSC and ESC DNA methylomes.
(FIG. 1d) AnnoJ data browser representation of the restoration of non-CG methylation in all iPSC and ESC lines.
(FIG. 1e) Dendrogram of the analyzed cell lines based on Pearson correlation of mCG or mCH levels in 1 kb windows throughout the genome.
Figure 1C:
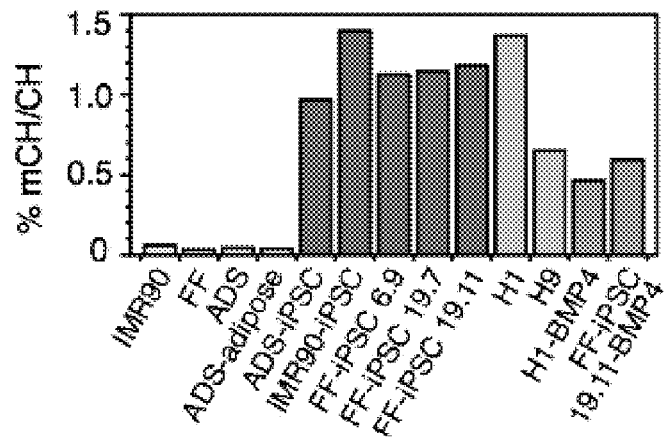
Figure 1D:
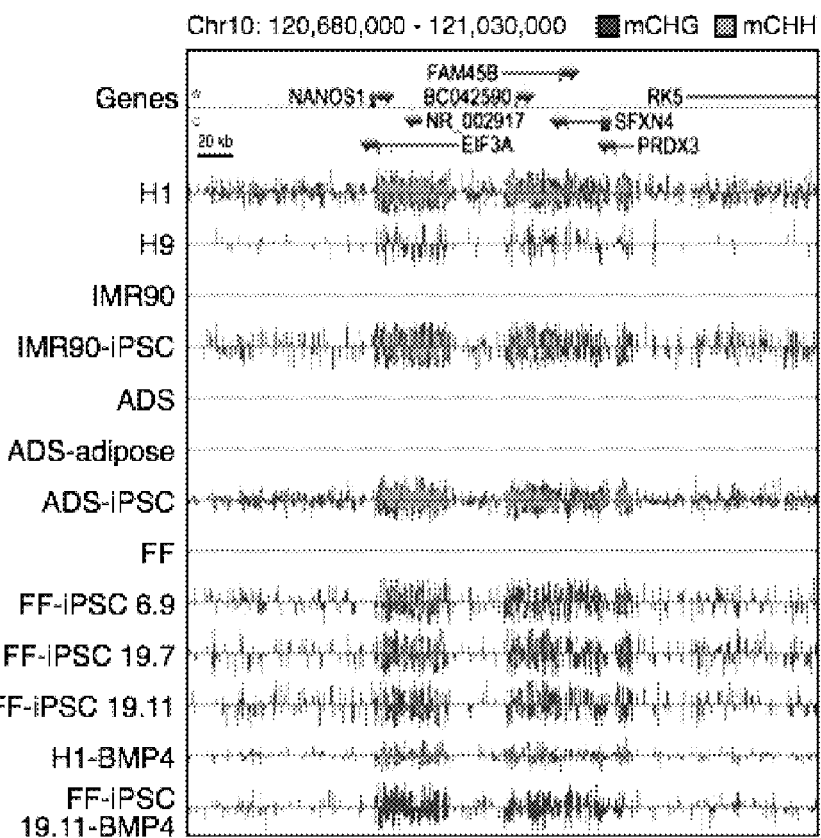
Figure 1E:
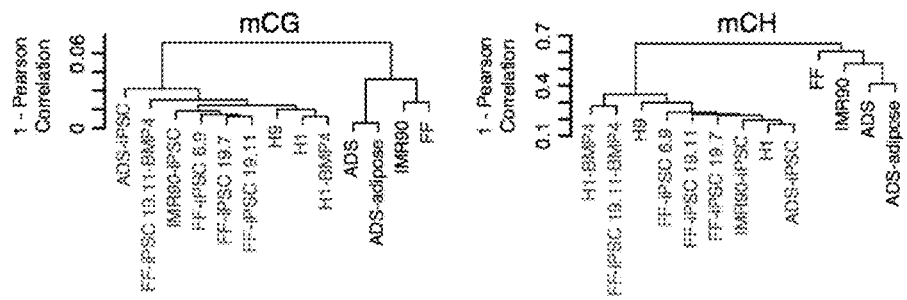

The genome-wide frequency of DNA methylation at both CG and non-CG (mCH, where H=A, C or T) sites indicated that iPSCs resemble ESCs and are distinct from somatic cells. All ESC and iPSC lines were methylated at CG dinucleotides at a frequency of 81-85%, compared to 63-67% in the somatic cell lines (FIG. 1b), consistent with the global partially-methylated state previously observed in the IMR90 fibroblast genome (Lister, R. et al. *Nature* 462:315-322 (2009)). Similarly, while somatic cells contained negligible levels of cytosine methylation in the non-CG context, all pluripotent cells harbored significant mCH at a similar frequency (FIG. 1c). As observed in ESCs (Lister, R. et al. *Nature* 462:315-322 (2009)), all iPSC genomes displayed enrichment for mCH in genes (FIG. 1d). Clustering of cell lines based on either mCG or mCH levels in 10 kb windows of the genome demonstrated that on a genome-scale the DNA methylomes of ESCs and iPSCs are similar and highly distinct from somatic cells, including an adult stem cell (FIG. 1e). This relationship agrees with clustering of cell types based on transcriptional activity, as assayed by strand-specific RNA-Seq on the H1, ADS, ADS-adipose and ADS-iPSC lines (Supplementary FIG. 1). The smoothed profile of mCH density in 10 kb windows showed that on the chromosomal level the density profile of non-CG methylation in iPSCs is highly similar to ESCs (FIG. 1f), with the notable exception of some large dissimilar regions (FIG. 1f, arrow). Analysis of DNA methylation patterns flanking enhancers and OCT4, NANOG and SOX2 protein-DNA interaction sites identified in H1 ESCs revealed that the depletion of DNA methylation at these sites in iPSC genomes and the H9 ESC genome was consistent with the depletion previously observed for H1 ESCs (Supplementary FIG. 2-5). Furthermore, very similar mCG patterns at the pluripotency-related genes OCT4/POU5F1, NANOG, UTF1 and ZFP42 were observed in all ESCs and iPSCs (Supplementary FIG. 6). Taken together, these data indicate that, on the genome-scale and at these crucial pluripotency genes, iPSC and ESC DNA methylomes closely resemble one another. Moreover, the re-methylation of the genome in the non-CG context through reprogramming of somatic cells confirms earlier suggestions that global non-CG methylation is a hallmark of the pluripotent cell state (Lister, R. et al. *Nature* 462:315-322 (2009)).

Figure 2A:
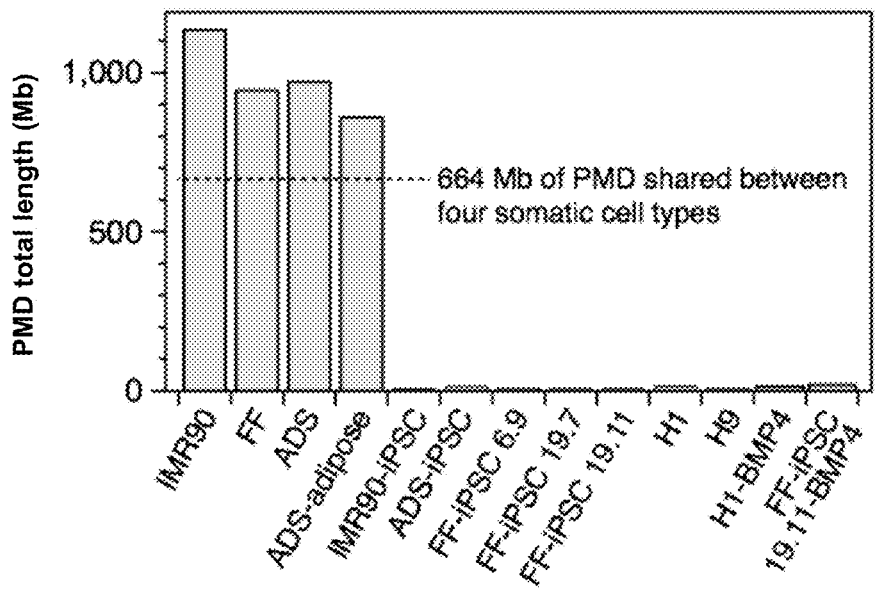
(FIG. 2a) Total length of PMDs identified in each cell line, and overlap of PMDs identified in the four somatic cell types.
Figure 2B:
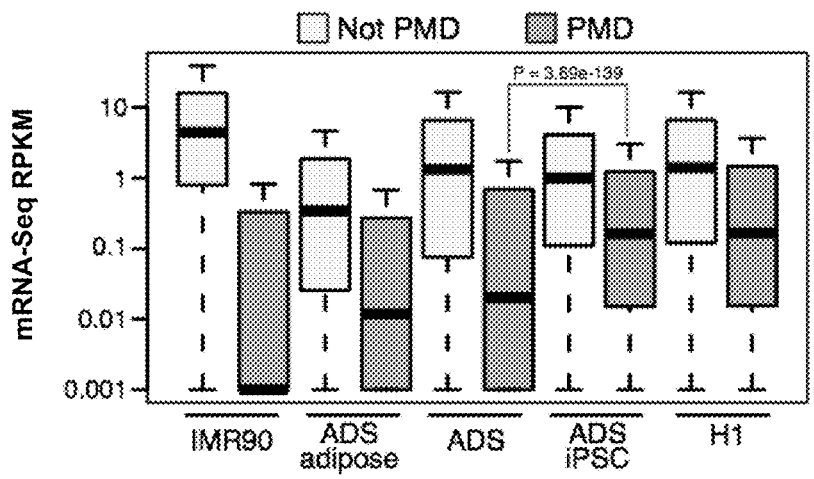
(FIG. 2b) mRNA-Seq RPKM for all RefSeq genes outside PMDs, and all RefSeq genes within genomic regions defined as PMDs. For ADS-iPS and H1 the ADS PMD genomic regions were used as PMDs. P-value is from two-tailed Wilcoxon test between ADS-PMD and ADS-iPSC-PMD. Abbreviations: PMD, partially methylated domain.
Figure 3A:
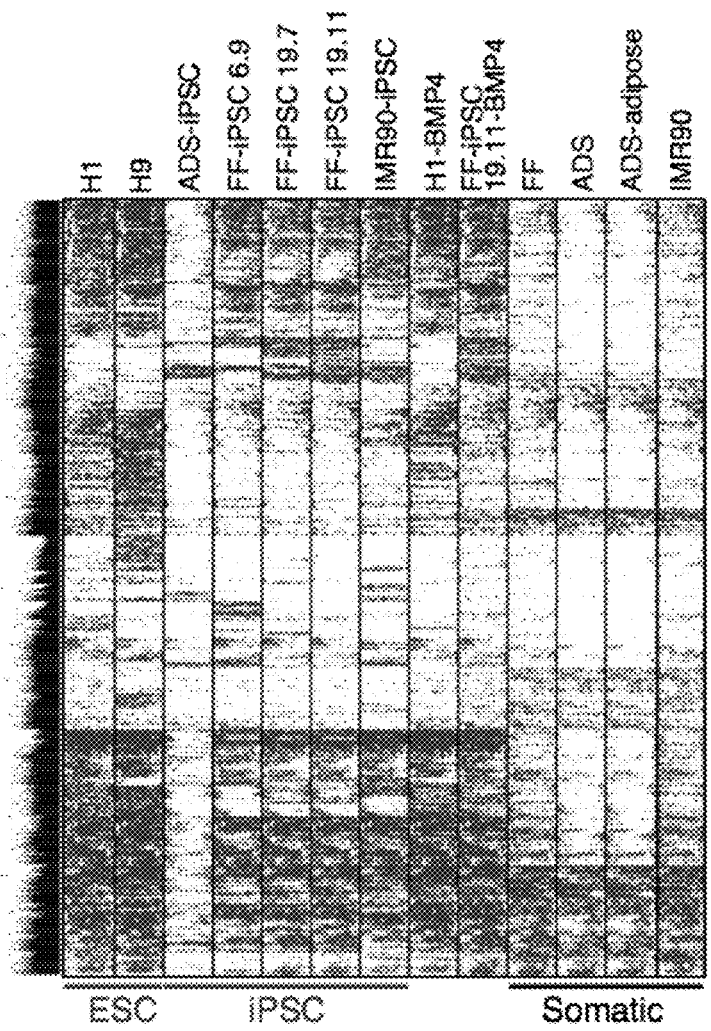
(FIG. 3a) Complete linkage hierarchical clustering of mCG density within CG-DMRs identified between all ESC and iPSC DNA methylomes. Each CG DMR was profiled over 20 equally sized bins.
Figure 3B:
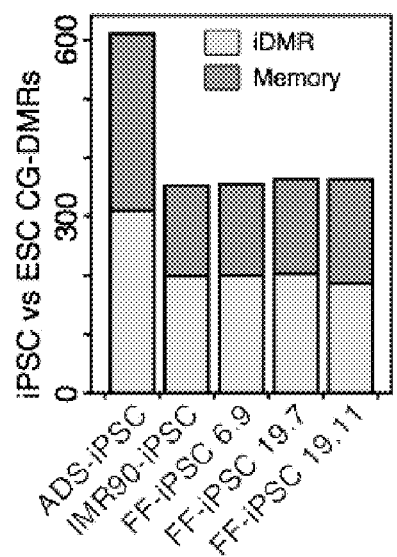
(FIG. 3b) The CG-DMRs for each iPSC line with respect to H1 and H9 ESCs were categorized as having methylation patterns like the progenitor somatic cell line (memory) or iPSC-specific (iDMR).
Figure 3C:
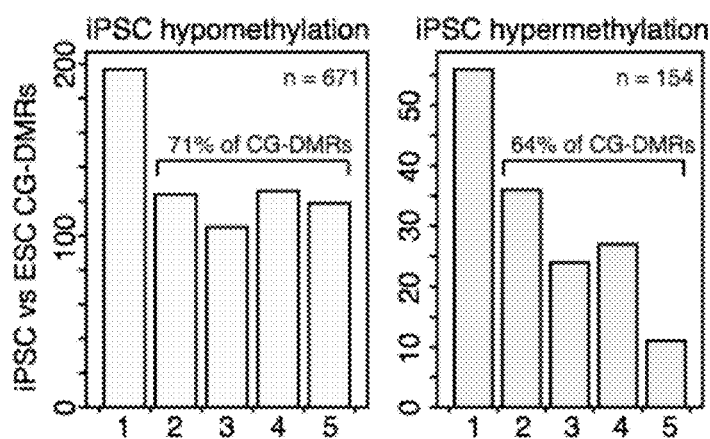
(FIG. 3c) Number of iPSC hypomethylated and hypermethylated CG-DMRs aberrant in the indicated number of iPSC lines.
Figure 3D:
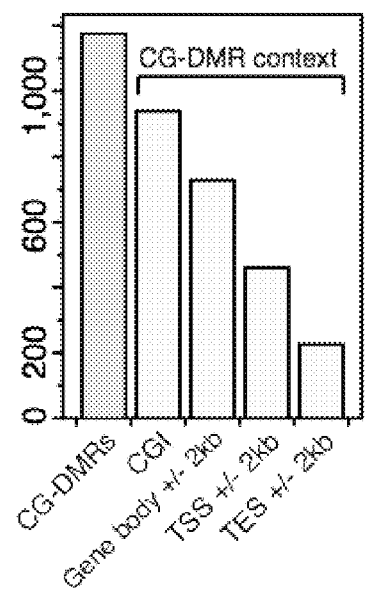
(FIG. 3d) Number of all CG-DMRs coincident with indicated genomic and genic features. Abbreviations: DMR, differentially methylated region; CGI, CG Island; TES, transcriptional end site; TSS, transcriptional start site.
Figure 7:
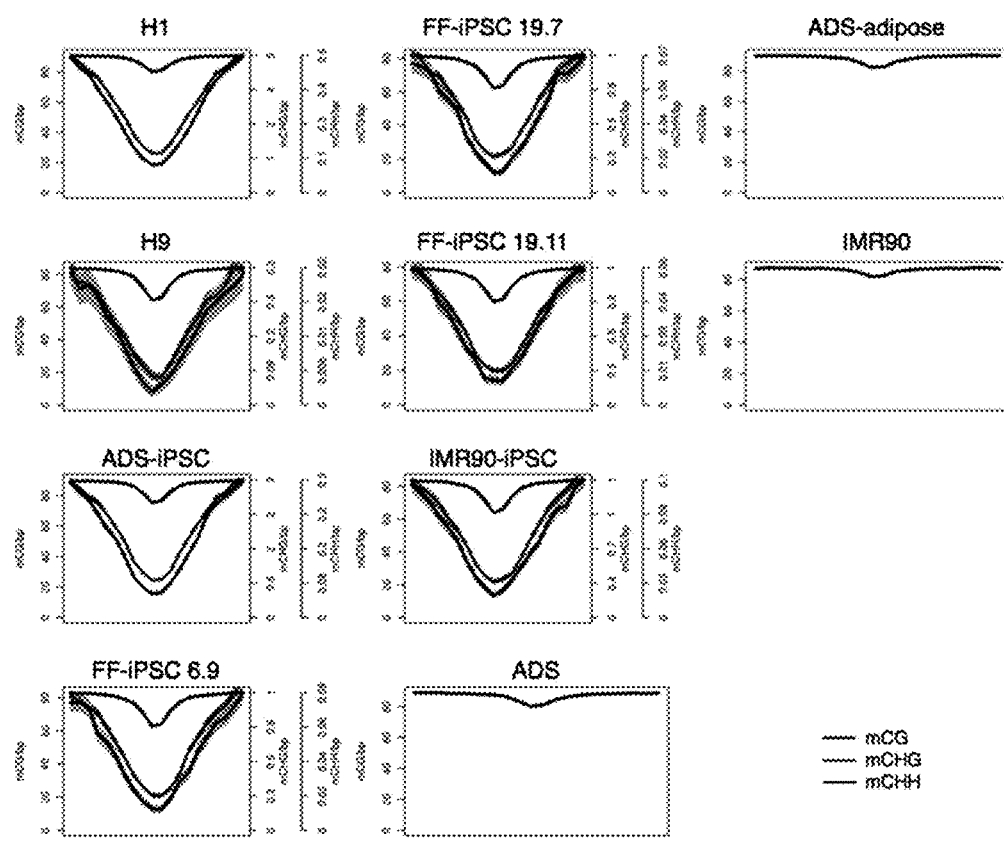
FIG. 7. Density of DNA methylation at NANOG binding sites. The average relative DNA methylation densities in each sequence context are shown from 1.5 kb upstream to 1.5 kb downstream of the predicted sites of DNA-protein interaction of NANOG identified by ChIP-seq in H1 embryonic stem cells. Shaded areas indicate the $95^{th}$ confidence interval for the mean.

Applicants previously discovered that over 40% of the genome of IMR90 fibroblasts was in a partially methylated state, with large regions of each autosome displaying lower average levels of CG methylation, termed Partially Methylated Domains (PMDs) (Lister, R. et al. *Nature* 462:315-322 (2009)). The PMDs were frequently associated with the heterochromatin modification H3K27me3 and lower transcript abundance of genes within the PMDs (Lister, R. et al. *Nature* 462:315-322 (2009)) which may indicate that the differentiated cell (IMR90) no longer requires, or is unable to maintain, high mCG levels in these regions. The DNA methylomes of the two non-pluripotent cell types Applicants have profiled here, ADS and ADS-adipose, also contain PMDs in a similar proportion of the genome to IMR90 (FIG. 2a). Moreover, the regions of the genome that are partially methylated between IMR90 and ADS are highly concordant, with 74% and 87% of the PMD bases overlapping for IMR90 and ADS, respectively (FIG. 2a). Notably, the PMDs in the ADS and IMR90 genomes were transformed to a fully methylated state in the CG context by induction of a pluripotent state (Supplementary FIG. 7); the PMD state was effectively absent from the pluripotent cell genomes (FIG. 2a). As previously observed in IMR90, the transcript abundance associated with genes located within PMDs was lower than the average for all other genes (FIG. 2b). Notably, for the genes located in ADS PMD regions, transcript abundance was over 1 order of magnitude higher in ADS-iPSC cells than ADS (Wilcoxon $P=3.7e^{-139}$), indicating that reprogramming is able to reverse the transcriptional repression associated with the PMD state, returning transcript abundance to similar levels observed in the H1 ESCs.

Example 2

Somatic Cell Memory and Aberrant Reprogramming of CG DNA Methylation

DNA methylation proximal to promoters and transcriptional start sites is generally associated with lower gene expression, and distinct cell types display abundant variable methylation patterns proximal to genes that may influence transcriptional activity (Lister, R. et al. *Nature* 462:315-322 (2009); Rakyan, V. K. et al. *Genome Res.* 18:1518-1529 (2008); Laurent, L. et al. *Genome Research* (2010)). A central question in somatic cell reprogramming is the efficacy and variability of resetting to an ESC-like state the somatic DNA methylation configurations that may affect gene activity. Although global patterns of DNA methylation in the CG context appeared very similar between ESCs and iPSCs (FIG. 1-2), a comprehensive analysis of CG DNA methylation between all ESC and iPSC lines identified 1175 differentially methylated regions (CG-DMRs) that were differentially methylated in at least one iPSC or ESC line (1% FDR, Supplementary Table 2) and in total comprised 1.68 Mb ranging from 1 to 11 kb in length. Importantly, identification of CG-DMRs between the H1 and H9 ESCs with the same criteria provided no results. A heatmap of the mCG density in the 1175 CG-DMRs allowed visualization of the variability within and between ESC and iPSC lines (FIG. 3). While mCG patterns within each category of cells (ESC, iPSC, somatic) was generally consistent and distinct from the cells in each other category, individual cell lines displayed some variability. Notably, for a subset of CG-DMRs (for example, regions indicated by the blue line in FIG. 3), ADS-iPSC was generally hypomethylated relative to the other iPSC lines, a pattern that was similarly observed between the ADS and IMR90 parental somatic cells, potentially indicating memory of the parental somatic cell DNA methylation patterns. A recent study reported the retention of somatic cell DNA methylation patterns in early-passage (4) mouse iPSCs that was sufficient to distinguish between iPSC lines derived from different progenitor cell types, and which was subsequently attenuated after further passages (10-16 total) (Polo, J. M. et al. *Nature biotechnology* (2010)). However, the iPSCs analyzed here included relatively late passage iPSC lines (15-66 passages, Supplementary Table 1), indicating that Applicants are able to discriminate somatic DNA methylation patterns in iPSCs that are resistant to resetting to an ESC-like state.

Figure 8:
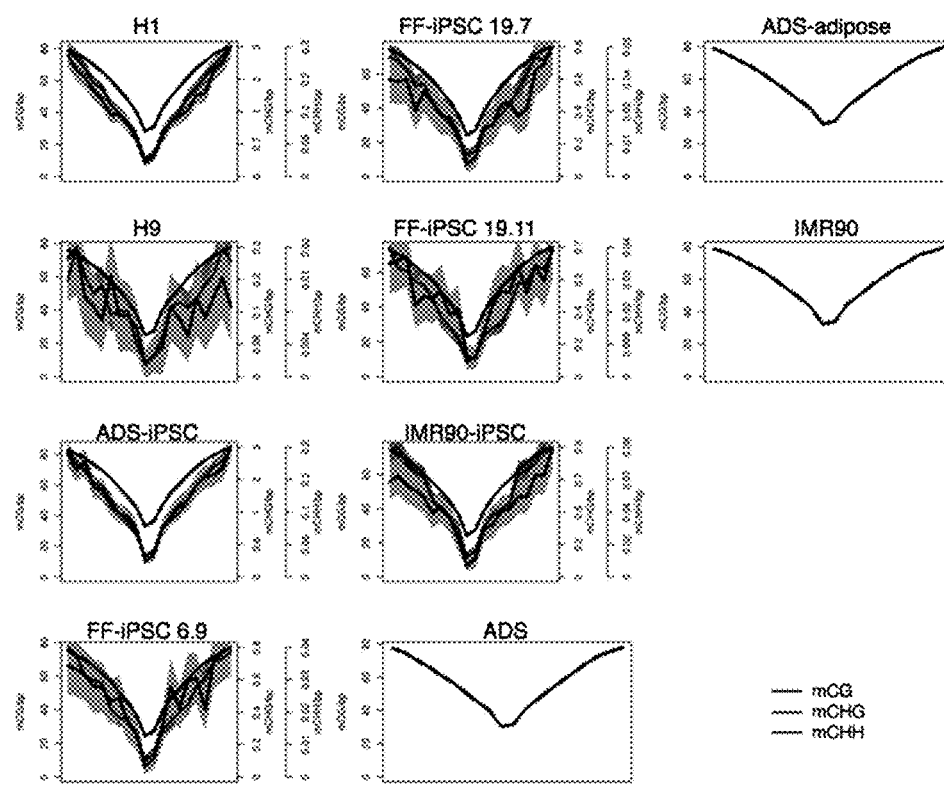
FIG. 8. Density of DNA methylation at OCT4 binding sites. The average relative DNA methylation densities in each sequence context are shown from 1.5 kb upstream to 1.5 kb downstream of the predicted sites of DNA-protein interaction of OCT4 identified by ChIP-seq in H1 embryonic stem cells. Shaded areas indicate the $95^{th}$ confidence interval for the mean.
Figure 9:
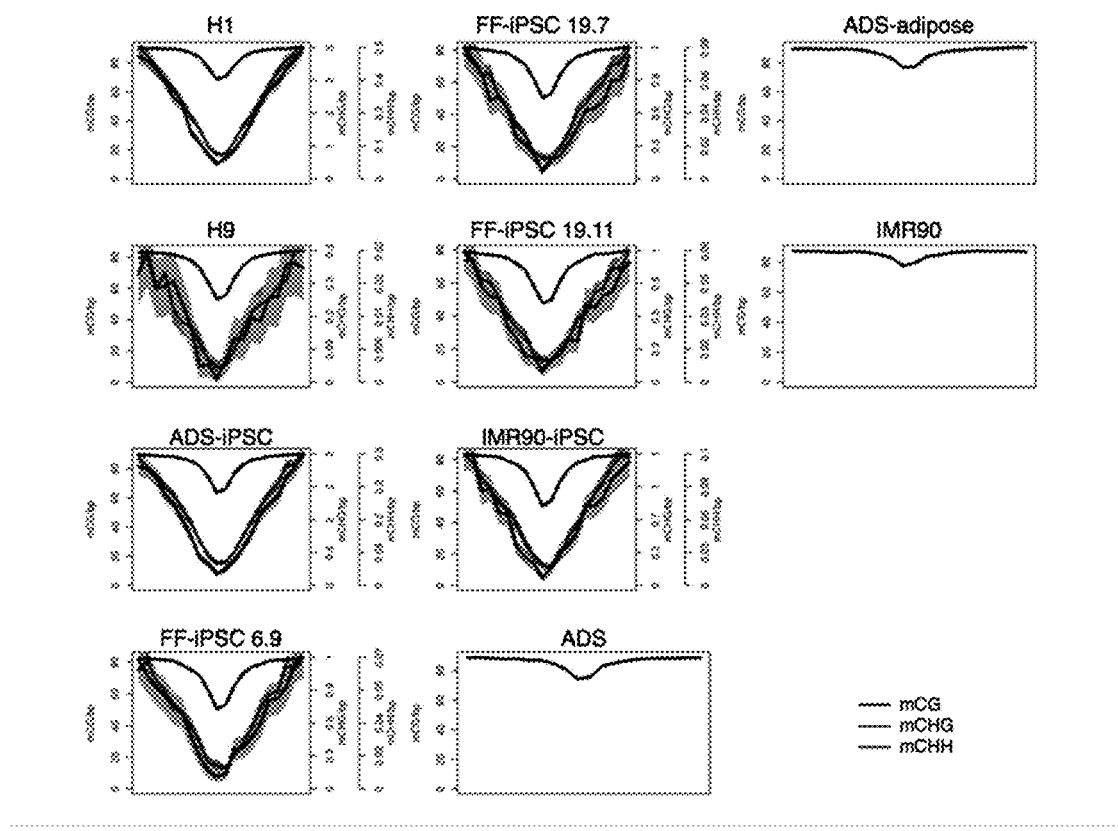
FIG. 9. Density of DNA methylation at SOX2 binding sites. The average relative DNA methylation densities in each sequence context are shown from 1.5 kb upstream to 1.5 kb downstream of the predicted sites of DNA-protein interaction of SOX2 identified by ChIP-seq in H1 embryonic stem cells. Shaded areas indicate the $95^{th}$ confidence interval for the mean.

DNA methylation at CG islands (CGIs) proximal to gene promoters and transcriptional start sites is inhibitory to transcriptional activity (Cedar, H. & Bergman, *Nat Rev Genet* 10:295-304 (2009). While demethylation of promoters that lack CGIs upon reprogramming to a pluripotent state is well established, for example at OCT4/POUF51 and NANOG (Mikkelsen, T. S. et al. *Nature* 454:49-55 (2008)), it is unknown whether highly methylated CGIs in differentiated cells can be demethylated during iPSC reprogramming. To address this issue Applicants analyzed CG-DMRs between the ESCs and somatic cells (1% FDR) that overlapped with CGIs, and the methylation state in the iPSCs at these CGIs. Of 2145 CG-DMRs coincident with CGIs (CGI-DMRs), 1337 and 309 were more than 2-fold hypermethylated in ESCs and somatic cells, respectively. Of the 309 CGI-DMRs hypermethylated in somatic cells, 82.5% were hypomethylated in the iPSCs and were similar to ESCs, 7.1% were dissimilar to both ESCs and somatic cells, and 10.4% remained hypermethylated in iPSCs (Supplementary FIG. 8). Of the 1337 CGI-DMRs hypermethylated in ESCs, 71.8% were hypermethylated akin to ESCs in the iPSCs, 13.5% were methylated at an intermediate level between ESCs and somatic cells, and 14.7% remained hypomethylated in iPSCs (Supplementary FIG. 9). Together, these results indicate that CGIs in iPSCs are predominantly reprogrammed to an ESC-like state, and in particular, hypermethylated CGIs are not especially resistant to reprogramming.

Figure 4A:
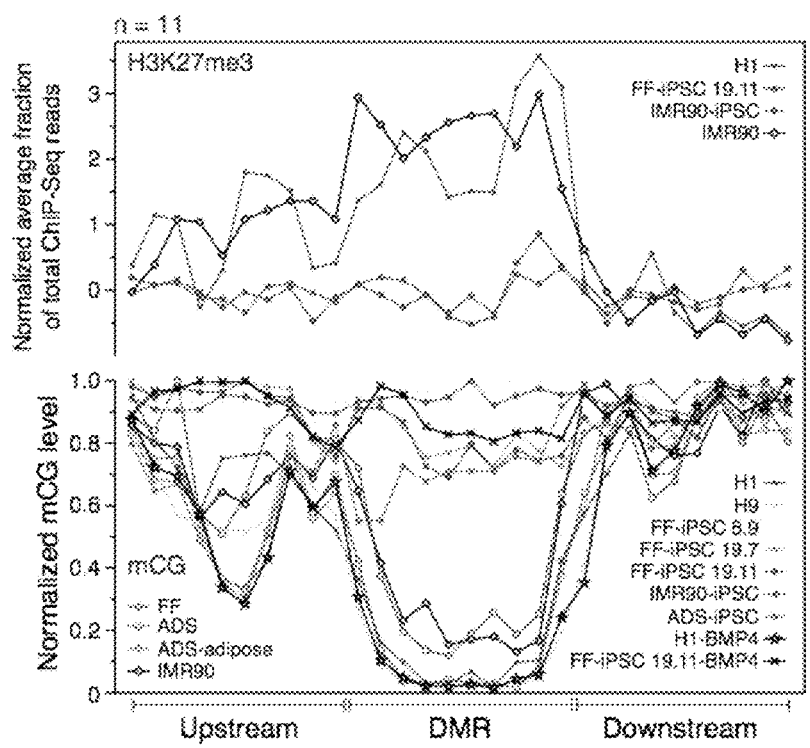
(FIG. 4a) Normalized mCG levels (lower y-axis) and normalized H3K27me3 ChIP-Seq read density (upper y-axis) over CG-DMRs hypermethylated in all iPSC lines and flanking genomic regions.

Aberrant CG methylation patterns identified between iPSCs and ESCs may be categorized as either failure to reprogram the progenitor somatic cell methylation patterns (memory, like progenitor) or inappropriate methylation found neither in the ESC nor progenitor somatic cells. Comparison of ADS-iPSC CG-DMRs to the ADS progenitor, and IMR90-iPSC CG-DMRs versus the progenitor IMR90 showed that in iPSC lines 57-60% of CG-DMRs were aberrant with respect to ESCs (P=0.01) and reflected the progenitor methylation state (FIG. 4a). Accordingly, in the iPSC lines, 40-43% of the CG-DMRs could be classified as "unlike progenitor", and 30-42% of these CG-DMRs were in common between both iPSC lines.

Figure 4B:
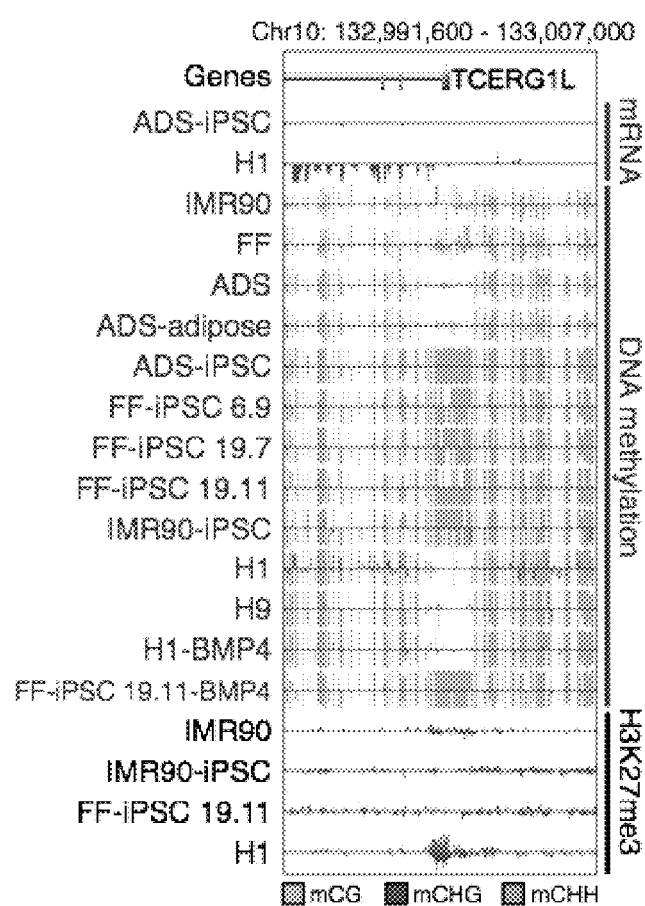
(FIG. 4b) Data browser representation of mRNA, DNA methylation and H3K27me3 density for a CG-DMR identified in all iPSC lines.
Figure 4C:
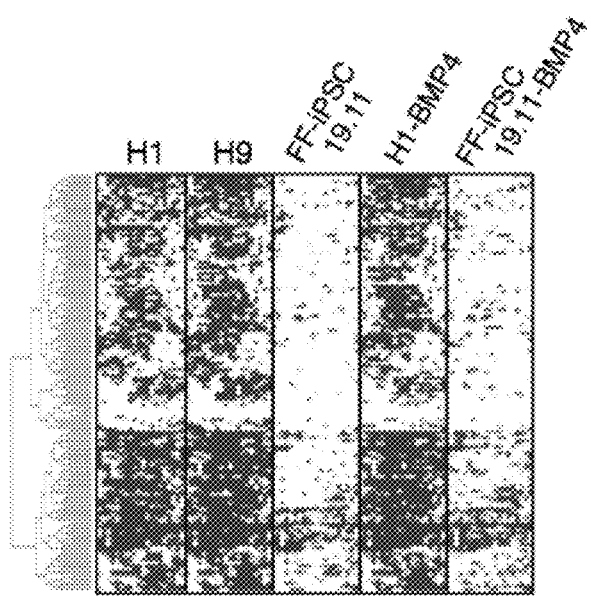
(FIG. 4c) Complete linkage hierarchical clustering of mCG density within the CG-DMRs hypomethylated in both FF-iPSC 19.11 and FF-iPSC 19.11-BMP4 relative to H1, H9 and H1-BMP4. Each CG-DMR was profiled over 20 equally sized bins.
Figure 4D:
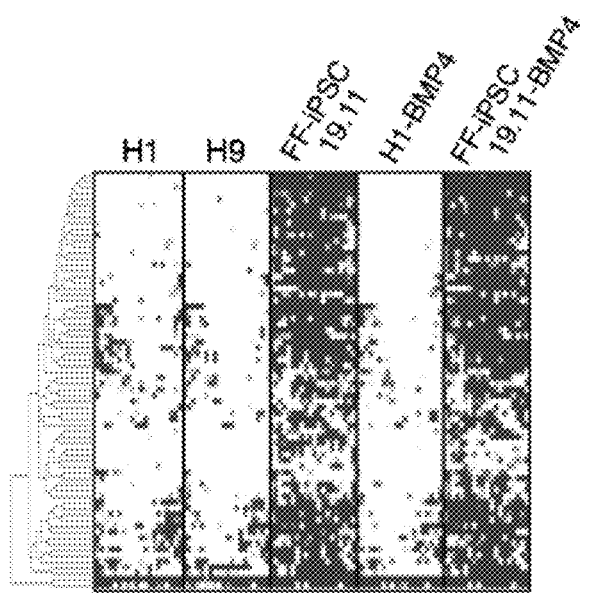
(FIG. 4d) same as c for hypermethylated CG-DMRs.
Figure 4E:
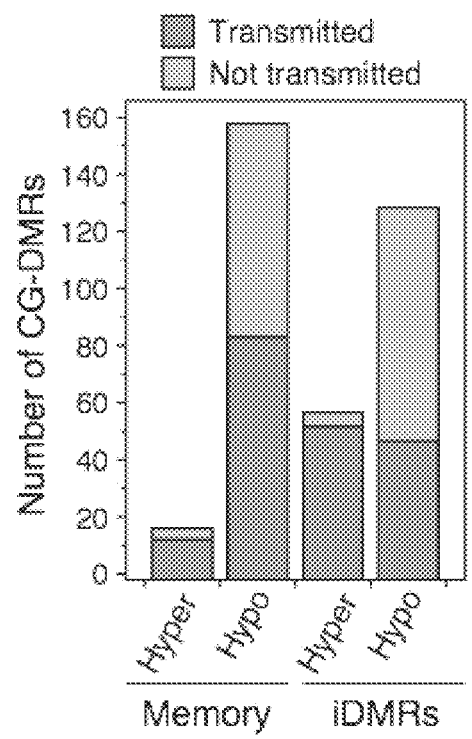
(FIG. 4e) FF-iPSC 19.11 CG-DMR transmission through differentiation to trophoblast cells. CG-DMRs were categorized by methylation state relative to the ESCs (hyper: hypermethylated, hypo: hypomethylated), similarity to somatic progenitor methylation (memory: like progenitor, iDMR: unlike progenitor), and whether the CG-DMR was present in FF-iPSC 19.11 differentiated into trophoblast cells with BMP4 (transmitted) or not (not transmitted).

Inspection of the concordance of methylation state in the five iPSC lines showed that 65% of the CG-DMRs were aberrant with respect to the ESCs in at least two iPSC lines, with 19% being confirmed in all five iPSC lines (P=0.01, FIG. 4b, Supplementary table 3). The majority of CG-DMRs (80%) occurred at CGIs, and to a lesser extent near or within genes (62%), with 29% and 19% located within 2 kb of transcriptional start and end sites, respectively (FIG. 4c). Closer inspection of the CG-DMRs confirmed in all five iPSC lines revealed that the vast majority of them (203 of 218, or 93%) were hypomethylated in the iPSC lines, suggesting that the general deficiency in resetting DNA methylation patterns during reprogramming is insufficient methylation. Notably, the remaining 15 CG-DMRs hypermethylated in the iPSC lines were also associated with the absence of the heterochromatic H3K27me3 histone modification, whereas the H1 ESC showed marked enrichment of this modification at these sites (FIG. 4d,e). The combination of these aberrant DNA methylation and histone marks at transcriptional start sites was frequently associated with transcriptional repression in the ADS-iPSC compared to H1 ESCs (FIG. 4e).

Several conclusions can be made from this catalogue of CG-DMRs. First, reprogramming a somatic cell to a pluripotent state generates hundreds of aberrantly methylated loci, predominantly at CGIs and associated with genes. Second, while insufficient reprogramming manifested as a memory of the progenitor somatic cell methylation state is common, a high incidence of CG-DMRs that were unlike both the progenitor somatic cell and ESCs indicates that aberrant methylation patterns dissimilar to both the start and endpoints of the reprogramming process are frequently generated. Third, while there is variability in the loci that are differentially methylated between iPSC lines, a high proportion of CG-DMRs are found in multiple independent iPSC lines, indicating that these regions have a strong propensity to be insufficiently or aberrantly reprogrammed. Fourth, a core set of CG-DMRs was present in every iPSC line, representing hotspots of aberrant epigenomic reprogramming common to iPSCs.

Example 3

Figure 5A:
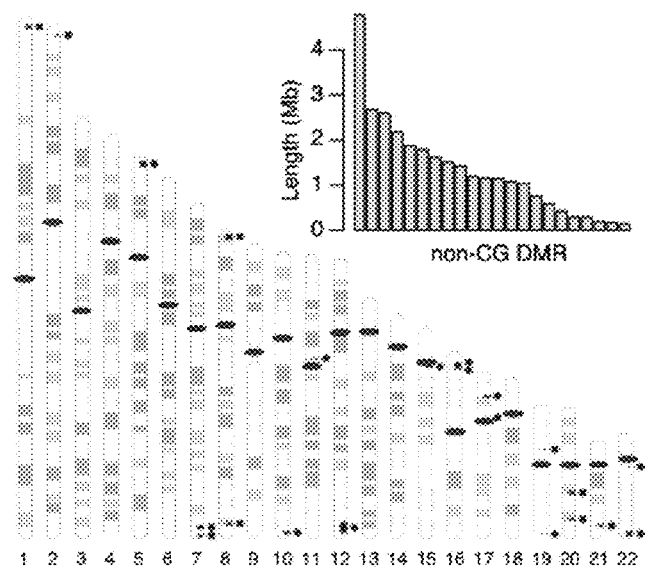
(FIG. 5a) Chromosome ideograms and length distribution (inset) of the 22 ADS-iPSC non-CG mega-DMRs. Blue circles and lines indicate location of individual DMRs. Dark ellipses indicate the location of centromeres.
Figure 6A:
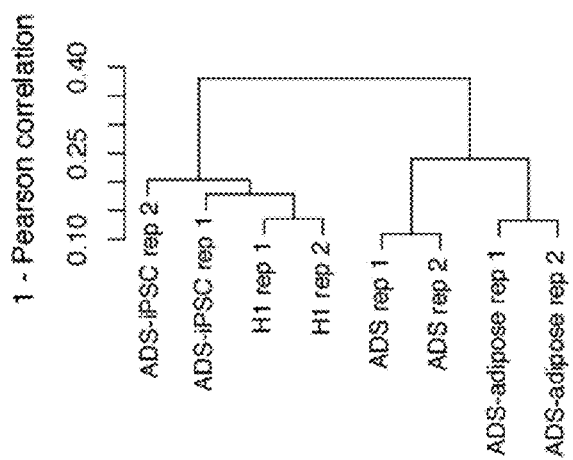
(FIG. 6a) Complete linkage hierarchical clustering of both biological replicates of ADS-adipose somatic cells, ADS cekks, ADS-iPSCs and H1 ESCs, base don RPKM values from strand-specific RNA-seq.
Figure 6B:
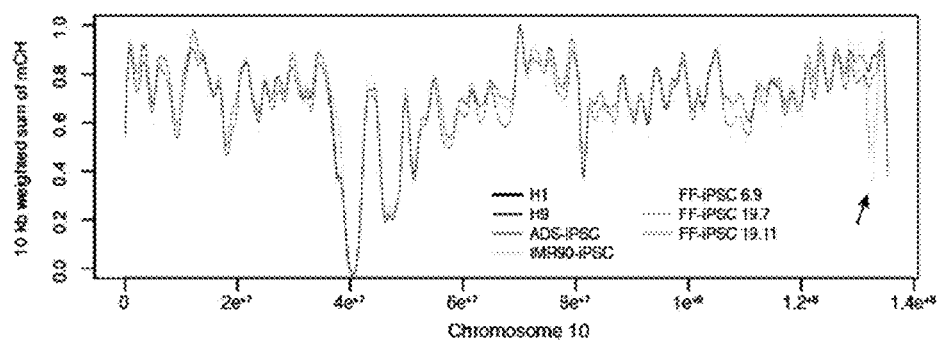
(FIG. 6b) Plot of the density of mCH identified in chromosome 10. Lines represent smooting of mCH density in 10 kb windows. Black arrow indicates a large region of dissimilarity between ESCs and iPSCs. Abbreviations: mCG/mCH, methylated cytosine in the CG/CH context.
Figure 10:
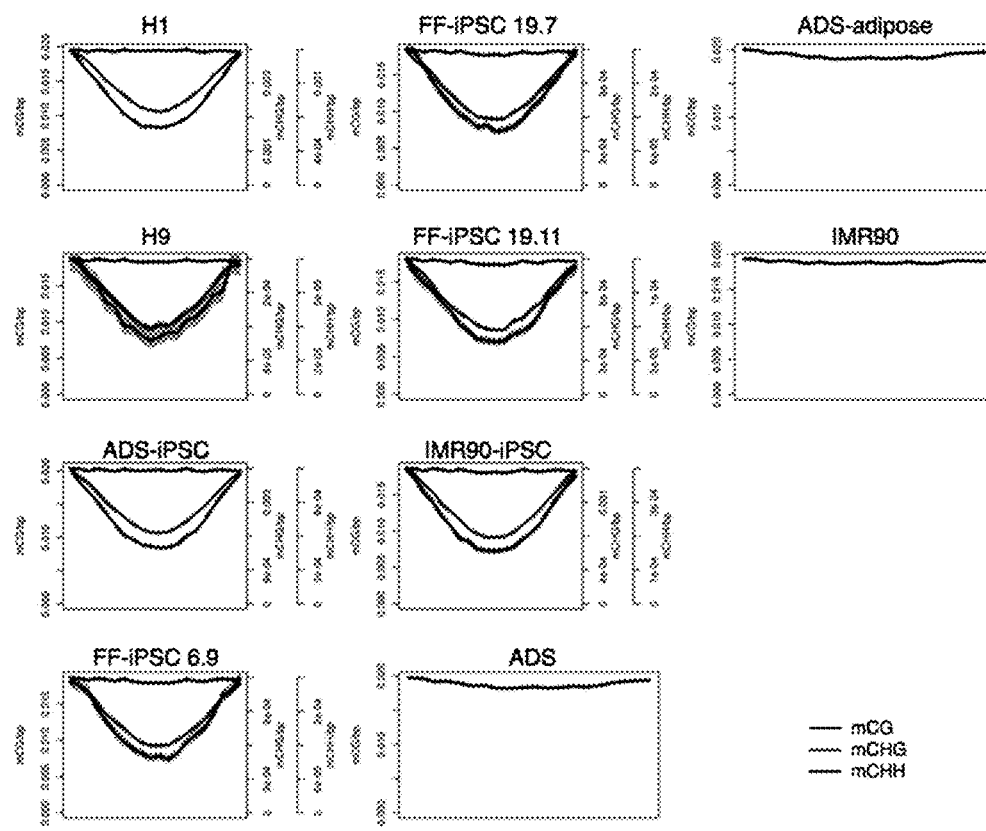
FIG. 10. Density of DNA methylation at enhancer sites. The average relative DNA methylation densities in each sequence context in 100 bp windows are displayed throughout 5 kb upstream to 5 kb downstream of enhancers identified in H1 embryonic stem cells. Shaded areas indicate the $95^{th}$ confidence interval for the mean.
Figure 11:
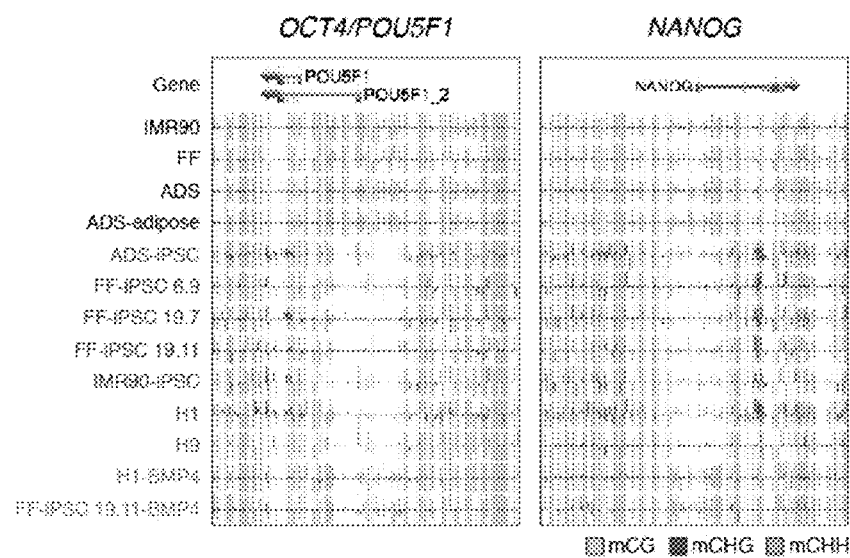
FIG. 11. DNA methylation patterns at pluripotency-related genes. AnnoJ data browser representation of DNA methylation in all cell lines at pluripotency-related genes.
Figure 12:
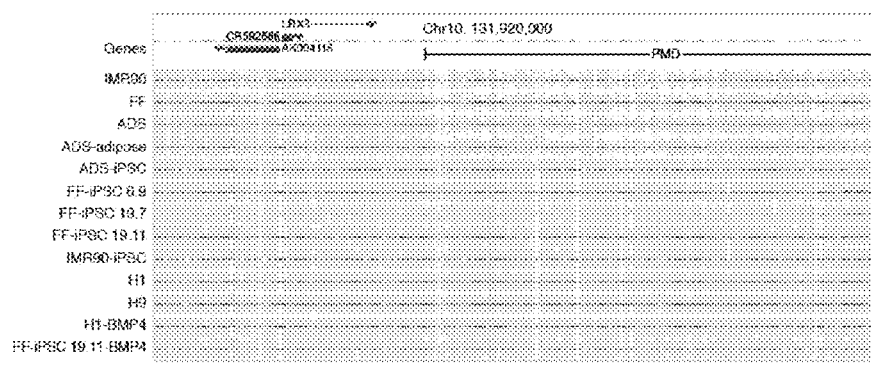
FIG. 12. Restoration of fully-methylated state in iPSCs at somatic PMDs. AnnoJ browser representation of DNA methylation at a PMD genomic region that is partially methylated in somatic cell types, but fully methylated in both ESCs and iPSCs. For the DNA methylation tracks, vertical lines above and below the dotted central line indicate the presence of methylcytosines on the Watson and Crick strands, respectively. Only DNA methylation sites in the CG context are displayed, and the vertical height of the line indicates the methylation level of each methylsytosine. Abbreviations: MCG, methylcytosine (CG context); PMD partially methylated domain.
Figure 13:
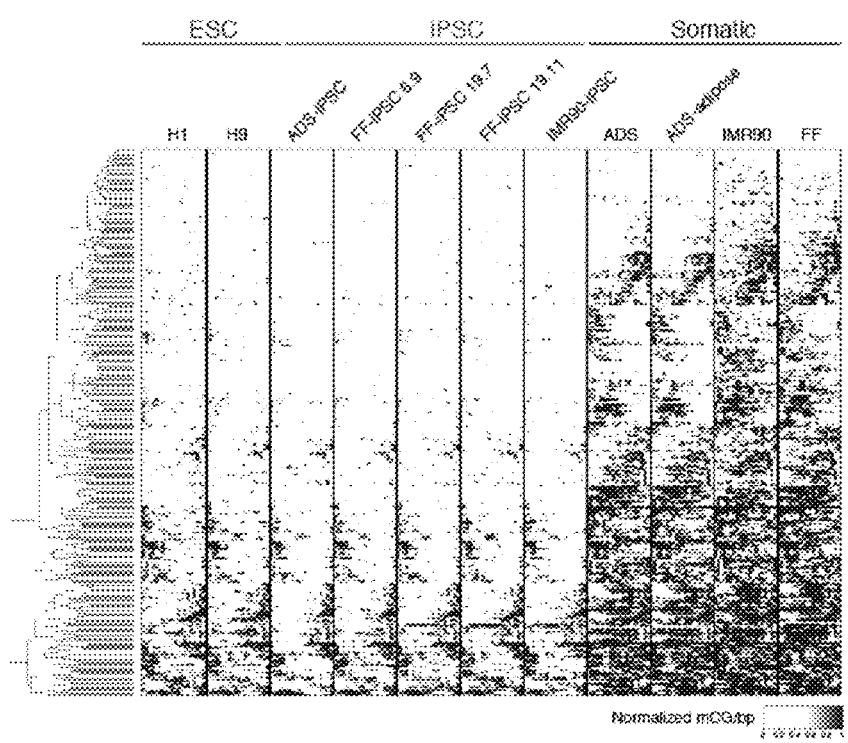
FIG. 13. Clustering of CG-DMRs at CGIs hypomethylated in ESCs relative to somatic cells. Complete linkage hierarchical clustering of mCG density within CG-DMRs identified between all ESCs and somatic cells, hypomethylated in ESCs relative to somatic cells, and coincident with CGIs. Each CG-DMR was profiled over 20 equally sized bins.
Figure 14:
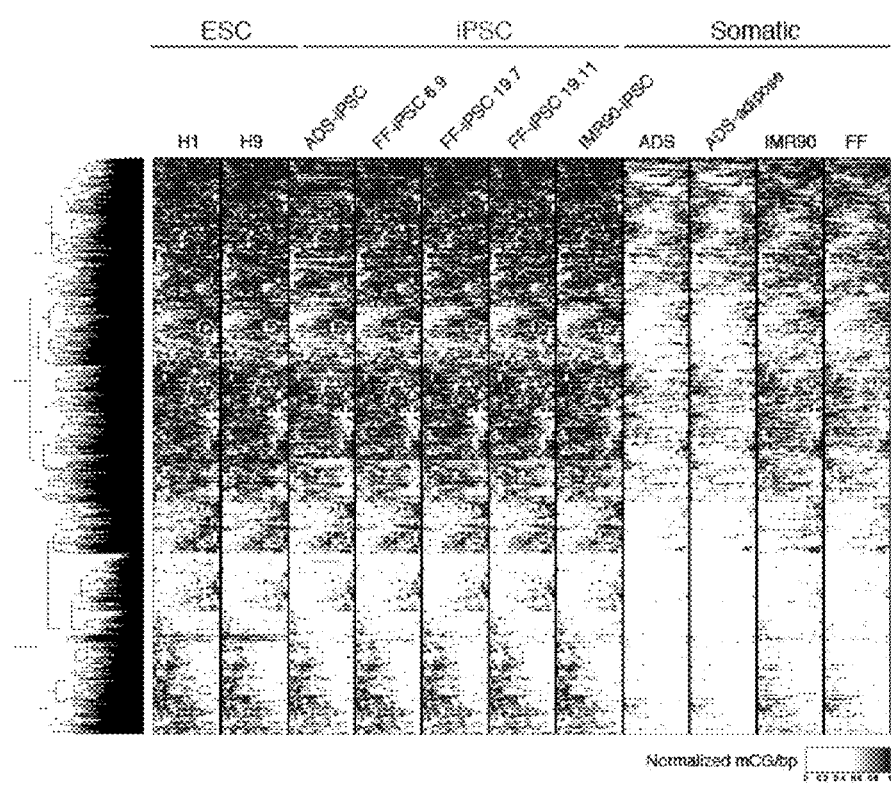
FIG. 14. Clustering of CG-DMRs at CGIs hypomethylated in somatic cells relative to ESCs. Complete linkage hierarchical clustering of mCG density within CG-DMRs identified between all ESCs and somatic cells, hypomethylated in somatic cells relative to ESCs, and coincident with CGIs. Each CG-DMR was profiled over 20 equally sized bins.
Figure 15:
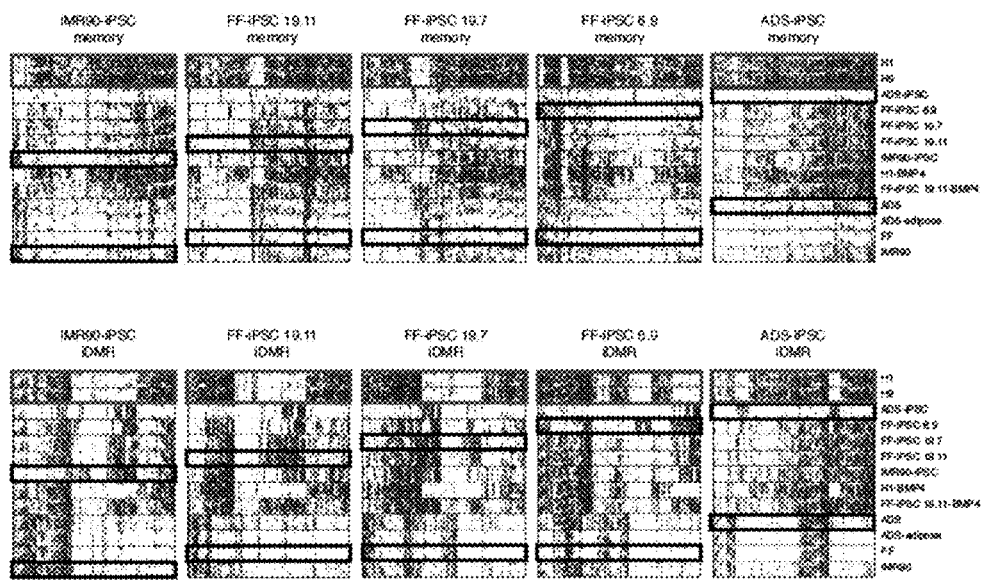
FIG. 15. Heatmaps of MCG density for the CG-DMRs in each iPSC line that are similar or dissimilar to their progenitor somatice lines. mCG density is profiled in 20 bins over the CG_DMRs aberrant in each iPSC line (left black box in each heatmap) in respect to both H1 and H9 hESCs. The CG-DMRs are divided according to the similarity to the methylation statures of the progenitor somatic lines (right black blox in each heatmap): CG-DMRs similar to progenitor somatic line (memory) in left column, and CG-DMRs dissimilar to parental line on the right column (iDMR).
Figure 16:
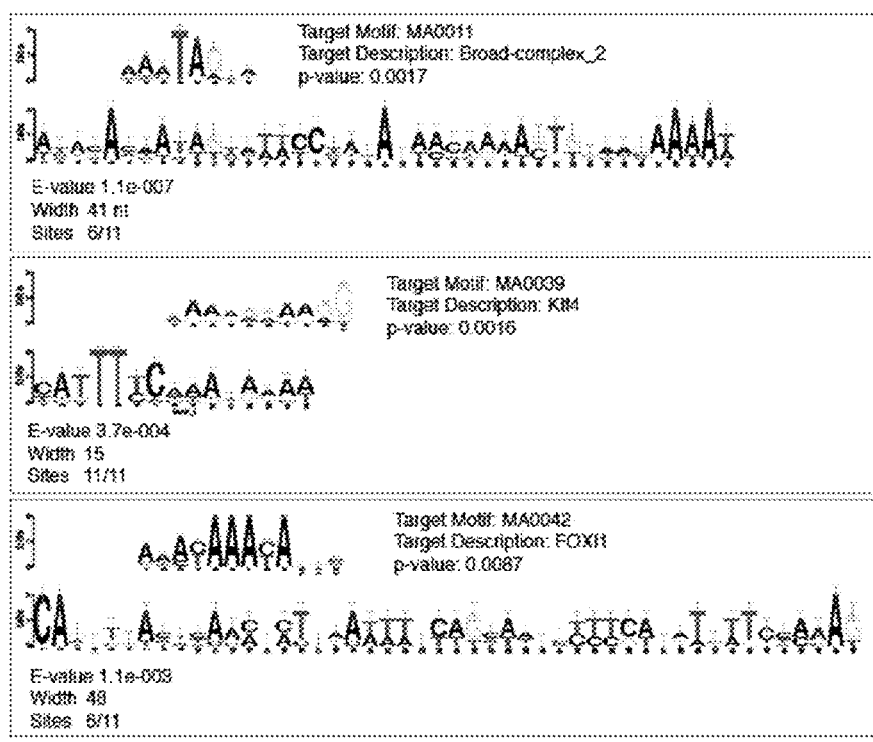
FIG. 16. Analysis of over-represented motifs in the CG-DMRs conserved among all iPSC lines. 11 hypermethylated and 119 hypomethylated CG-DMRs shared by all five iPSC lines were considered, and sequences 1 kb upstream and downstream of the center of each DMR were retrieved (Watson strand). MEME was used to identify sequence patterns that occur repeatedly in the two groups of DNA sequences. As a control, since the CG-DMRs are highly enriched for CG islands, a set of 2 kb sequences were retrieved from 100 random CG islands. The top 5 sequences within each group were considered (hypermethylated and hypomethylated CG-DMRs and random CG islands; E-value <0.01). These sequences were analyzed with TOMTOM searching for transcription factor binding sites (TFBS, based on the JASPAR core DB; q-value, 0.5). Three out of the five sequences identified within the set of hypermethylated CG-DMRs were found to contain binding sites but not found in the reference CG island set. The logo blots for these three sequences are displayed, with a length of 41, 15 and 48 nt, together with the logo plot of the matching TFBS. All analysis were performed with the MEME suite.
Figure 17:
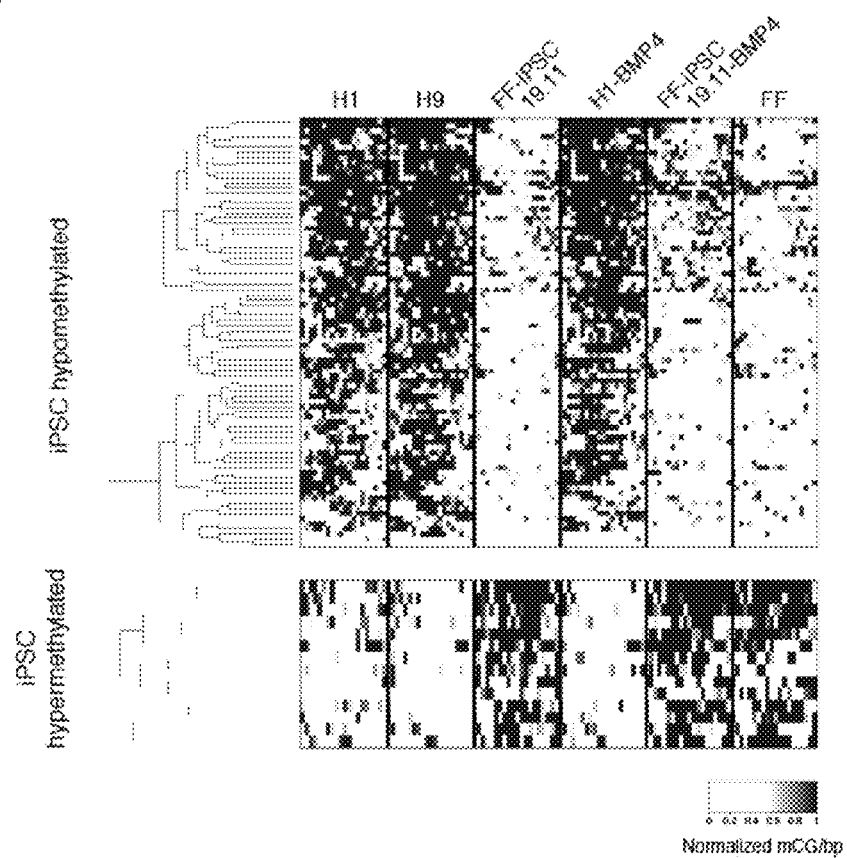
FIG. 17. Clustering of FF-iPSC 19.11 CG-DMRs relative to ESCs, where somatic DNA methylation memory in FF-iPSC 19.11 is transmitted through cellular differentiation. Complete linkage hierarchical clustering of mCG density within CG-DMRs identified between FF-iPSC 19.11 and both ESCs, where FF-iPSC 19.11, FF somatic progenitor, and FF-iPSC 19.11 differentiated with BMP4 to trophoblast lineage display the same methylation state. Separate heatmaps are shown for iPSC hypermethylation and hypomethylation relative to the ESCs. Each CG-DMR was profiled over 20 equally sized bins.
Figure 18:
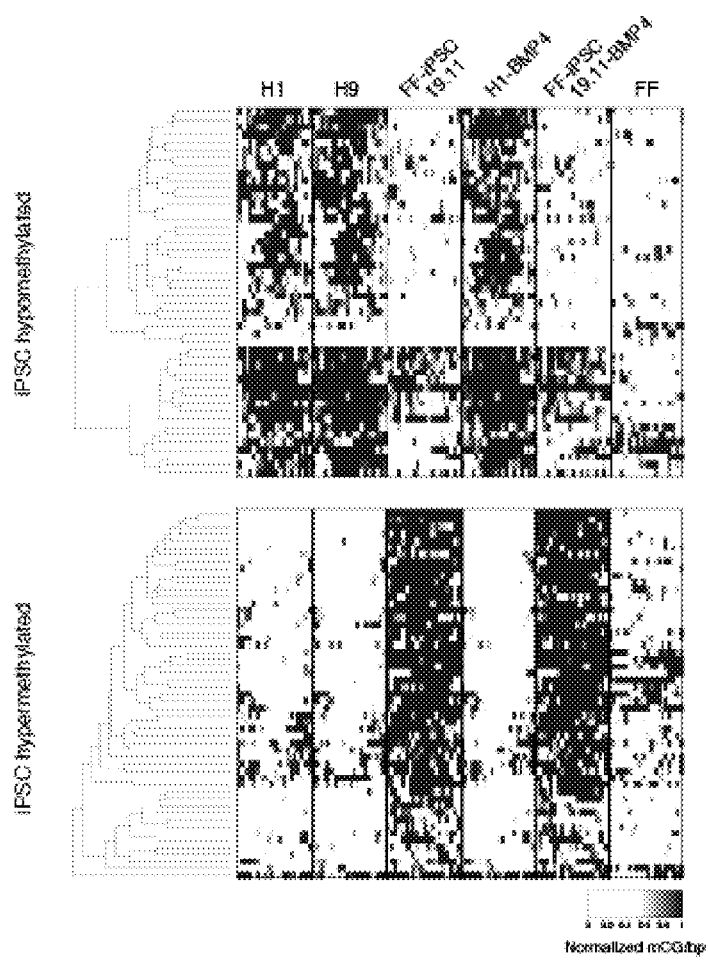
FIG. 18. Clustering of FF-iPSC 19.11 CG-DMRs relative to ESCs, where FF-iPSC 19.11 methylation patterns unlike both the FF somatic progenitor and ESCs are transmitted through cellular differentiation. Complete lineage hierarchical clustering of mCG density within CG-DMRs identified between FF-iPSC 19.11 and both ESCs, where FF-iPSC 19.11 shows a methylation state not found in either ESCs or FF somatic progenitor, and FF-iPSC 19.11 differentiated with BMP4 totrophoblast displays the same methylation state as FF-iPSC 19.11. Separate heatmaps are shown for iPSC hypermethylation and hypomethylation relative to the ESCs. Each CG-DMR was profiled over 20 equally sized bins.
Figure 19A:
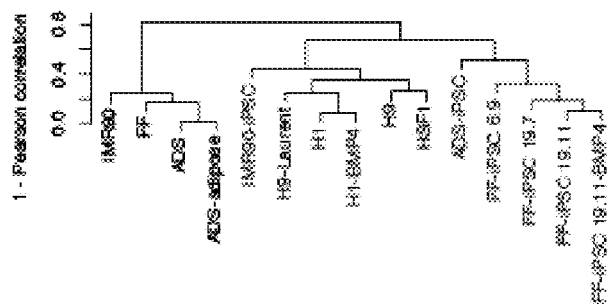
(FIG. 19a) Complete linkage hierarchical clustering of mCG density within the 1175 CG-DMRs identified between iPSCs and H1 and H9 ESCs (FIG. 3a), which were also profiled in the HSF1 and H9-Laurent ESCs.
Figure 19B:
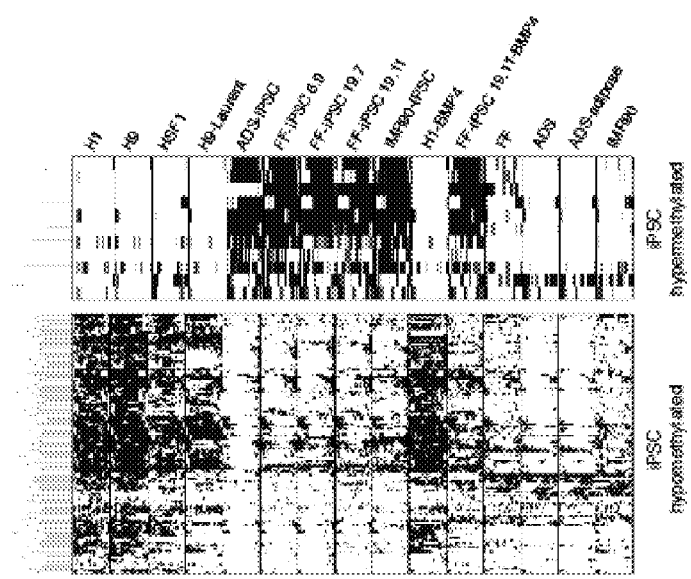
(FIG. 19b) as in FIG. 19a for the hypermethylated or hypomethylated CG-DMRs in all iPSCs. In both FIG. 19a and FIG. 19b the two additional ESCs show high similarity to H1 and H9 ESCs.
Figure 20A:
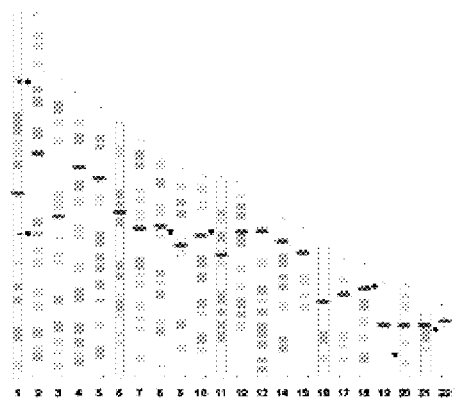
(FIG. 20A) Chromosome ideograms of the 7 large non-CG DMRs where H1 is hypomethylated relative to ADS-iPSC.
Figure 20B:
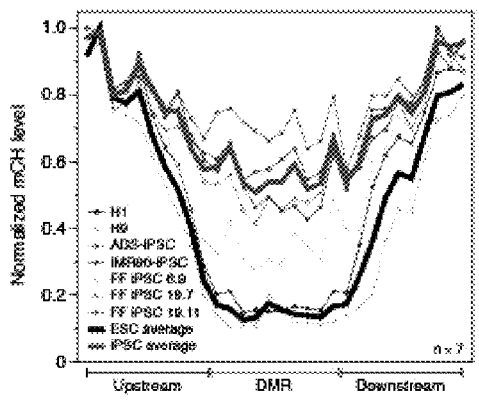
(FIG. 20B), Normalized mCH levels over the 7 large non-CG DMRs and flanking genomic regions where H1 is hypomethylated relative to ADS-iPSC.
Figure 20C:
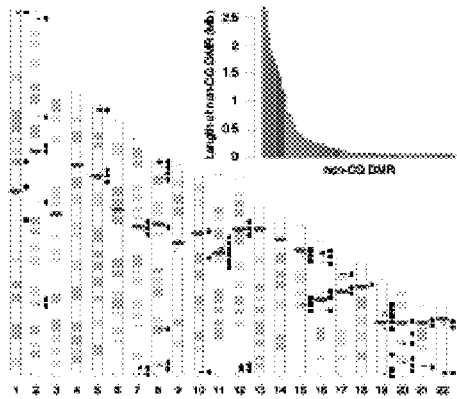
(FIG. 20C) Chromosome ideograms of all 78 non-CG DMRs where ADS-iPSC is hypomethylated relative to H1.
Figure 20D:
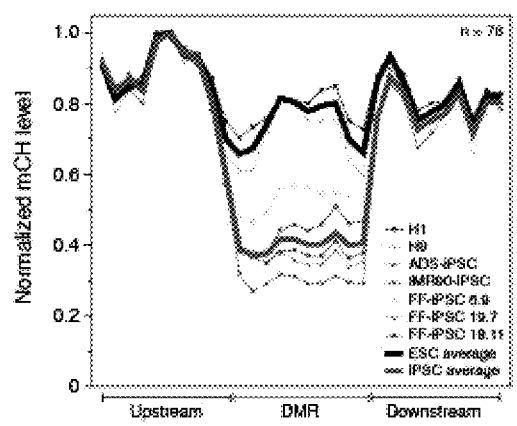
(FIG. 20D) Normalized mCH levels over all 78 non-CG DMRs where ADS-iPSC is hypomethylated relative to H1 and flanking genomic regions.
Figure 20E:
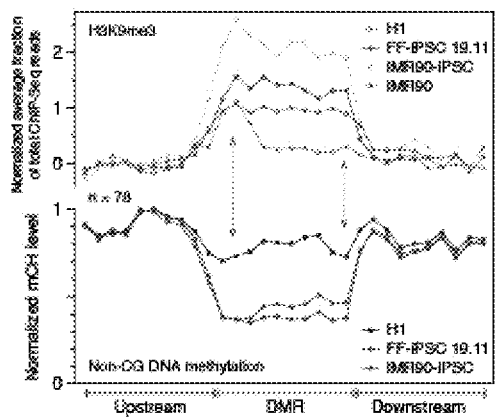
(FIG. 20E) Lower y-axis as in (f) for the cell lines indicated. Upper y-axis shows profiles of normalized H3K9me3 ChIP-Seq read density throughout the 78 non-CG DMRs.
Figure 20F:
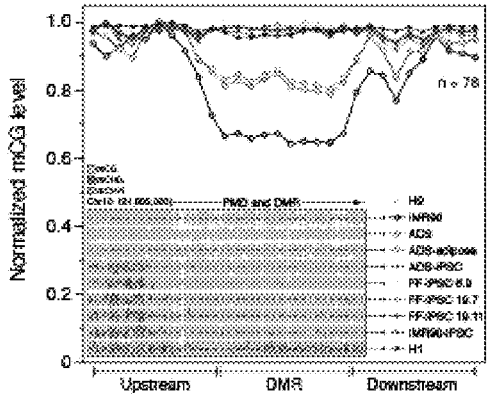
(FIG. 20F) Plot displays normalized mCG levels over the 78 non-CG DMRs and flanking genomic regions.
Figure 21:
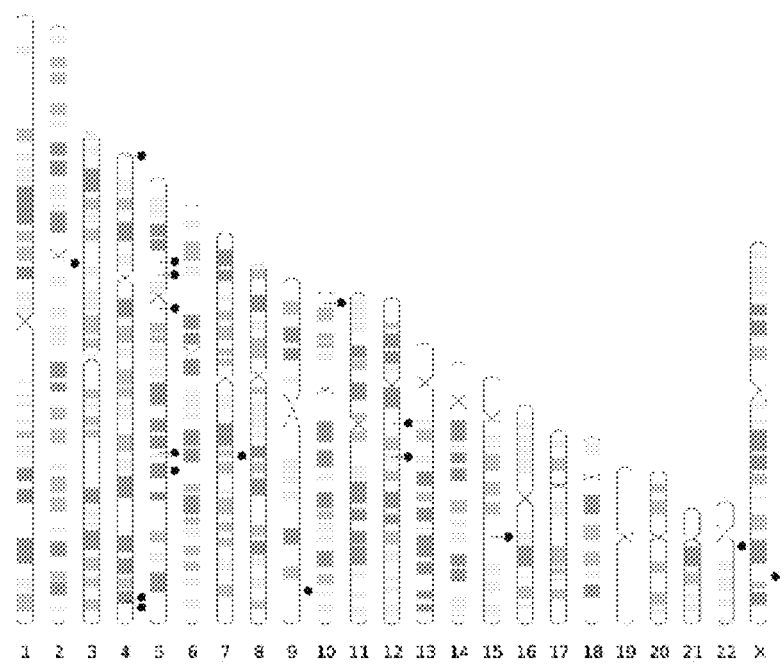
FIG. 21. Retroviral insertion sites in ADS-iPSC. Ideogram of the retroviral insertion sites in the genome of ADS-iPSC, indicated by drak dots.
Figure 22:
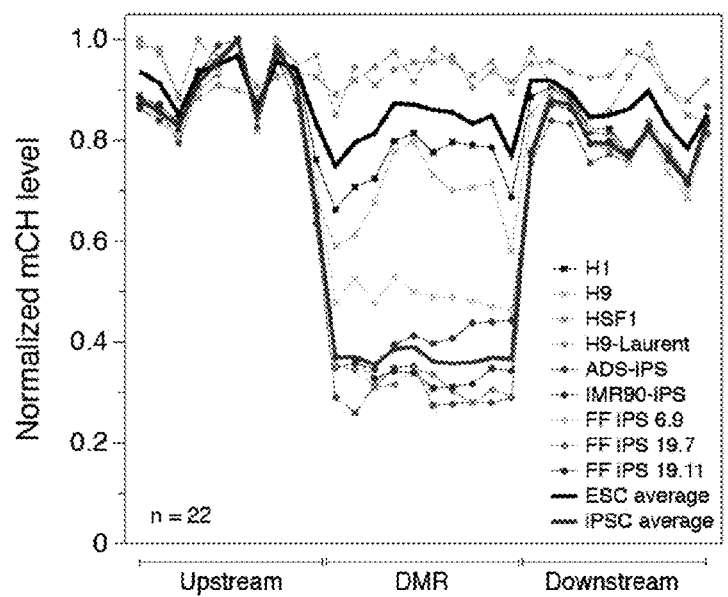
FIG. 22. Validation of the non-CG mega-DMRs in two additional ESC lines. Normalized mCH levels over all non-CG mega-DMRs and flanking genomic regions, including the previously published HSF1 and H9-Laurent ESCs.

Failure to Restore Megabase-Scale Regions of Non-CG Methylation is a Hallmark of iPSC Reprogramming While non-CG DNA methylation levels and distribution were very similar between ESCs and iPSCs on a whole-genome and chromosomal scale (FIG. 1), a systematic comparison of non-CG methylation levels between the H1 and the ADS-iPSC lines throughout the autosomes revealed the presence of 29 large, non-CG differentially methylated regions (FDR=1%, fold difference in mCH level≥2, Supplementary table 4). These non-CG "mega"-DMRs tended to be very large, with half greater than 1 Mb in length, the longest ~4.8 Mb, and in total all 29 comprised 32.4 Mb, or ~1% of the genome (FIG. 5a, inset). The majority of non-CG mega-DMRs were hypomethylated in the mCH context in the ADS-iPSC line (22, total length=29.1 Mb), while only few (7, total length=3.4 Mb) were hypomethylated in H1 relative to ADS-iPSC (Supplementary FIG. 10a,b). The H1-hypomethylated non-CG mega-DMRs contained 36 genes enriched for biological processes related to epidermal cell differentiation (54% of 36 genes, P=1.5e$^{-35}$), and that predominantly were not expressed in H1 but were transcribed at a low level in ADS-iPSC (Supplementary Table 5). These H1-hypomethylated mega-DMRs encompassed two gene clusters encoding pregnancy-specific beta-1 glycoproteins (chromosome 19) and late cornified envelope proteins within the epidermal differentiation complex (chromosome 1) which are involved in epidermal differentiation during development (Marshall, D. et al., *Proc Natl Acad Sci USA* 98:13031-13036 (2001)). Focusing subsequent analysis on the 22 non-CG mega-DMRs in which the ADS-iPSC line failed to restore non-CG methylation upon establishment of pluripotency, Applicants discovered that non-CG mega-DMR localization was strongly biased towards close proximity to centromeres and telomeres (FIG. 5a, 15 of 22 located within 5% of chromosomal length from a telomere or centromere, Poisson P=1e$^{-12}$), suggesting that somatic cell reprogramming may be susceptible to DNA methylation abnormalities in these chromosomal regions. Applicants hypothesized that the retroviral insertion used to introduce the pluripotency factors in ADS-iPSC may have disrupted the reprogramming of DNA methylation. However, identification of the retroviral insertion sites by PCR-amplification and Illumina-based sequencing of the junctions between the ADS-iPSC genomic DNA and the MMLV retroviral 5' and 3' LTRs did not identify significant overlap between the 17 insertion sites and the non-CG mega-DMRs (Supplementary FIG. 11, Supplementary table 6).

Figure 5B:
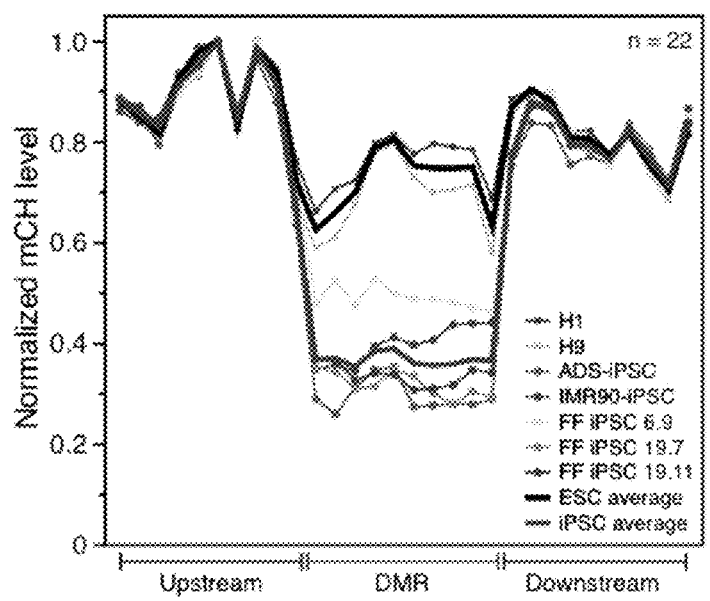
(FIG. 5b) Normalized mCH levels over all non-CG mega-DMRs and flanking genomic regions.
Figure 5C:
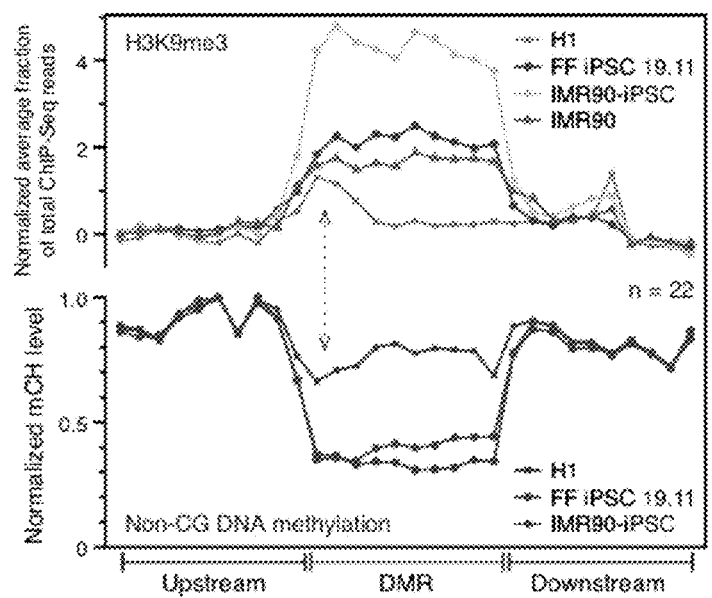
(FIG. 5c) Lower y-axis as in (FIG. 5b) for the cell lines indicated. Upper y-axis: normalized H3K9me3 ChIP-Seq read density throughout the non-CG mega-DMRs and flanking genomic regions. Dashed arrows indicate the inverse relationship between mCH and H3K9me3.

Applicants next profiled the average non-CG DNA methylation level throughout the 22 ADS-iPSC hypomethylated non-CG mega-DMRs and flanking genomic regions for each of the 7 ESC and iPSC methylomes. This analysis revealed that depletion of non-CG methylation in these regions was a common feature of the independent iPSC lines, whereas such depletion was not observed in either of the ESC lines (FIG. 5b, and FIG. 1f, arrow). Depletion of non-CG methylation in individual regions was evident in multiple iPSCs, specifically with 20, 15 and 6 of the DMRs manifesting depletion in at least 3, 4 or all 5 iPSC lines, respectively (Supplementary Table 4). Applicants hypothesized that the localized failure to restore non-CG methylation in these large regions could be mechanistically linked to the presence of particular covalent histone modifications that impart a regional chromatin conformation that is refractive to re-methylation at CH sites. Accordingly, Applicants analyzed the genomic distribution of the heterochromatin modifications H3K9me3 and H3K27me3 throughout the genomes of two of the iPSC lines (FF-iPSC 19.11 and IMR90-iPSC (Hawkins, R. D. et al. *Cell Stem Cell* 6:479-491 (2010)), and in both cell lines Applicants identified significant regional enrichment of H3K9me3 that was spatially concordant with the non-CG mega-DMRs, and absent from the flanking genomic regions (FIG. 5c). Notably, H3K9me3 was not observed throughout these same genomic regions in H1 ES cells, but rather a low level of regional enrichment was observed at the 5' end of the DMRs coincident with a small decrease in H1 mCH level (FIG. 5c). Furthermore, the IMR90 genome also displayed enrichment of H3K9me3 highly spatially correlated with the non-CG mega-DMRs. Additionally, Applicants profiled the average level of CG methylation in the genomes of all analyzed cell lines, revealing that the regions of the genome identified as non-CG mega-DMRs in ADS-iPSCs tend to be partially methylated in non-pluripotent cells (21 of 22 non-CG mega-DMRs overlap with ADS PMDs, accounting for 99.5% of non-CG mega-DMR bases, FIG. 5d). Taken together, these data indicate that specific large regions of somatic cell genomes proximal to centromeres and telomeres that are in the partially methylated mCG state, and that bear the heterochromatin modification H3K9me3, may often be resistant to complete reprogramming of non-CG methylation to the embryonic state, remaining in a somatic configuration after induction of pluripotency. As every iPSC methylome displayed a significantly lower non-CG methylation level averaged over this set of non-CG DMRs identified between H1 and ADS-iPSC genomes (exemplified for one DMR in FIG. 5e), these regional aberrations appear to be a common and conserved feature of somatic cell reprogramming.

Figure 5D:
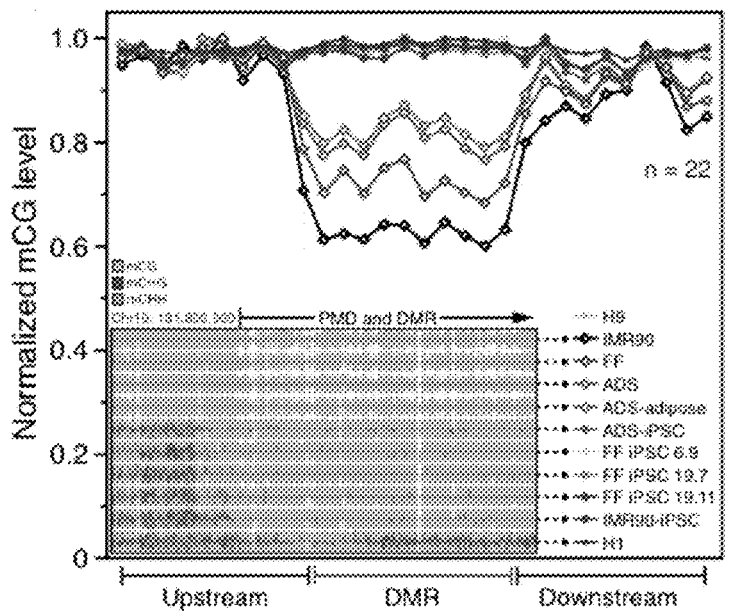
(FIG. 5d) Plot displays normalized mCG levels over the non-CG mega-DMRs and flanking genomic regions. Inset is a data browser representation of DNA methylation where vertical bar height indicates mC level, at the 5' of a non-CG mega-DMR and PMD.
Figure 5E:
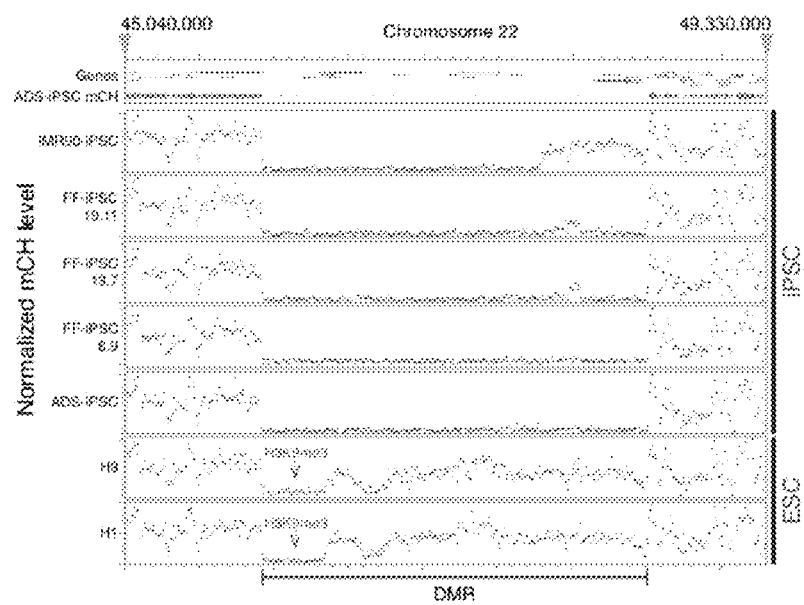
(FIG. 5e) Normalized mCH levels over a non-CG mega-DMR on chromosome 22 and flanking regions. Top panel shows gene models and ADS-iPSC mCH.
Figure 5F:
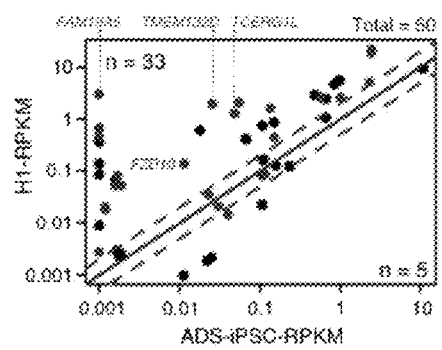
(FIG. 5f) Comparison of transcript abundance between H1 and ADS-iPSC. Each dot represents a RefSeq gene within the 22 non-CG mega-DMRs. Red dots indicate genes that have a CG-DMR within 2 kb of the transcriptional start site. Dark dots indicate genes that have a CG-DMR within 2 kb of the transcriptional start site, are hypermethylated in all iPSC lines and are associated with loss of H3K27me3. Dashed lines represent 2-fold difference.
Figure 5G:
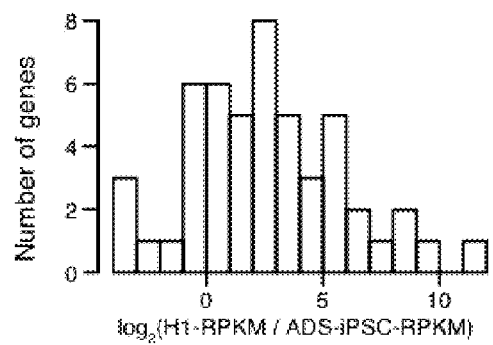
(FIG. 5g) The number of genes with a given transcript abundance ratio between H1 and ADS-iPSC for all RefSeq genes within the non-CG mega-DMRs.

To determine if the non-CG mega-DMRs affected disruption of transcriptional activity, Applicants compared the transcript abundance between ADS-iPSCs and H1 ESCs of genes located within the ADS-iPSC non-CG mega-DMRs (FIG. 5f). Of the 50 RefSeq genes within the non-CG mega-DMRs, 33 showed ≥2-fold lower transcript abundance in ADS-iPSC compared to H1 ESCs, while only 5 genes showed ≥2-fold higher transcript abundance in ADS-iPSC compared to H1 ESCs, and the changes were to a lesser degree (Supplementary table 7). This indicates that these aberrantly reprogrammed regions are associated with transcriptional disruption in the iPSCs (FIG. 5g). Notably, 13 of the 15 CG DMRs that were consistently hypermethylated in every iPSC line (FIG. 4d,e) were located within the non-CG mega-DMRs, constituting a highly significant enrichment ($P=8.5e^{-39}$). Finally, 64% of genes with lower transcript abundance in ADS-iPSC in non-CG mega-DMRs also displayed dense CG hypermethylation at the transcriptional start site (TSS, FIG. 5f, red circles), a subset of which were consistently hypermethylated at the TSS in all iPSC lines analyzed and associated with aberrant loss of H3K27me3 (FIG. 5f, blue circles, FIG. 4e) providing potential molecular markers for determination of complete reprogramming in iPSC lines. Several of these suppressed genes exhibiting TSS CG-hypermethylation encode proteins that may be pertinent to processes of cellular differentiation and development, particularly in neural lineages: TMEM132D, implicated in panic/anxiety disorders in humans and mice (Erhardt, A. et al. *Molecular psychiatry* (2010)); FAM19A5, encoding a novel neuropeptide highly expressed in the CNS with neuroprotective roles (Yilmaz, G. et al., *Exp Transl Stroke Med* 2:11 (2010)); DPP6, encoding a protein associated with brain Kv4 channels and human neural disease (Clark, B. D. et al. *Front Mol Neurosci* 1:8 (2008)); TCERG1L, encoding a transcription factor enriched in the dorsal horn of the mouse embryonic spinal cord (Li, M. Z. et al. *Dev Biol* 292:555-564 (2006)); FZD10, encoding a Wnt protein receptor highly expressed in a variety of CNS tissues. Notably, three of these genes (TCERG1L, DPP6 and FAM19A5) were reported as consistently expressed significantly higher in ESCs compared to iPSCs (Chin, M. H. et al. *Cell Stem Cell* 5:111-123 (2009)) (J.A.T., personal communication), further indicating that the epigenomic dysregulation Applicants have characterized is a common feature of iPSCs. Applicants hypothesize that in the absence of reprogramming and differentiation methodologies that reset the aberrantly CG-hypermethylated and repressed state of these genes, derivation of fully functional neuronal lineages from iPSCs may be impeded. In this regard, it is noteworthy that a diminished frequency of neural differentiation of human iPSCs compared to human ESCs has previously been reported (Hu, B. Y. et al. *Proc Natl Acad Sci USA* 107:4335-4340 (2010)).

Through generation of the first unbiased, whole-genome, single-base resolution DNA methylomes for a variety of iPSCs and ESCs Applicants have gained several novel insights into the epigenomic reprogramming process. First, reprogramming induces a remarkable reconfiguration of the DNA methylation patterns throughout the somatic cell genome, returning PMDs to a fully methylated state, reinstating non-CG methylation, and reprogramming most unmethylated and methylated CGIs to an ESC-like state. Overall, this process generates an iPSC methylome that, in general, is very similar to that of ESCs. In addition, with new methylomes for both ESCs and somatic cells, the characteristics that Applicants previously proposed to demarcate a pluripotent DNA methylome from that of a differentiated cell remain applicable (Lister, R. et al. *Nature* 462:315-322 (2009)): non-CG methylation is a hallmark of pluripotent cells, while large tracts of partial CG methylation are characteristic of differentiated cells.

Upon closer inspection numerous aberrations in the reprogramming were evident, a significant fraction of which were present in all iPSC lines despite encompassing progenitor somatic cells from different germ layers and possessing different genotypes, reprogramming by independent laboratories, and using three different iPSC induction technologies. In terms of mCG, reprogramming generated hundreds of differentially methylated regions, most associated with CGIs and genes, and appearing to represent both memory of the somatic cell DNA methylation patterns as well as novel aberrant DNA methylation. Notably, many of the novel CG-DMRs were shared between independent iPSC lines, indicating that these loci are inherently susceptible to aberrant methylation in the reprogramming process. Furthermore, the presence of unique CG-DMRs in each iPSC line indicate that in addition to the aforementioned susceptible regions, there may be a stochastic element to reprogramming that results in inter-clone variability.

Applicants also identified megabase-scale genomic regions that were repeatedly resistant to reprogramming of non-CG methylation, and were associated with altered H3K9me3 and transcriptional activity, constituting phenotypic consequences at the transcriptional level that could have downstream consequences for iPSC or derived somatic cell function. The close proximity of the non-CG mega-DMRs to centromeres and telomeres suggests that there could be distinct molecular properties of these chromosomal regions, for example particular histone variants, which impede the reprogramming process. Together, the non-CG mega-DMRs, common CG-DMRs in all iPSC lines, and differentially expressed genes are useful as diagnostic markers for incomplete iPSC reprogramming, characterization of the efficacy of different reprogramming techniques, and potential propagation of altered methylation states into derivative differentiated cells. From these first comprehensive whole-genome, base-resolution methylome maps it appears clear that iPSCs are fundamentally distinct from ESCs, insofar as they manifest common, quantifiable epigenomic differences.

Example 4

Biological Materials and Sequencing Libraries

Strand-specific mRNA-Seq libraries were produced as described previously (Lister, R. et al. *Nature* 462:315-322 (2009)). MethylC-Seq libraries were generated by ligation of methylated sequencing adapters to fragmented genomic DNA followed by purification, sodium bisulfite conversion and 4 cycles of PCR amplification as described previously (Lister, R. et al. *Nature* 462:315-322 (2009)), with minor modifications (See Supplementary Materials). ChIP-Seq libraries were prepared following Illumina protocols with minor modifications (See Supplementary Materials). Sequencing was performed using the Illumina Genome Analyzer IIx and HiSeq2000 instruments as per the manufacturer's instructions.

Read Processing and Alignment.

MethylC-Seq sequencing data was processed using the Illumina analysis pipeline and FastQ format reads were aligned to the human reference genome (hg18) using the Bowtie algorithm (Langmead, B. et al., *Genome Biol.* 10:R25 (2009)) as described previously (Lister, R. et al. *Nature* 462:315-322 (2009)), with minor modifications (See Supplementary Materials). mRNA-Seq reads were uniquely aligned to the human reference (hg18) and quantified using the TopHat36 and Cufflinks37 algorithms. Base calling, and mapping of Chip-Seq reads was performed using the Illumina analysis pipeline.

Cell Culture.

ADS cells were obtained from Invitrogen (Cat. #R7788110) and cultured under recommendation conditions. ADS cells were grown in 10 cm$^2$ dishes (5,000 cells/cm$^2$). For making iPSC cells, ADS cells (3,000/cm$^2$) were plated in six-well plates. The cells were infected with the combination of human reprogramming retroviruses (c-MYC, KLF4, OCT4, or SOX2 in pMXs; Addgene) that had been produced in 293T cells co-transfected with gag/pol and VSV-G as described above. On day 5, cells were passed onto 10-cm dishes covered with feeder MEFs or onto 6-cm dishes without MEFs. Cells were cultured in DMEM/F12 plus 20% KSR supplemented with β-mercaptoethanol (0.1%), NEAA (1×), Glutamax (1%), and 10 ng/mL FGF2. Medium was changed every day. On days 18-28, individual colonies were picked and cultured feeder-free in defined mTeSR1 medium on plates coated with matrigel. The profiled ADS-iPSC clone was assayed for pluripotency by analysis of the transcript abundance of pluripotency markers, and in vitro and in vivo (teratoma) differentiation into 3 germ layers, as described previously (Sugii, S. et al. *Proceedings of the National Academy of Sciences* (2010)). For differentiation from ADS cells to mature adipocyte in vitro, ADS cells (10,000/cm$^2$) were plated on 10 cm$^2$ dishes with growth media. Differentiation was induced for 14 days using medium consisting of DMEM-F12, 10% KSR, and an adipogenic cocktail (0.5 mM IBMX, 0.25 uM dexamethasone, 1 ug/ml insulin, 0.2 mM indomethacin and 1 uM pioglitazone). For collecting mature adipocytes, the cells were detached with trypsin, then neutralized. After centrifuging detached cells, floated fat cells were transfer into new tubes. H9 cells were passage 42 including several passages in mTeSR1. IMR90-iPSCs were derived by lentiviral integration as reported previously (Yu, J. et al. *Science* 318: 1917-1920 (2007)), and were passage 65, with 33 passages in mTeSR1. Foreskin fibroblast (FF) iPSC lines were derived using non-integrating episomal vectors as described previously (Yu, J. et al. *Science* 324:797-801 (2009)). Prior to cell harvest aliquots of cells were assayed for Oct4 expression by flow cytometry as described previously (Ludwig, T. et al. *Nature Methods* 3:637-646 (2006); Ludwig, T. et al. *Nat Biotechnol* 24:185-187 (2006)). These cells were submitted to the WiCell Cytogenetics Laboratory to confirm normal karyotype.

MethylC-Seq Library Generation.

Five μg of genomic DNA was extracted from frozen cell pellets using the DNeasy Mini Kit (Qiagen, Valencia, Calif.) and spiked with 25 ng unmethylated c1857 Sam7 Lambda DNA (Promega, Madison, Wis.). The DNA was fragmented with a Covaris S2 (Covaris, Woburn, Mass.) to 75-175 bp or 100-400 bp for single-read or paired-read libraries, respectively, followed by end repair and addition of a 3' A base. Cytosine-methylated adapters provided by Illumina (Illumina, San Diego, Calif.) were ligated to the sonicated DNA as per manufacturer's instructions for genomic DNA library construction. For single-read libraries, adapter-ligated DNA was isolated by two rounds of purification with AMPure XP beads (Beckman Coulter Genomics, Danvers, Mass.). For paired-read libraries, adapter-ligated DNA of 275-375 bp (150-250 bp insert) was isolated by 2% agarose gel electrophoresis. Adapter-ligated DNA (≤450 ng) was subjected to sodium bisulfite conversion using the MethylCode kit (Life Technologies, Carlsbad, Calif.) as per manufacturer's instructions. The bisulfite-converted, adapter-ligated DNA molecules were enriched by 4-8 cycles of PCR with the following reaction composition: 2.5 U of uracil-insensitive PfuTurboC$_x$ Hotstart DNA polymerase (Stratagene), 5 μl 10× PfuTurbo reaction buffer, 31 μM dNTPs, 1 μl Primer 1, 1 μl Primer 2 (50 μl final). The thermocycling parameters were: 95° C. 2 min, 98° C. 30 sec, then 4-8 cycles of 98° C. 15 sec, 60° C. 30 sec and 72° C. 4 min, ending with one 72° C. 10 min step. The reaction products were purified using AMPure XP beads. Up to two separate PCR reactions were performed on subsets of the adapter-ligated, bisulfite-converted DNA, yielding up to two independent libraries from the same biological sample. Final sequence coverage was obtained by sequencing all libraries for a sample separately, thus reducing the incidence of "clonal" reads which share the same alignment position and likely originate from the same template molecule in each PCR. The sodium bisulfite non-conversion rate was calculated as the percentage of cytosines sequenced at cytosine reference positions in the Lambda genome.

Directional RNA-Seq Library Generation.

Total RNA was isolated from cell pellets treated with RNAlater using the RNA mini kit (Qiagen, Valencia, Calif.) and treated with DNaseI (Qiagen, Valencia, Calif.) for 30 min at room temperature. Following ethanol precipitation, biotinylated LNA oligonucleotide rRNA probes complementary to the 5S, 5.8S, 12S, 18S and 28S ribosomal RNAs were used to deplete the rRNA from 5 μg of total RNA by RiboMinus (Life Technologies, Carlsbad, Calif.) as per manufacturer's instructions. Purified RNA (50 ng) was fragmented by metal hydrolysis in 1× fragmentation buffer (Life Technologies, Carlsbad, Calif.) for 15 min at 70° C., stopping the reaction by addition of 2 μl fragmentation stop solution (Life Technologies, Carlsbad, Calif.). Fragmented RNA was used to generate strand-specific RNA-seq libraries as per the Directional mRNA-seq Library Preparation Protocol (Illumina, San Diego, Calif.).

Chromatin Immunoprecipitation and ChIP-Seq Library Generation.

Chromatin immunoprecipitation (ChIP) and Illumina sequencing for H3K9me2 and H3K27me3 was performed as described previously (Hawkins, R. D. et al. *Cell Stem Cell* 6:479-491 (2010)).

Mapping Retroviral Insertion Sites.

MMLV retroviral insertion sites in ADS-iPSC genomic DNA were identified by an adapter ligation-mediated method for genome-wide mapping of insertions, as described previously (O'Malley, R. C. et al., *Nat Protoc* 2:2910-2917 (2007)), except with the following modifications. Genomic DNA was fragmented by sonication with a Covaris S2, followed by ligation of modified 5' or 3' LTR-specific Illumina adapters:

```
5'-LTR(5'-3'):
CAAGCAGAAGACGGCATACGAGATCGGTCTCGGCATTCCTGCTGAACCGC

TCTTCCGATCTTCAGTGCAGCTGTTCCATCTGTTCTTGGCCC

3'-LTR(5'-3'):
CAAGCAGAAGACGGCATACGAGATCGGTCTCGGCATTCCTGCTGAACCGC

TCTTCCGATCTTCAGTGGCCAGTCCTCCGATTGACTGAGTCG
```

A single mapping library was made each for the 5' and 5' LTRs, and each library was sequenced on the Illumina Genome Analyzer IIx. Each valid read contained the barcode sequence "TCAGTG" prepended to the 5' of the genomic DNA read sequence. Retroviral insertion sites were identified by localized enrichment of greater than 300 reads within a 2 kb window, in both the 5' LTR and 3' LTR mapping libraries, and located on opposite genome strands between the two libraries. Cloning and Sanger sequencing of library molecules from the 3' LTR mapping library confirmed genomic DNA-retroviral insertion sites for a representative fraction of the 17 insertion sites identified by high-throughput sequencing.

High-Throughput Sequencing.

Single-read methylC-seq and RNA-seq libraries were sequenced for up to 85 cycles using the Illumina Genome Analyzer IIx. Paired-read MethylC-seq libraries were sequenced for up to 75 cycles for each read using the Illumina HiSeq2000. Image analysis and base calling were performed with the standard Illumina pipeline, performing automated matrix and phasing calculations on a control library that was sequenced in a single lane of each flowcell.

Example 5

Processing and Alignment of MethylC-Seq Data to Identify Methylated Cytosines

All sequence alignments were performed against the NCBI36/hg18 human reference. Single-read MethylC-seq sequences were processed and aligned as described previously (Lister, R. et al. *Nature* 462:315-322 (2009)), except an additional filter was added to remove any mapped reads in which a read-C base was aligned to a reference-T base. Paired-read MethylC-seq data was mapped and processed as described in previously (Lister, R. et al. *Nature* 462:315-322 (2009)) with the following modifications to accommodate the paired-read data-type. Both reads in a pair were trimmed of any low quality sequence at their 3' ends and mapped to the reference genome with Bowtie v.0.12.5 (Langmead, B. et al., *Genome Biol.* 10:R25 (2009)) in paired-read mode, using the following parameters: -e 90 -l 20 -n 0 -k 10 -o 4 -I 0 -X 550 -pairtries 100 -nomaground-solexa1.3-quals. Mapped reads in a read pair that overlapped were trimmed from their respective 3' ends until the reads no longer overlapped, leaving a 1 bp gap.

Mapped reads were filtered as follows: any read with more than 3 mismatches was trimmed from the 3' end to contain 3 mismatches, any read pair which contained a cytosine mapped to a reference sequence thymine was removed, and any read pairs that had more than 3 cytosines in the non-CG context within a single read was removed (possible non-conversion in bisulfite reaction). Read pairs were then collapsed to remove clonal reads potentially produced in the PCR amplification from the same template molecule, based on common start position of read 1. The total uniquely-mapped, non-clonal read number for each library, average coverage and total sequence yield are detailed in Table S1.

For all MethylC-seq datasets, methylated cytosines were identified from the mapped and processed read data as described previously (Lister, R. et al. *Nature* 462:315-322 (2009)). The bisulfite conversion rates for all samples were over 99% (Table S1). Correction of any DNA methylation sites incorrectly categorized as non-CG due to SNPs in the sample versus reference genomes was performed as described previously (Lister, R. et al. *Nature* 462:315-322 (2009)).

Genome Annotation.

Genomic regions and CpG Islands (CGI) were defined based on NCBI BUILD 36/HG18 coordinates downloaded from UCSC web site. Promoters were arbitrarily defined as TSS+/−500 bp or 2000 bp for each Ref Seq transcript (as indicated in the text). According to the UCSC annotation many Ref Seq transcripts can be associated with a given gene, and they can have the same or alternative TSS. Gene bodies are defined as the transcribed regions, from the start to the end of transcription sites for each Ref Seq.

mC and Histone Profiles (FIG. 3-5).

FIG. 3: each CG-DMR was divided into 20 equally sized bins. The average methylation for all cytosines in the CG context within a bin in one sample was determined and normalized by the bin size. Finally, the whole dataset was divided by its 70th percentile, and values higher then 1 were forced to 1. This was performed to produce a meaningful mapping between values and colours in the heatmap key, and to avoid extreme values masking the methylation levels of other CG-DMRs. CG-DMRs were then reorganized based on their similarity by means of complete linkage hierarchical clustering, using the heatmap.2 R function.

FIG. 4*d*: Each of the 15 CG-DMRs consistently hypermethylated in the 5 iPSC lines was profiled for both mCG and the H3K27me3 histone mark throughout the CG-DMR and equivalent upstream an downstream genomic regions divided into 30 equal length bins. For DNA methylation, for each bin in each sample the total number of methylated/(methylated+unmethylated) reads was determined over the whole set of considered CG-DMRs. Final profiles were normalized dividing them by their maximum value. For the H3K27me3 histone modification ChIP-Seq reads, RPKM values were determined in each CG-DMR and normalized to the average of the upstream/downstream flanking region RPKM values.

FIG. 5*b*: As in FIG. 4*d* lower axis, but based on the mC in the CH sequence context profiled over the non-CG mega-DMRs and upstream/downstream flanking regions, minus the non-conversion frequency. The final profiles were normalized to their maximum level.

FIG. 5c: As in FIG. 4d lower axis, but based on the mC in the CH sequence context profiled over non-CG mega-DMRs and upstream/downstream flanking regions minus the non-conversion frequency. In the upper axis the H3K9me3 histone modification ChIP-Seq reads were profiled as described for the H3K27me3 profiles in FIG. 4d.

FIG. 5d: As in FIG. 4d lower axis, but based on the mC on the mCG sequence context profiled over non-CG mega-DMRs and upstream/downstream flanking regions. Profiles were normalized to their maximum levels.

FIG. 5e: As in FIG. 4d lower axis for one example non-CG mega-DMR using 10 kb bins.

Clustering of mC Profiles and Chromosome 10 Smoothed Profiles.

Methylation level for each C in the CG, CHG and CHH sequence context was summed in adjacent 10 kb windows over all autosomal chromosomes. Non-CG DNA methylation profiles were determined by adding mCHG and mCHH profiles. Clustering was performed based on the Pearson correlation over all 10 kb windows transformed into a distance measure (as 1-Pearson correlation) and using the hclust R function. Data for smoothing of non-CG mC on chromosome 10 were retrieved as for the clustering. In addition, smoothing with cubic splines was determined before plotting using the smooth.spline R function with spar argument set to 0.3.

Example 6

Identification of Differentially Methylated Regions (DMRs)

Non-CG Mega-DMRs.

Non-CG mega DMRs (FIG. 5) were identified comparing H1 to ADS-iPSC mCHG and mCHH smoothed methylation profiles. The average methylation level of mC called (1% FDR) in the mCHG and mCHH sequence context was determined in 5 kb windows (sW). The genome was scanned considering groups of 10 adjacent windows sW over a distance less than 50 kb. The set of 10 smoothed values for mCHG in the H1 sample was compared to the set of set of 10 smoothed values in the ADS-iPSC sample using the Wilcoxon test. Resulting P-values were corrected with the Benjamini-Hochberg method. Regions with P-value <0.01 (1% FDR) and 8 fold enrichment of methylation level were identified, and regions closer than 100 bp were joined. This was repeated for the mC in the CHH sequence context. Finally, mCHG and mCHH DMRs overlapping or closer than 100 kb were joined and the final set of regions was checked for having mCHG+mCHH fold enrichment of at least 2 fold between H1 and ADS-iPSC. Coverage in the region identified as differentially methylated was not significantly different between the samples or compared to flanking genomic regions, and was taken into account in the statistical test used for their identification. The set of 78 DMRs hypomethylated in ADS-iPSC (Supplementary FIG. 10c-f) was further refined, considering the size and overlap with repressive histone marks. The final set of 22 regions reported in FIG. 5 includes all the DMRs larger than 1 Mb (17) and a range of smaller ones. Also, the 22 final non-CG mega-DMRs encompass ~92% of the initial set of 78 DMRs, based on by size.

CG-DMRs.

CG-DMRs (FIG. 3) were identified similarly to non-CG mega-DMRs. Smoothed average methylation level was performed in 100 bp windows sW, and regions comprising a set of 10 adjacent windows sW over a distance less than 1100 bp were considered. The Kruskall-Wallis test was used to score each region based on the methylation levels from the two ESC and the five iPSC lines. Regions with P-value <0.01 (1% FDR) and 4 fold enrichment of methylation level (max/min over the 7 cell lines for each region) were identified, and regions closer than 100 bp were joined.

For the analysis of CGI reprogramming the CG-DMRs were identified as for the FIG. 3 CG-DMRs but including the IMR90, ADS-adipose and ADS differentiated cell lines in addition to the two ESC and the five iPSC lines.

CGI Reprogramming.

CG-DMRs different between ESCs and differentiated cells were defined within the set of CG-DMRs identified comparing all analyzed methylomes (see above), considering only CG-DMRs overlapping with CGI. In particular, for each of these CG-DMR the mCG/bp levels in 20 equally sized bins was profiled in all cell types. DMRs with pooled mCG/bp levels different from differentiated and ESC lines were identified (Wilcoxon test P-value <0.01). Similarly, the set of reprogrammed CG-DMRs was identified comparing pooled iPSC mCG profiles with the ESC samples (Wilcoxon test P-value >0.05).

CG-DMRs Reprogramming.

CG-DMRs aberrant in iPSCs and like or unlike parental cells were defined within the set of CG-DMRs identified comparing all ESC and iPSC samples. In particular, for each of these CG-DMR the mCG/bp levels in 20 equally sized bins was profiled in all cell types. ADS (or IMR90) aberrant CG-DMRs with pooled mCG/bp levels different between ADS-iPSC (or IMR90-iPSC) and ESC lines were identified (Wilcoxon test P-value <0.01). Similarly, the set of ADS (or IMR90) CG-DMRs unlike the parental line was identified comparing pooled ADS-iPSC (or IMR90-iPSC) mCG profiles with ADS (or IMR90) (Wilcoxon test P-value <0.01).

Consistency of iPSC reprogramming in many lines for each CG-DMR was determined by comparing the mCG pooled levels for each iPSC line compared to the ESC levels (Wilcoxon test) and counting how many iPSC lines had P-value <0.01.

Identification of Partially Methylated Domains (PMDs).

A sliding window approach was used to find regions of the genome that were partially methylated in each cell type, as described previously (Lister, R. et al. *Nature* 462:315-322 (2009)).

Mapping RNA-Seq Reads.

RNA-seq read sequences produced by the Illumina analysis pipeline were aligned with the TopHat software (Trapnell, C. et al., *Bioinformatics* 25:1105-1111 (2009)) to the NCBI BUILD 36/hg18 reference sequence. Reads that aligned to multiple positions were discarded. Reads per kilobase of transcript per million reads (RPKM) values were calculated with the Cufflinks software (Trapnell, C. et al. *Nature Biotechnology* 28:511-515 (2010)) using human RefSeq gene models.

Mapping and Enrichment Analysis of ChIP-Seq Reads.

Following sequencing cluster imaging, base calling and mapping were conducted using the Illumina pipeline. Clonal reads were removed from the total mapped tags, retaining only the non-clonal unique tags that mapped to one location in the genome, where each sequence is represented once. Regions of tag enrichment were identified as described previously (Hawkins, R. D. et al. *Cell Stem Cell* 6:479-491 (2010)).

Data Visualization in the AnnoJ Browser.

MethylC-Seq, RNA-seq and ChIP-Seq sequencing reads and positions of methylcytosines with respect to the NCBI BUILD 36/HG18 reference sequence, gene models and functional genomic elements were visualized in the AnnoJ 2.0 browser, as described previously (Lister, R. et al. *Cell* 133:523-536 (2008)).

What is claimed is:

1. A method of identifying an incompletely reprogrammed human induced pluripotent stem cell, comprising:

obtaining a human induced pluripotent stem cell produced using reprogramming factors;

isolating genomic DNA from the human induced pluripotent stem cell;

contacting the genomic DNA with bisulfate to detect methylation of the genomic DNA of the human induced pluripotent stem cell;

evaluating the methylation of the genomic DNA of the human induced pluripotent cell to identify a methylation pattern of at least one CpG differentially methylated region (DMR) in the genomic DNA of the human induced pluripotent stem cell and at least one non-CpG DMR in the genomic DNA of the human induced pluripotent stem cell, wherein the at least one CpG DMR is:

a) a CpG-DMR comprising position 125033730 to position 125034829 of chromosome 12 of the genomic DNA of the human induced pluripotent stem cell;

b) a CpG-DMR comprising position 128952730 to position 128955529 of chromosome 12 of the genomic DNA of the human induced pluripotent stem cell;

c) a CpG-DMR comprising position 129064330 to position 129065329 of chromosome 12 of the genomic DNA of the human induced pluripotent stem cell;

d) a CpG-DMR comprising position 129092430 to position 129093429 of chromosome 12 of the genomic DNA of the human induced pluripotent stem cell;

e) a CpG-DMR comprising position 129209230 to position 129215029 of chromosome 12 of the genomic DNA of the human induced pluripotent stem cell;

f) a CpG-DMR comprising position 87905315 to position 87906414 of chromosome 2 of the genomic DNA of the human induced pluripotent stem cell;

g) a CpG-DMR comprising position 132998500 to position 133001399 of chromosome 10 of the genomic DNA of the human induced pluripotent stem cell;

h) a CpG-DMR comprising position 157173784 to position 157180183 of chromosome 7 of the genomic DNA of the human induced pluripotent stem cell;

i) a CpG-DMR comprising position 47143596 to position 47145195 of chromosome 22 of the genomic DNA of the human induced pluripotent stem cell;

j) a CpG-DMR comprising position 47263296 to position 47266095 of chromosome 22 of the genomic DNA of the human induced pluripotent stem cell;

k) a CpG-DMR comprising position 47349296 to position 47351495 of chromosome 22 of the genomic DNA of the human induced pluripotent stem cell;

and comparing the methylation pattern of the at least one CpG DMR in the genomic DNA of the human induced pluripotent stem cell and the at least one non-CpG DMR in the genomic DNA of the human induced pluripotent stem cell to the methylation pattern of the at least one CpG DMR in genomic DNA of an embryonic stem cell and the at least one non-CpG DMR in genomic DNA of the embryonic stem cell, wherein hypermethylation of the at least one CpG-DMRs as compared to corresponding CpG-DMRs in the DNA of the embryonic stem cell identifies the induced pluripotent stem cell as a reprogrammed human induced pluripotent stem cell;

and wherein a difference in methylation of the at least one non-CpG DMR in the genomic DNA of the human induced pluripotent stem cell as compared to the methylation pattern of the at least one non-CpG DMR in the genomic DNA of the embryonic stem cell, identifies the human pluripotent stem cell as an incompletely reprogrammed human induced pluripotent stem cell.

2. The method of claim 1, wherein said methylation pattern comprises at least one non-CpG hypomethylated DMR.

3. The method of claim 2, wherein the at least one non-CpG hypomethylated DMR is proximal to a telomere or centromere.

4. The method of claim 2, wherein the at least one non-CpG hypomethylated DMR comprises one or more transcriptionally repressed genes.

5. The method of claim 1, wherein the human induced pluripotent stem cell has been propagated in vitro.

6. The method of claim 2, wherein the non-CpG hypomethylated DMR is spatially concordant with a histone 3 comprising three methyl groups covalently attached to the lysine at position 9 (H3K9me3) heterochromatin modification.

7. The method of claim 1, wherein the method further comprises performing a sequencing DNA methylation analysis of the genomic DNA of the induced pluripotent stem cell following the step of contacting the genomic DNA of the induced pluripotent stem cell with bisulfite.

8. The method of claim 1, further comprising
detecting the abundance of mRNA transcripts in the human induced pluripoteint stem cell; and
comparing the abundance of the mRNA transcripts in the induced pluripotent stem cell to the abundance of mRNA transcripts in the embryonic stem cell, wherein a difference in the abundance of the mRNA transcripts indicates that the CpG-DMRs in the human induced pluripotent stem cell are differentially methylated as compared to the corresponding CpG-DMRs in the embryonic stem cell.

9. The method of claim 1, wherein the incompletely reprogrammed human induced pluripotent stem cell has characteristics of differentiated cells.

10. The method of claim 1, wherein the at least one non-CpG DMR includes a transcriptionally induced gene.

11. The method of claim 1, further comprising detecting the presence of a CpG-DMR hypomethylated in the induced pluripotent stem cell as compared to the embryonic stem cell.

12. The method of claim 1, wherein the CpG-DMR is 100 to 4,000 kilobases in length.

* * * * *

SEQUENCE LISTING

<160> NUMBER OF SEQ ID NOS: 6

<210> SEQ ID NO 1
<211> LENGTH: 2632
<212> TYPE: DNA
<213> ORGANISM: Homo sapiens

<400> SEQUENCE: 1

| | | | | | |
|---|---|---|---|---|---|
| gagttcgctc | cggagccgcg | ccgccgccgg | cccagcatct | cgggcgcccg | ccgcccccgc | 60 |
| cgccgccgtc | agcgcgggga | tgtaggatgc | aggcgggcgc | caggttccag | cggcggcggc | 120 |
| ggcagctgca | gcagcagcag | ccccggcggc | ggcagcctct | cctctggccg | atggacgcag | 180 |
| agccgccgcc | gccgccgccc | tgggtctgga | tggtgccggg | ctcggccggg | ctgctccggc | 240 |
| tcagcgcggg | ggtcgtggtt | ccccggtgc | tgctcgcctc | ggccccgccg | cccgcggccc | 300 |
| cgctgctccc | cggtctcccc | ggctggccgg | ccccgagcga | gccggtgctc | ccgctgctgc | 360 |
| cgctgccctc | tgcgccagac | tccgccgccg | ccgccgccgc | gcaccccttc | cccgcgctcc | 420 |
| acgggcagtg | gctgtttggt | ggccattctc | cgtccctagg | actgccccc | tcttccacag | 480 |
| tggagctggt | gccgtcttc | ccacatctct | gcccttctgc | tcttgcaacc | cctattggga | 540 |
| aaagttggat | agacaaaagg | attcctaact | gtaagatctt | ttttaataat | tcctttgctc | 600 |
| tggactcaac | gtggatacat | cctgaggagt | caaggttttt | ccatgggcat | gaaaagcctc | 660 |
| gtttgctggc | aaatcaagta | gctgtgtctc | tgtccaggcc | ggctcctgcc | tccaggccgc | 720 |
| tccccacggt | ggtgttagca | cctcagccca | tcccaggtgg | ctgccataac | agccttaagg | 780 |
| tgaccagcag | ccccgccatt | gccatcgcca | ccgccgccgc | cgctgccatg | gtctccgtgg | 840 |
| accctgagaa | cctccggggc | ccgtcccct | cagcgtgca | gccgcgccac | ttcctgacct | 900 |
| tggcacccat | caaaataccc | ctccggacgt | ccccgtctc | agatacaagg | acagagcggg | 960 |
| gccgagtggc | ccgccctcct | gccctgatgc | tgcgggccca | gaagagccgg | gatggagaca | 1020 |
| aagaagacaa | ggagcctcca | ccgatgctgg | ggggaggaga | ggacagcaca | gccagaggca | 1080 |
| acaggccagt | ggcctccacc | ccggtgcccg | gatcccctg | tgtgtggtc | tggacgggcg | 1140 |
| atgaccgagt | tttcttcttc | aacccaacga | tgcacctgtc | tgtctgggag | aagcccatgg | 1200 |
| acctgaagga | ccgcggagac | ctcaacagga | tcattgagga | cccgcccac | aaacgcaagc | 1260 |
| tggaggcacc | agcaactgac | aacagcgatg | ggtccagttc | tgaagacaac | agggaagacc | 1320 |
| aagatgtgaa | aaccaagagg | aaccggaccg | aaggctgcgg | gagtcccaag | ccagaggagg | 1380 |
| caaagagaga | ggacaaaggc | acaaggacgc | cgcccccgca | gatcctcctg | cctctggagg | 1440 |
| agcgtgtgac | ccacttccga | gacatgctgc | tggagagagg | ggtatcagca | ttttctacct | 1500 |
| gggagaaaga | attacacaaa | atcgtgtttg | acccacgcta | tctcctgctc | aactctgagg | 1560 |
| aacgaaagca | gatatttgaa | cagtttgtca | agacaagaat | aaaagaagaa | tacaaggaaa | 1620 |
| agaaaagtaa | attgctgcta | gccaaagaag | aattcaagaa | acttctagag | gaatctaaag | 1680 |
| tgtctcccag | gaccacgttt | aaggagtttg | cagagaaata | cggccgggat | cagaggttcc | 1740 |
| gacttgttca | aaaagaaag | gaccaggagc | attttttcaa | ccaattcata | cttattctta | 1800 |
| agaaacggga | caaggaaaac | agactaaggc | tgcggaaaat | gagatgagtt | tgtgaaaaaa | 1860 |
| tgcaataagc | ccgggggttg | accctgggcg | tgccggggc | gagggggtca | cggtggagac | 1920 |
| ggacacgggc | gtggggcggc | cgagacctgc | acgcccagc | gggcaccggc | actgcgggt | 1980 |
| cttcgttctc | agaggattac | tgtttcatat | tgaagctctc | tcttttgtac | attcagagtt | 2040 |
| tgatgcattt | ctaatcaccg | tgatacgtcg | atcccttaat | tgttttaatt | atgcaaatta | 2100 |

-continued

```
cttgtaatat acacaaatta tcaatccact gcaggactgt ggggaagcag gaacgggagc    2160
ctctgtaaca atctcaaggc atttgtgtca tcacctaaga cgattggcga aaacttttct    2220
gaaaaccttt gtgaattact tcgtttctcc aggattcccg cagtgttgag gaattcctta    2280
ctctgtccct aggtctcagt ctcgtttctg agtagcagca atagggtttt catcattcat    2340
catagtgaca actgtgagca ttccacacct ggaccgtgga tcacttacag gtttccaagg    2400
gtggccgcgc gttcctccca gaggggcgtc ccggcctgga gcaggagcc gtgttggttg     2460 ccaccggtcc tacttcaaaa gaattatttt gtacaaaatc atcatattaa tatttgagtt    2520 attttattg tatgcccgga gtttgcatga gattttttct catcaccttt gtataaaaaa     2580
tttttaattt ttttaatca ataaatattt taaaccaaaa aaaaaaaaaa aa              2632
```

<210> SEQ ID NO 2
<211> LENGTH: 5777
<212> TYPE: DNA
<213> ORGANISM: Homo sapiens

<400> SEQUENCE: 2

```
gccactcttc gctcgggtaa acaggaaagg aaatacccc tgtggattaa aatttaaaaa       60
aaattctgtt ggggtcgaag gagggaggtg gggtttgcct gcgcgcgtgt tggactccgg     120
agagcaactc aggagcccgc gcggtcgtcg cctcccggcc tggccatgga ctggcgggaa    180
gagggagcag ggcgcccggg ctgctcgggc ccctagccgg gcgctccctc gccaccggcc    240
ccgctgcggg cctctagggg actgagacgt tctcttgttc gcctggacgg cgccggggag    300
cggaggatct gcgctccggg tctccaggat gtgcccgtct gagatgggga cgctgtggca    360
ccactggtcg ccggtactca tcagcctggc cgccctgttt tccaaagtga cggaaggtcg    420
agggatcctt gagagcatcc agaggttttc cttgctgccc acctacctcc ccgtgaccta    480
ccacatcaac aacgcggacg tctccttctt cctgaaggag gccaaccagg atatcatgag    540
gaactccagc ctgcagtccc gggtggagtc atttctgatt tacaaatcca ggaggctgcc    600
tgtcctcaat gccagctacg gcctttctc catcgagcaa gtggtgcccc aggatttaat    660
gctaccttcc aacccatttg gattcaccaa caaattttct cttaactgga aactaaaagc    720
ccacatcctg cgggacaaag tctacctgag ccggcccaaa gtgcaggttc tgttccacat    780
catgggcaga gactgggacg accgcagcgc cggggagaag ctgccgtgcc tgagggtctt    840
tgctttccga gagacccgag aggtgcgggg cagctgccgg ctgcagggga acctggggct    900
gtgcgtggcc gagctggagc tcctgtccag ctggttcagc ccccccacgg tggttgccgg    960
gaggaggaag tccgtggacc agccggaggg daccccgtg gagctctact acaccgtgca    1020 cccaggggt gagagagggg actgcgtcag ggaagacgcg aggagaagca atgggatccg    1080 acaggccac agtgacatcg atgagtccgg gcccccttg cagaggatcg ggagcatctt    1140
cctttatcag acacacagga aaccctccct gagagaactg cgtctggaca cagcgtggc    1200 catccactat ataccaaaga ccgtgaggaa aggagacgtg ctgactttc ctgtttccat    1260 ctccagaaat tccactgaag atcgcttcac gttgagggca aggtgaaga aaggcgtgaa    1320 catcatcggc gtgcgagcca gcagcccttc catttgggat gtcaaggagc gcacggatta    1380
tactggaaag tatgcaccag ctgtcatcgt ttgtcagaag aaagcagctg gctcagaaaa    1440
cagtgcggat ggcgcctcct acgaggtcat gcagatcgat gtggaggtgg aagagcctgg    1500
tgacctgcca gccacacagc tggtcacgtg gcaggtcgag taccccggag agatcacgtc    1560
```

-continued

```
tgacttggga gtgtccaaga tctatgtgag cccaaaggac ttgattggag ttgtgccgct   1620
ggctatggag gcagaaatcc tgaacacagc catcctcacg gggaagacgg tggccgtccc   1680
ggtgaaagtg gtctccgtgg aggacgacgg cacagtgaca gagctgctgg agtctgtgga   1740
gtgtagatcg tctgatgaag acgtgattaa ggtttctgac agatgtgact acgtctttgt   1800
caatgggaaa gaaatgaaag gcaaggtcaa cgtggtggtg aacttcacct accagcacct   1860
gagcagcccc ctggagatga cggtgtgggt gccccggctt ccgctgcaga tcgaggtctc   1920
cgacaccgag ctcaatcaga tcaagggttg gagagtgccc atcgtctcca gcaggaggcc   1980
tgccggggac agtgaagagg aggaggatga tgagcggagg ggccgcgggc gcaccctgca   2040
gtaccagcac gccatggtgc gggtcctgac gcagtttgtg gctgaggcgg ccggccctgg   2100
gggacacctg gccccctgc tgggctcaga ctggcaagtg gacatcacgg agctgataaa   2160
tgacttcatg caggtggagg agcccaggat cgccaagctg caaggcggac agatcctgat   2220
ggggcaggag cttgggatga ccaccattca gatcctgtct cctctgtcag acaccatcct   2280
cgctgaaaag accatcactg tgctggacga gaaggtgacc atcacagacc tcggggtgca   2340
gctggtgaca gggctgtcac tctccttgca gctcagccca ggaagcaaca gggccatctt   2400
tgccactgca gtggctcagg aacttctgca gaggccaaaa caggaagcag ccatcagttg   2460
ctgggtccag ttcagtgatg gctcagtcac gcccttggat atttacgatg ggaaagactt   2520
ctccttgatg gccacatctt tggatgagaa ggtagtctcc atccaccaag ccccaaatt   2580
caagtggcct atcattgctg cggaaacaga aggacaaggc accctggtca aggtggaaat   2640
ggttattagt gaatcctgcc agaaatccaa gcggaagagt gtgttagctg ttggaacggc   2700
aaacatcaaa gttaaatttg gccaaaacga tgctaacccc aacaccagtg acagcagaca   2760
cacagggcga ggggttcaca tggaaaacaa tgtcagtgac agaaggccca aaaaccctc   2820
gcaggaatgg gggagtcagg aaggacagta ctatggcagt tcttctatgg gactcatgga   2880
gggacggggc accacgacag acaggtccat cctgcagaag aagaaaggcc aggaaagcct   2940
tttagatgac aacagccact gcagaccat ccccagcgac ctcaccagct cccagcca   3000
ggtgacctc cccagaagca atggggaaat ggatgggaat gaccttatgc aggcatccaa   3060
agggctgagc gacttagaaa ttgggatgta tgctttgttg ggagtcttct gtttggccat   3120
tttggtcttc ttgataaact gtgtgacctt tgcattaaaa tacagacaca acaggttcc   3180
cttcgaggag caggaaggga tgagtcactc tcatgactgg gttgggttaa gcaaccggac   3240
agagctgttg gagaatcaca tcaactttgc ctcctcgcaa gatgagcaaa tcactgccat   3300
tgacagtggc atggatttcg aggaaagtaa atatctcctc agcacaaact cccaaaaaag   3360
catcaatggg cagctgttca aacctttggg acccatcatc attgatggga agatcagaa   3420
aagtgagccc ccaacatccc ctacctcaaa aggaaaagg gtaaaattta ccaccttcac   3480
cgccgtctcc tcagacgacg agtaccccac caggaactcc atcgtgatga gtagcgagga   3540
tgacattaag tgggtctgcc aggatctgga ccctggggac tgcaaagagc tgcacaacta   3600
catggagagg ttacatgaaa atgtgtaagc cagacacaca cagacattgg ttctcactca   3660
cctttcagcc tttaattcca ggatgtgtag caacggtgcc cccggaagag aaacaaagca   3720
gcaggacaaa ataaggatga cactatccat acagcctcag ccaatgaccc cggctcggcg   3780
gcgaggcctg gagtccgcat cgacgcacac attccagagt acagtgtctt gcttaagagg   3840
tttatcatgc atggcaagat ttttaagact tgaaacaaaa acgagttctg aatcactgag   3900
cgtctgagag cgtccaggaa agaacagcct ctctctctcg aatcaaagca atttggatat   3960
```

```
tgtaaaatcc acatggctcc aatattcaat attgcagact atggaagaaa agtacaactc    4020
aggtggagca tccatggatc gcatccatgg atcaatggga ggaagcgtgt catcgaaact    4080
ggagcagcac atcttgctgt gagcgcgatc acaggcagtc cagtgccgcc gtcagctgtg    4140
ggaggcatga ttgtgagtca ttgtctctca aggctgggc cagagctgtc tcagatcatg     4200
gacaggccaa ggaagtggct gacaaggact gaaagggaac atgtgggcta acaggccaca    4260
aatacctttg taactacatg ccaaggacaa acacatggac gcaaatcctc tgagcccttc    4320
agggtacttc tttatttgta aactaaggat actgggcata gaatttgaat caggttcaaa    4380
gaaccacgct cttttgattc atatcaagtt cacaatgtat ccatttctat tcctccactg    4440
cattgccatc ctccccaaag ccgttggtca cctgtgggtg ggggagggag agggcagttt    4500
gtagtatttg ctgggtcttt tttctccccc tgggttttgt gtcaactccc aagtgacatt    4560
ctgtagagaa gctccccccg caacctgggc atatgtccca cgccgtccgt ctttgaagag    4620
gctggtctct aggcatgggc ggtagtcacg gtgaattcca taccagggga tatacattcc    4680
cttgctttac tagaaagaaa acagggccac ttgggatggg tctttcactg ttcatggcag    4740
atctcctgtc caaagatgtg gcctcgaggc tgttgagaca aatcggggtg cctgtgtgga    4800
acgtgcaggg cgtgtggagt tggggggtt ctgggtgtga aagtggtgga tccagcagga    4860
agcccagcct cacacacacc ggacagcaca gaaaccttct tcatcttgga ggtgcgaagg    4920 gataagggc atcagtgcat gtggtgaaga tgcaggtttg caagcacttg gtcctgcagt     4980
cagccccgaa aggttcagca ttgcttaaga ccagccatga ctctggatat ccctgaatcc    5040
cttcacttat gaagcctatg aagatggggg caaggataca tcagagaatt cctgcctcat    5100
ctcacgctca ctccaaggta gagaatggtg tgttgggtga ttgccagcca gataggatcc    5160
tgcaaaagat ggtcggggc agcgggtggt gggcagaaga ggccgtgctg ttgaattgat     5220
cttctatttt tccctctggt cattttctct ctctctctgc tcttcagttg tctgtttcc     5280 agtctctctg tgtgtctgtc tctgtatctc tctcctcctt tgaacctatc ttctccctgc    5340
ttcctctcca tctcatctct gtaattttga gtgtgtgtct ttactccttc ttcctctcca    5400
tagaattgaa ttctctttag atcatgtgtg tgtaaatttc accagtttac cctcccaacc    5460
ttagccctct cccctgcaac tgtggtgctc ttgagactga ggtttctgca gccagtaagt    5520
cacctgctcc tgtccgcaag cttacctacc ttgtttggtt gggtgattaa gctgtcaccc    5580
cttttcaatg agaatccttt gctttcagta acgtcctcat atttctttcc attcttacct    5640
gtgtcatgtt ctgttgaata ctgcagccgc tgcccgcttc caaatccatc tgcgtgtaga    5700
atgtactgta gattgtaaga atgtaatata tatttataaa cttactgact gtaaatataa    5760
agtttgcatt cagtggc                                                  5777
```

<210> SEQ ID NO 3
<211> LENGTH: 3288
<212> TYPE: DNA
<213> ORGANISM: Homo sapiens

<400> SEQUENCE: 3

```
cgagtcttct catcccggga cgcaaacctc gaaacagctg ccggctggtc ccggccgagg      60
ccggcgcagg gagggaggag ccgcccgggc tgtgggggcg ccgcgagctg ggccggcctc     120
ggtgtgcccg cgccgccagc ccgctccaga cgcgccacct gggcgctcca agaagaggcc    180
gaagtttgcc gcggccgtga gttggagctc gcgccgggcc gctgcgccgg gagctccggg    240
```

-continued

```
ggcttccctc gcttcccggt attgtttgca aactttgctg ctctccgccg cggcccccaa    300
ctcggcggac gccgggcgcg gagagccgag ccggggcgc  tgtgcgcagc gctcgggcca    360
ggccgggcgg gcatgggcgg gggcccgagc aggggtggag agccggggcc agcagcagcc    420
cgtgcccggg agcggcggcg ctgaggggcg cggagctccc cgcgaggaca cgtccaacgc    480
cagcatgcag cgcccgggcc cccgcctgtg gctggtcctg caggtgatgg gctcgtgcgc    540
cgccatcagc tccatggaca tggagcgccc gggcgacggc aaatgccagc ccatcgagat    600
cccgatgtgc aaggacatcg gctacaacat gactcgtatg cccaacctga tgggccacga    660
gaaccagcgc gaggcagcca tccagttgca cgagttcgcg ccgctggtgg agtacggctg    720
ccacggccac ctccgcttct tcctgtgctc gctgtacgcg ccgatgtgca ccgagcaggt    780
ctctaccccc atccccgcct gccgggtcat gtgcgagcag gcccggctca agtgctcccc    840
gattatggag cagttcaact tcaagtggcc cgactccctg gactgccgga aactccccaa    900
caagaacgac cccaactacc tgtgcatgga ggcgcccaac aacggctcgg acgagcccac    960
ccggggctcg ggcctgttcc cgccgctgtt ccggccgcag cggccccaca gcgcgcagga   1020
gcacccgctg aaggacgggg gccccgggcg cggcggctgc gacaacccgg gcaagttcca   1080
ccacgtggag aagagcgcgt cgtgcgcgcc gctctgcacg cccggcgtgg acgtgtactg   1140
gagccgcgag gacaagcgct cgcagtggt  ctggctggcc atctgggcgg tgctgtgctt   1200
cttctccagc gccttcaccg tgctcacctt cctcatcgac ccggcccgct tccgctaccc   1260
cgagcgcccc atcatcttcc tctccatgtg ctactgcgtc tactccgtgg gctacctcat   1320
ccgcctcttc gccggcgccg agagcatcgc ctgcgaccgg gacagcggcc agctctatgt   1380
catccaggag ggactggaga gcaccggctg cacgctggtc ttcctggtcc tctactactt   1440
cggcatggcc agctcgctgt ggtgggtggt cctcacgctc acctggttcc tggccgccgg   1500
caagaagtgg ggccacgagg ccatcgaagc caacagcagc tacttccacc tggcagcctg   1560
ggccatcccg gcggtgaaga ccatcctgat cctggtcatg cgcagggtgg cggggacga   1620
gctcaccggg gtctgctacg tgggcagcat ggacgtcaac gcgctcaccg gcttcgtgct   1680
cattcccctg gcctgctacc tggtcatcgg cacgtccttc atcctctcgg gcttcgtggc   1740
cctgttccac atccggaggg tgatgaagac gggcggcgag aacacggaca gctggagaa   1800
gctcatggtg cgtatcgggc tcttctctgt gctgtacacc gtgccggcca cctgtgtgat   1860
cgcctgctac ttttacgaac gcctcaacat ggattactgg aagatcctgg cggcgcagca   1920
caagtgcaaa atgaacaacc agactaaaac gctggactgc ctgatggccg cctccatccc   1980
cgccgtggag atcttcatgg tgaagatctt tatgctgctg gtggtgggga tcaccagcgg   2040
gatgtggatt tggaccctcc agactctgca gtcctggcag caggtgtgca gccgtaggtt   2100
aaagaagaag agccggagaa aaccggccag cgtgatcacc agcggtggga tttacaaaaa   2160
agcccagcat ccccagaaaa ctcaccacgg gaaatatgag atccctgccc agtcgcccac   2220
ctgcgtgtga acagggctgg agggaagggc acagggcgc  ccggagctaa gatgtggtgc   2280
ttttcttggt tgtgttttc  tttcttcttc ttctttttt  ttttttataa aagcaaaaga   2340
gaaatacata aaaagtgtt  taccctgaaa ttcaggatgc tgtgatacac tgaaaggaaa   2400
aatgtactta aagggttttg ttttgttttg gttttccagc gaagggaagc tcctccagtg   2460
aagtagcctc ttgtgtaact aatttgtggt aaagtagttg attcagccct cagaagaaaa   2520
cttttgttta gagccctccc taaatataca tctgtgtatt tgagttggct ttgctaccca   2580
tttacaaata agaggacaga taactgcttt gcaaattcaa gagcctcccc tgggttaaca   2640
```

```
aatgagccat ccccagggcc caccccagg aaggccacag tgctgggcgg catccctgca   2700
gaggaaagac aggacccggg gcccgcctca caccccagtg gatttggagt tgcttaaaat   2760
agactccggc cttcaccaat agtctctctg caagacagaa acctccatca aacctcacat   2820
ttgtgaactc aaacgatgtg caatacattt ttttctcttt ccttgaaaat aaaaagagaa   2880
acaagtattt tgctatatat aaagacaaca aagaaatct cctaacaaaa gaactaagag   2940
gcccagccct cagaaaccct tcagtgctac attttgtggc ttttaatgg aaaccaagcc   3000 aatgttatag acgtttggac tgatttgtgg aaggagggg ggaagaggga aaggatcat   3060 tcaaaagtta cccaaagggc ttattgactc tttctattgt aaacaaatg atttccacaa   3120 acagatcagg aagcactagg ttggcagaga cactttgtct agtgtattct cttcacagtg   3180
ccaggaaaga gtggtttctg cgtgtgtata tttgtaatat atgatatttt tcatgctcca   3240 ctatttatt aaaaataaaa tatgttcttt agtttgctgc taaaaaaa                 3288

<210> SEQ ID NO 4
<211> LENGTH: 4104
<212> TYPE: DNA
<213> ORGANISM: Homo sapiens

<400> SEQUENCE: 4
cgggcgggtg tggccagggg tgtgggtctg tgagggaccg gtcggaaggg cgtcgcgcgg     60
cctcgggtga catgcggggg gcggcgagcg cgagtgtccg cgagccgacg ccgctcccgg    120
gtagaggcgc cccccgcaca aagccccggg cgggccgagg cccgactgta gggactccag    180
ccaccttggc cctccctgcc cggggaaggc cgcgctcaag gaatggcctc gcatccaaag    240
gccagcgagg agcggcccct acggggcctg ggcacagagc tctgccttcc agggacactg    300
ctcttcccca ggagagaaac aagaagctgg aggctgtggg gacaggaatt gaacctaaag    360
ccatgtccca gggcttggtg acatttgggg atgtggctgt agatttctcc caagaggagt    420
gggagtggct gaacccccatt cagaggaact tgtacaggaa ggtgatgttg agaactaca    480 ggaacctggc atcgctggga cttgtgtttt ctaagcccga tgtgatctcc tcgttggaac    540
aaggaaaaga gccttggaca gtgaagcgaa agatgacaag agcctggtgc ccagacttga    600
aggctgtgtg gaagatcaag gagttacctc tcaagaagga cttctgcgaa ggaaagctat    660
cccaggcagt gataacagag agactcacaa gctataatct ggagtactct ctgttagggg    720
aacactggga ttatgatgct ctgtttgaga cacagccggg cttggtgact atcaaaaacc    780
tggctgttga cttccgccag cagctacacc cagctcagaa gaatttctgt aagaatggga    840
tatgggagaa caacagtgac ctgggatcag caggacattg tgtggctaag ccagatttag    900
tctctttact agagcaagag aaggagccct ggatggtgaa gcgagagctg acaggaagcc    960
tgttctcagg ccagcgatct gtacatgaga cccaggaatt atttccaaag caagattcat   1020
atgctgaagg ggtaacagac agaacctcaa acactaaact tgattgttcc agtttcagag   1080
aaaattggga ttctgactat gtgtttggaa ggaagcttgc agtaggtcaa gagacacaat   1140
tcaggcaaga gccaattact cataacaaaa ccctctctaa ggaaagagaa cgtacatata   1200
acaaatctgg aagatggttc tatttggacg attcagaaga gaagttcat aatcgtgatt   1260 caattaaaaa ttttcaaaaa agttcagtgg taataaaaca aacaggcatc tatgcaggaa   1320
aaaagctttt caagtgtaat gaatgtaaga aaacttttac ccagagctca tctcttactg   1380
ttcatcagag aattcacact ggagagaaac cttataaatg taatgaatgt gggaaggcct   1440
```

```
ttagtgacgg ctcatccttt gcccgacacc agagatgtca cactggcaag aagccctatg    1500
agtgcattga gtgtgggaaa gctttcatac agaacacatc ccttatccgt cactggagat    1560
actatcatac tggggagaaa ccctttgatt gcatcgattg tgggaaagcc ttcagtgacc    1620
acatagggct taatcaacac aggagaattc atactggaga gaaacccttac aaatgtgatg    1680 tatgtcacaa atccttcagg tatggttcct cccttactgt acatcaaagg attcataccg    1740
gagaaaaacc atatgaatgt gatgtttgca gaaaagcctt cagccatcat gcatcactca    1800
ctcaacatca aagagtacat tctggagaaa agccttttaa gtgtaaagag tgcggaaaag    1860
cttttaggca gaatatacac cttgccagtc atttaaggat tcatactggg gagaagcctt    1920
ttgaatgtgc ggagtgtgga aaatccttca gcatcagttc tcagcttgcc actcatcaga    1980
gaatccatac tggagagaag ccctatgaat gtaaggtttg tagtaaagcg ttcacccaga    2040
aggctcacct tgcacagcat cagaaaaccc atacaggaga gaaaccatat gagtgcaagg    2100
aatgcggtaa agccttcagc cagaccacac acctcattca acatcagaga gttcacactg    2160
gtgagaaacc ctataaatgt atggaatgtg gaaaggcctt tggtgataac tcatcctgta    2220
ctcaacatca aagactgcac actggccaaa gaccttatga atgtattgag tgtggaaagg    2280
cattcaagac aaaatcctcc cttatttgtc atcgcagaag tcatactgga gaaaaacctt    2340
atgaatgcag tgtgtgtggc aaagccttta gtcatcgtca atcccttagt gtacatcaga    2400
gaatccattc tggaaagaaa ccatatgaat gtaaggaatg taggaaaacc ttcatccaaa    2460
ttggacacct taatcaacat aagagagttc atactggaga gagatcttat aactataaga    2520
aaagcagaaa agtcttcagg caaactgctc acttagctca tcatcagcga attcatactg    2580
gagagtcgtc aacatgcccc tctttacctt ccacgtcaaa tcctgtggat ctgtttccca    2640
aatttctctg gaatccatcc tccctcccat caccatagcc tcgagacgtc atttctgttt    2700
gactactcca gcagtttaaa accccatctc cctgcccttt tgttttcttt ttgtcccttta    2760 ttagttagtt cttcacataa gtgtaaatgt aacttattca ctcctcttgt aaaacttata    2820
gtttctttaa attggttaat gtgtgagatg tgctcagcac agtgcctggt ccatagtaag    2880
tgctcagtaa acttagctgt tttaaaaact ttgtatttga acattgaaaa gttacagtag    2940
tcagctctga taaaaaaatg atgcagtagg gtgagggtag gaaaaagcac attttctatc    3000
aggaacagaa ttctccagta gtgggtgagg ttttgccttt gttggtttta aaacttgatt    3060
ctataatgcc aagttagttt tgtggctttc catctgaccc tatgtgaatg taaggtgatg    3120
tgaccttgtt ggtgagaaaa ttaaacttta catttgactt gatttgtttt agaaagtcta    3180
gggaccatga atgaataggc cagctgggac aaatgaattt aaaaaaatcag aaaaatgcaa    3240 gatttatatg catgaagtta aaacaactga cgttactcaa gaattagaaa actttgcaag    3300
atttgacttg tttaaaaatc acatttataa gtgaaccgta ttaaaacttt taaggaacca    3360
ttcattgtga ggtaaactga tccagaatag gggtcagcaa actatgactc atggccacag    3420
tctcactgac tgttttttgta tggtccatga tctagaattt aaaaaaattt taaagggttg    3480
aaaaaagtga aaagaatatt ttcaacatga aaattatatg aaatttaagt tttggtgtct    3540
gtaaataaag ttttgttggc ttcagccaca cagtgattta caccttgatt gtgctgcttc    3600
caggctgtag cagcagagtt gagcagttgt gacaggagac catgtggcct gcagagccca    3660
aatatctact gtctgatcct acacagaaaa tgtgtgtgat ccctgctatg gagcagaggt    3720
tatcaaacta aagcccatgg accaaatcct atctgctgct tgttttttgta aatagagttt    3780 tatcaaacca cagccatgct tacttgttta gctattgact atggctgctt tagacaactg    3840
```

-continued

```
tgacagacta tatggctcgc aaaactgcaa atatttccta tcctttaaca gaaagtttgc    3900
caacctctgc tctagagtag agaaaaatgt ataaaagatt ttaattttat gagggcaata    3960
caactgtcac atcagaaaca agaaaacaaa tgataaagga actcatttat caatagaggt    4020
gaaaggaaat tattaaacta tattgaaaaa taaagatgtc aataaaagga gaatgatat     4080 ttttctaaaa aaaaaaaaaa aaaa                                            4104
```

<210> SEQ ID NO 5
<211> LENGTH: 2615
<212> TYPE: DNA
<213> ORGANISM: Homo sapiens

<400> SEQUENCE: 5

```
gcggcggcgg cggaggatgg cgcgcgcggg gcccgcacgt ggaggccggc gcggggggcgc     60 gggcagggcc ggctgctgag acgcgctgct gcccccgcg cgggcgccgc ggcttcaatg    120
gcgccatcgc ccaggaccgg cagccggcaa gatgcgaccg ccctgcccag catgtcctca    180
actttctggg cgttcatgat cctggccagc ctgctcatcg cctactgcag tcagctggcc    240
gccggcacct gtgagattgt gaccttggac cgggacagca gccagcctcg gaggacgatc    300
gcccggcaga ccgcccgctg tgcgtgtaga aggggcaga tcgccggcac cacgagagcc    360
cggcccgcct gtgtggacgc aagaatcatc aagaccaagc agtggtgtga catgcttccg    420
tgtctggagg gggaaggctg cgacttgtta atcaaccggt caggctggac gtgcacgcag    480
cccgcgggga ggataaagac caccacggtc tcctgacaaa cacagccct gaggggcccc     540 gggagtggcc ttggctccct ggagagccca cgtctcagcc acagttctcc actcgcctcg    600
gacttcaccc gttctctgcc gcccgcccac tccgtttccc tgtggtccgt gaaggacggc    660
ctcaggcctt ggcatcctga gcttcggtct gtccagccga cccgaggagg ccggactcag    720
acacataggc gggggcggc acctggcatc agcaatacgc agtctgtggg agcccggccg    780
cgcccagccc ccgccgaccg tggcgttggc cctgctgtcc tcagaggagg aggaggagga    840
ggcagctccg gcagccacag aaggctgcag cccagcccgc ctgagacacg acgcctgccc    900
caggggactg tcaggcacag aagcggcctc ctcccgtgcc ccagactgtc cgaattgctt    960
ttattttctt atactttcag tatactccat agaccaaaga gcaaaatcta tctgaacctg   1020
gacgcaccct cactgtcagg gtccctgggg tcgcttgtgc gggcgggagg gcaatggtgg   1080
cagagacatg ctggtggccc cggcggagcg gagagggcgg ccgtggtgga ggcctccacc   1140
ccaggagcac cccgcgcacc ctcggaggac gggcttcggc tgcgcggagg ccgtggcaca   1200
cctgcgggag gcagcgacgg cccccacgca gacgccggga acgcaggccg ctttattcct   1260
ctgtacttag atcaacttga ccgtactaaa atcccttttct gttttaacca gttaaacatg   1320
cctcttctac agctccattt ttgatagttg ataatccag tatctgccaa gagcatgttg    1380
ggtctcccgt gactgctgcc tcatcgatac cccatttagc tccagaaagc aaagaaaact   1440
cgagtaacac ttgtttgaaa gagatcatta aatgtatttt gcaaagccta agttatata    1500 tttaacagtt tttatatgtt gtatatttgt agaaaatcct atttaacaat taacgtggca   1560
gtcccggccg tcctgagagt cgggccgagc ccgtgtgtt tctgaagact ctggggtgg    1620 gacacggcgg ggaggtggtg ccccgcggac cccggggtgc caggcacgga aggcgggact   1680
ctgggagaag cgtgcggagg accgtggcgt cggcgtcccg gatgtgtcgg tcgtgccggg   1740
ggaggccggg ttcccctcgc tgcgggccag gcttggctcc tgattccctc tctggtccct   1800
```

```
gtattggtca acacttgagc gtacaatatc ttgaacatgc ttcttccaat gggttttgtt      1860
tcccatttcc tgcccctttc gccactcacg gaccttgagg ccagttgacg gcccttctcc      1920
ccacgcctgt gtccccgcgt tctgagaagt cctctgtctt cgtgtcacta ggtccagaaa      1980
gtcgcgccgg gcagaggcgc aggcggggcc ggcaggccg aggaataagc gacaattctg       2040 gttttttctcc cctggccgtc gttcgccagc ctccttcatt ttcctgagtt cccgctgaag     2100
tatatactac ctatgagtcc aattaacatg agtattatgc tagttctatc ctactaaaaa     2160
aaacgtaaaa aaataactat atagaagctg ttccagcaac catagactga agatacgaaa     2220
gaaaatccat ttatttaaga cctgttccgg tatccatgag gacataattt acctttcagt     2280
caccacaaat ttataggcat ttgtatcctg gactaaaaga aggggctgag gttgggtttg     2340
tcatcacaga gggggtgggc ctggaaaggg tccttcccaa gctgcccgg ctccggcggc      2400 ccgggccggc agcctctgcc agccagcgtc ctcacggcct cccctcgcc tgtttcttt      2460 gaaagcaagt gtagacacct tcgagggcag agatcgggag atttaagatg ttacagcata     2520
tttttttttc ttgttttaca gtattcaatt ttgtgttgat tcagctaaat tatgaaaaat     2580
aaagaaaaac tcctttgata aaaaaaaaa aaaaa                                2615

<210> SEQ ID NO 6
<211> LENGTH: 2652
<212> TYPE: DNA
<213> ORGANISM: Homo sapiens

<400> SEQUENCE: 6
aaagacacaa atcgcctccc ggagtggcgc ctccagtcgc ggcggagcgc ggcgttggcg       60
gcggatggag ggcgcgagcg ggcggccgcg gaggctgcac ccggcggggc gctgatgcgg      120
cgcctggacc ttcgctgcgc gacttcgggg gcgtcggccg agttgggact ccgcgatgca      180
gctcctgaag gcgctctggg cactggcagg ggccgcgctc tgctgcttcc tcgtcctagt      240
gatccacgcg cagttcctca agaaggtca gctggccgcc ggcacctgtg agattgtgac      300
cttggaccgg gacagcagcc agcctcggag gacgatcgcc cggcagaccg cccgctgtgc      360
gtgtagaaag gggcagatcg ccggcaccac gagagcccgg cccgcctgtg tggacgcaag      420
aatcatcaag accaagcagt ggtgtgacat gcttccgtgt ctggagggggg aaggctgcga     480 cttgttaatc aaccggtcag gctggacgtg cacgcagccc ggcgggagga taaagaccac      540
cacggtctcc tgacaaacac agcccctgag gggcccgggg agtggccttg gctccctgga    600
gagcccacgt ctcagccaca gttctccact cgcctcggac ttcacccgtt ctctgccgcc      660
cgcccactcc gttccctgt ggtccgtgaa ggacggcctc aggccttggc atcctgagct      720
tcggtctgtc cagccgaccc gaggaggccg gactcagaca cataggcggg gggcggcacc      780
tggcatcagc aatacgcagt ctgtgggagc ccggccgcgc ccagccccg ccgaccgtgg     840 cgttggccct gctgtcctca gaggaggagg aggaggaggc agctccggca gccacagaag     900
gctgcagccc agcccgcctg agacacgacg cctgccccag gggactgtca ggcacagaag      960
cggcctcctc ccgtgcccca gactgtccga attgcttta ttttcttata ctttcagtat     1020
actccataga ccaaagagca aaatctatct gaacctggac gcaccctcac tgtcagggtc     1080 cctgggggtcg cttgtgcggg cggagggca atggtggcag agacatgctg gtggccccgg    1140
cggagcggag agggcggccg tggtggaggc ctccaccca ggagcacccc gcgcaccctc     1200
ggaggacggg cttcggctgc gcggaggccg tggcacacct gcgggaggca gcgacggccc     1260
ccacgcagac gccgggaacg caggccgctt tattcctctg tacttagatc aacttgaccg     1320
```

```
tactaaaatc cctttctgtt ttaaccagtt aaacatgcct cttctacagc tccatttttg    1380
atagttggat aatccagtat ctgccaagag catgttgggt ctcccgtgac tgctgcctca    1440 tcgataeccc atttagctcc agaaagcaaa gaaaactcga gtaacacttg tttgaaagag    1500
atcattaaat gtattttgca aagcctaaag ttatatattt aacagttttt atatgttgta    1560
tatttgtaga aaatcctatt taacaattaa cgtggcagtc ccggccgtcc tgagagtcgg    1620
gccgagcccc gtgtgtttct gaagactctg ggggtgggac acggcgggga ggtggtgccc    1680
cgcggacccc ggggtgccag gcacggaagg cgggactctg ggagaagcgt gcggaggacc    1740
gtggcgtcgg cgtcccggat gtgtcggtcg tgcccgggga ggccgggttc ccctcgctgc    1800
gggccaggct tggctcctga ttccctctct ggtccctgta ttggtcaaca cttgagcgta    1860
caatatcttg aacatgcttc ttccaatggg ttttgtttcc catttcctgc cccttttcgcc   1920 actcacggac cttgaggcca gttgacggcc cttctcccca cgcctgtgtc cccgcgttct    1980
gagaagtcct ctgtcttcgt gtcactaggt ccagaaagtc gcgccgggca gaggcgcagg    2040
cggggccggc agggccgagg aataagcgac aattctggtt tttctcccct ggccgtcgtt    2100
cgccagcctc cttcattttc ctgagttccc gctgaagtat atactaccta tgagtccaat    2160
taacatgagt attatgctag ttctatccta ctaaaaaaaa cgtaaaaaaa taactatata    2220
gaagctgttc cagcaaccat agactgaaga tacgaaagaa aatccattta tttaagacct    2280
gttccggtat ccatgaggac ataatttacc tttcagtcac cacaaattta taggcatttg    2340
tatcctggac taaaagaagg ggctgaggtt gggtttgtca tcacagaggg ggtgggcctg    2400
gaaagggtcc ttcccaagct gccccggctc cggcggcccg ggccggcagc ctctgccagc    2460
cagcgtcctc acggcctccc cctcgcctgt ttcttttgaa agcaagtgta gacaccttcg    2520
agggcagaga tcgggagatt taagatgtta cagcatattt ttttttcttg ttttacagta    2580
ttcaattttg tgttgattca gctaaattat gaaaaataaa gaaaaactcc tttgataaaa    2640
aaaaaaaaaa aa                                                        2652
```